(12) United States Patent
Yamada et al.

(10) Patent No.: US 11,807,593 B2
(45) Date of Patent: Nov. 7, 2023

(54) ORGANIC COMPOUND, ORGANIC LIGHT-EMITTING ELEMENT, DISPLAY APPARATUS, IMAGE PICKUP APPARATUS, LIGHTING APPARATUS, AND MOVING OBJECT

(71) Applicant: CANON KABUSHIKI KAISHA, Tokyo (JP)

(72) Inventors: Naoki Yamada, Inagi (JP); Jun Kamatani, Tokyo (JP); Hiroki Ohrui, Kawasaki (JP); Yosuke Nishide, Kawasaki (JP); Hirokazu Miyashita, Ebina (JP); Satoru Shiobara, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 293 days.

(21) Appl. No.: 17/010,355

(22) Filed: Sep. 2, 2020

(65) Prior Publication Data

US 2021/0101864 A1    Apr. 8, 2021

(30) Foreign Application Priority Data

Oct. 3, 2019  (JP) .................................. 2019-183347
May 25, 2020 (JP) .................................. 2020-090594

(51) Int. Cl.
*H10K 50/11*     (2023.01)
*C07C 255/51*    (2006.01)
(Continued)

(52) U.S. Cl.
CPC ............ *C07C 255/51* (2013.01); *H10K 50/11* (2023.02); *H10K 85/624* (2023.02);
(Continued)

(58) Field of Classification Search
None
See application file for complete search history.

(56) References Cited

U.S. PATENT DOCUMENTS 8,948,564 B1 *   2/2015   Sherman ................. F21K 9/232
                                                   362/628
2009/0147331 A1 * 6/2009  Ashkenazi ............... G02B 5/32
                                                    359/13
(Continued)

FOREIGN PATENT DOCUMENTS

CN     102245546 A    11/2011
CN     112441949 A     3/2021
(Continued)

OTHER PUBLICATIONS

Wu, Tsun-Cheng et al., "Synthesis and Structural Analysis of a Highly Curved Buckybowl Containing Corannulene and Sumanene Fragments", Journal of the American Chemical Society, 2011, pp. 16319-16321, vol. 133, No. 41.
(Continued)

*Primary Examiner* — Gregory D Clark
(74) *Attorney, Agent, or Firm* — Canon U.S.A., Inc., IP Division

(57) ABSTRACT

An organic compound represented by formula (1).

(1)

(Continued)

In the formula (1), $R_1$ to $R_{18}$ are each independently selected from the group consisting of a hydrogen atom and a substituent. At least one of $R_1$ to $R_{18}$ represents a substituent. The substituent is an aryl group having at least one cyano group or a heterocyclic group having at least one cyano group.

24 Claims, 6 Drawing Sheets

(51) Int. Cl.
*H10K 85/60* (2023.01)
*H10K 101/40* (2023.01)
*H10K 101/30* (2023.01)

(52) U.S. Cl.
CPC ....... *H10K 85/654* (2023.02); *H10K 2101/30* (2023.02); *H10K 2101/40* (2023.02)

(56) References Cited

U.S. PATENT DOCUMENTS

| | | |
|---|---|---|
| 2010/0026171 A1 | 2/2010 | Negishi |
| 2013/0033416 A1 | 2/2013 | Kamatani |
| 2020/0161558 A1* | 5/2020 | Takaya ................ H01L 51/0054 |

FOREIGN PATENT DOCUMENTS

| | | |
|---|---|---|
| DE | 10 2019 108200 A1 | 10/2019 |
| EP | 2314558 B1 | 5/2014 |
| EP | 2379473 B1 | 2/2017 |
| JP | 2009-221180 A | 10/2009 |
| JP | 2010-143879 A | 7/2010 |
| JP | 2010-254610 A | 11/2010 |
| JP | 2012-246258 A | 12/2012 |
| JP | 2016-015388 A | 1/2016 |
| JP | 2018-76259 A | 5/2018 |
| JP | 2020-026406 A | 2/2020 |
| JP | 2021-038187 A | 3/2021 |
| WO | 2007/099802 A1 | 9/2007 |
| WO | 2008/120806 A1 | 10/2008 |
| WO | 2010/071224 A1 | 6/2010 |
| WO | 2013/042357 A1 | 3/2013 |
| WO | 2018/179482 A1 | 10/2018 |
| WO | 2021/085131 A1 | 5/2021 |

OTHER PUBLICATIONS

Wu, Tsun-Cheng et al., "Bowl-Shaped Fragments of C70 or Higher Fullerenes: Synthesis, Structural Analysis, and Inversion Dynamics", Angewandte Chemie, International Edition, 2013, pp. 1289-1293, vol. 52, No. 4.

Schmidt, Bernd M. et al., "Fluorinated and Trifluoromethylated Corannulenes", Chemistry—A European Journal, 2013, pp. 13872-13880, vol. 19, No. 41.

\* cited by examiner

ORGANIC COMPOUND, ORGANIC LIGHT-EMITTING ELEMENT, DISPLAY APPARATUS, IMAGE PICKUP APPARATUS, LIGHTING APPARATUS, AND MOVING OBJECT

BACKGROUND OF THE INVENTION

Field of the Invention

The present disclosure relates to an organic compound and to an organic light-emitting element, a display apparatus, an image pickup apparatus, a lighting apparatus, and a moving object including the organic compound.

Description of the Related Art

Organic light-emitting elements (also referred to as organic electroluminescent elements) are electronic elements including a pair of electrodes and an organic compound layer disposed between the electrodes. By injecting electrons and holes through the pair of electrodes, excitons of a luminescent organic compound in the organic compound layer are generated. The organic light-emitting elements emit light when the excitons return to their ground state.

Recent remarkable progress in organic light-emitting elements can achieve low driving voltage, various emission wavelengths, high-speed response, and reductions in the thickness and weight of light-emitting devices.

The standards of sRGB and AdobeRGB have been known as a color reproduction range used for displays, and materials suitable for such a color reproduction range have been demanded. In recent years, the reproduction of BT2020, which is the standard having a wider color reproduction range, has been demanded.

Compounds having good light-emitting properties have been enthusiastically created to date. Japanese Patent Laid-Open No. 2010-143879 (hereinafter PTL 1) discloses an organic compound represented by structural formula below as an organic compound having good light-emitting properties. In this specification, this organic compound is referred to as a compound A.

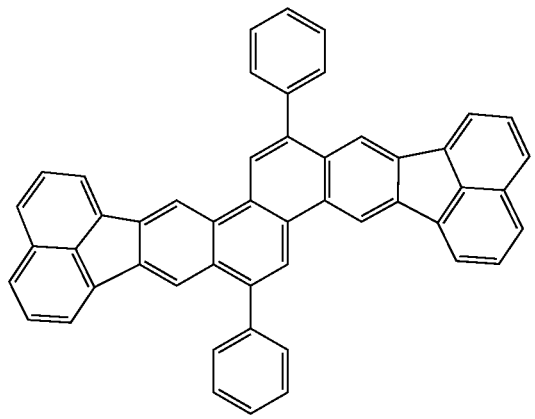

Compound A

The compound A disclosed in PTL 1 is a blue light-emitting material. However, the color purity of blue light emission is not sufficient in consideration of the color reproduction range required for sRGB, AdobeRGB, and BT2020.

SUMMARY OF THE INVENTION

In view of the foregoing, the present disclosure provides a blue light-emitting material with a high color purity required for the color reproduction range of BT2020.

An organic compound according to an aspect of the present disclosure is represented by formula (1) below.

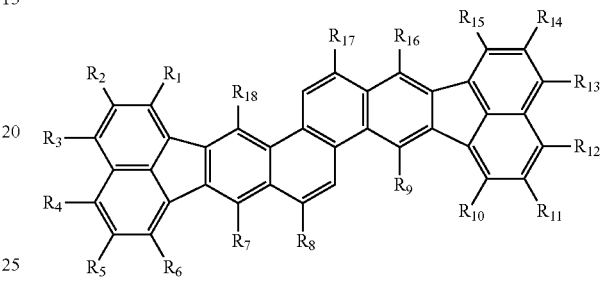

(1)

In the formula (1), $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group. At least one of $R_1$ to $R_{18}$ represents the aryl group having at least one cyano group or the heterocyclic group having at least one cyano group.

Further features of the present disclosure will become apparent from the following description of exemplary embodiments with reference to the attached drawings.

DESCRIPTION OF THE EMBODIMENTS

Figure 1:
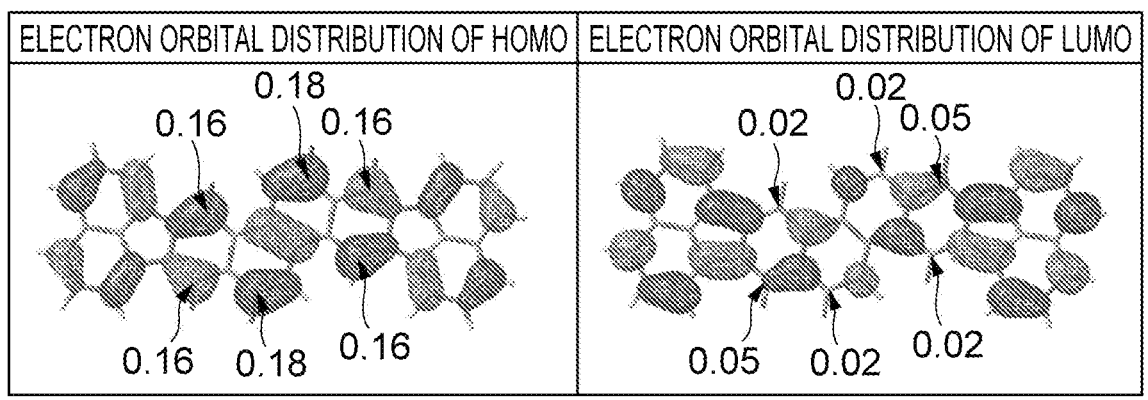
FIG. 1 illustrates an electron orbital distribution of HOMO and an electron orbital distribution of LUMO of a basic skeleton in an organic compound according to an embodiment of the present disclosure.

An organic compound according to an embodiment of the present disclosure will be described. The organic compound according to an embodiment of the present disclosure is an organic compound represented by formula (1) below. The organic compound according to an embodiment of the present disclosure is an organic compound that emits blue light with a high color purity when having a particular substituent in addition to a basic skeleton. In this specification, the basic skeleton refers to a skeleton in which $R_1$ to $R_{18}$ of the organic compound represented by the formula (1) each represent a hydrogen atom. In this specification, high color purity means that the emission coordinates expressed by the CIE coordinates are close to blue coordinates of BT2020, that is, (0.131, 0.046).

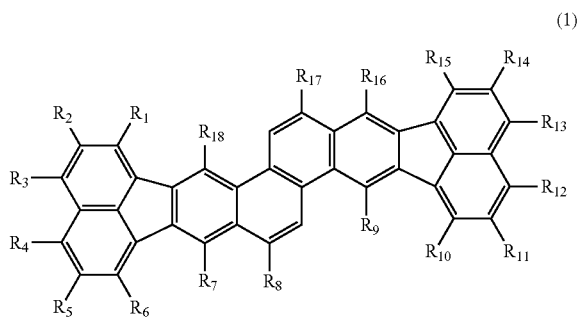

(1)

In the formula (1), $R_1$ to $R_{18}$ are each independently selected from a hydrogen atom and a substituent. The substituents are each independently selected from the group consisting of a halogen atom, an alkyl group, an alkoxy group, an amino group, an aryl group, and a heterocyclic group.

At least one of $R_1$ to $R_{18}$ represents the aryl group having at least one cyano group or the heterocyclic group having at least one cyano group.

In this embodiment, non-limiting examples of the halogen atom include fluorine, chlorine, bromine, and iodine.

In this embodiment, non-limiting examples of the alkyl group include a methyl group, an ethyl group, a n-propyl group, an isopropyl group, a n-butyl group, a tert-butyl group, a sec-butyl group, an octyl group, a cyclohexyl group, an 1-adamantyl group, and an 2-adamantyl group. The alkyl group may have 1 to 10 carbon atoms.

In this embodiment, non-limiting examples of the alkoxy group include a methoxy group, an ethoxy group, a propoxy group, an 2-ethyl-octyloxy group, and a benzyloxy group. The alkoxy group may have 1 to 6 carbon atoms.

In this embodiment, non-limiting examples of the amino group include an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, an N-phenyl-N-(4-trifluoromethylphenyl)amino group, and an N-piperidyl group. That is, the amino group may be an amino group having an alkyl group, an aryl group, or an aralkyl group as a substituent. The aryl group introduced to the amino group as a substituent may be specifically a phenyl group, a naphthyl group, or a benzyl group. The phenyl group, the naphthyl group, and the benzyl group may have an alkyl group as a substituent. This alkyl group may have 1 to 10 carbon atoms. Alternatively, this alkyl group may have 1 to 4 carbon atoms.

In this embodiment, non-limiting examples of the aryl group include a phenyl group, a naphthyl group, an indenyl group, a biphenyl group, a terphenyl group, a fluorenyl group, a phenanthryl group, and a triphenylenyl group. The aryl group may have 6 to 18 carbon atoms.

In this embodiment, non-limiting examples of the heterocyclic group include a pyridyl group, a pyrimidyl group, a pyrazyl group, a triazyl group, a benzofuranyl group, a benzothiophenyl group, a dibenzofuranyl group, a dibenzothiophenyl group, a dibenzoselenophenyl group, a dibenzotellurophenyl group, an oxazolyl group, an oxadiazolyl group, a thiazolyl group, a thiadiazolyl group, a carbazolyl group, an acridinyl group, a phenanthrolyl group, a quinolyl group, and an isoquinolyl group. That is, the heterocyclic group is a substituent having a nitrogen atom, an oxygen atom, or a sulfur atom as a heteroatom. The heterocyclic group may have one or more heteroatoms and may have one or more types of heteroatoms. The heterocyclic group may have 3 to 15 carbon atoms.

In this embodiment, non-limiting examples of the aryloxy group include a phenoxy group and a thienyloxy group.

In this embodiment, non-limiting examples of the silyl group include a trimethylsilyl group and a triphenylsilyl group. The silyl group may have an alkyl group or an aryl group as a substituent. This alkyl group may have 1 to 10 carbon atoms. This aryl group may have 6 to 18 carbon atoms.

The above-described alkyl group, alkoxy group, amino group, aryl group, heterocyclic group, and aryloxy group may further have a substituent other than those described for each of the groups. Non-limiting examples of the substituent that may be further introduced include alkyl groups having 1 to 4 carbon atoms such as a methyl group, an ethyl group, a n-propyl group, an isopropyl group, a n-butyl group, and a tert-butyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxy groups such as a methoxy group, an ethoxy group, and a propoxy group; aryloxy groups such as a phenoxy group; halogen atoms such as fluorine, chlorine, bromine, and iodine; and cyano groups.

Next, a method for synthesizing the organic compound according to an embodiment of the present disclosure will be described. The organic compound according to an embodiment of the present disclosure is synthesized through, for example, the following reaction scheme.

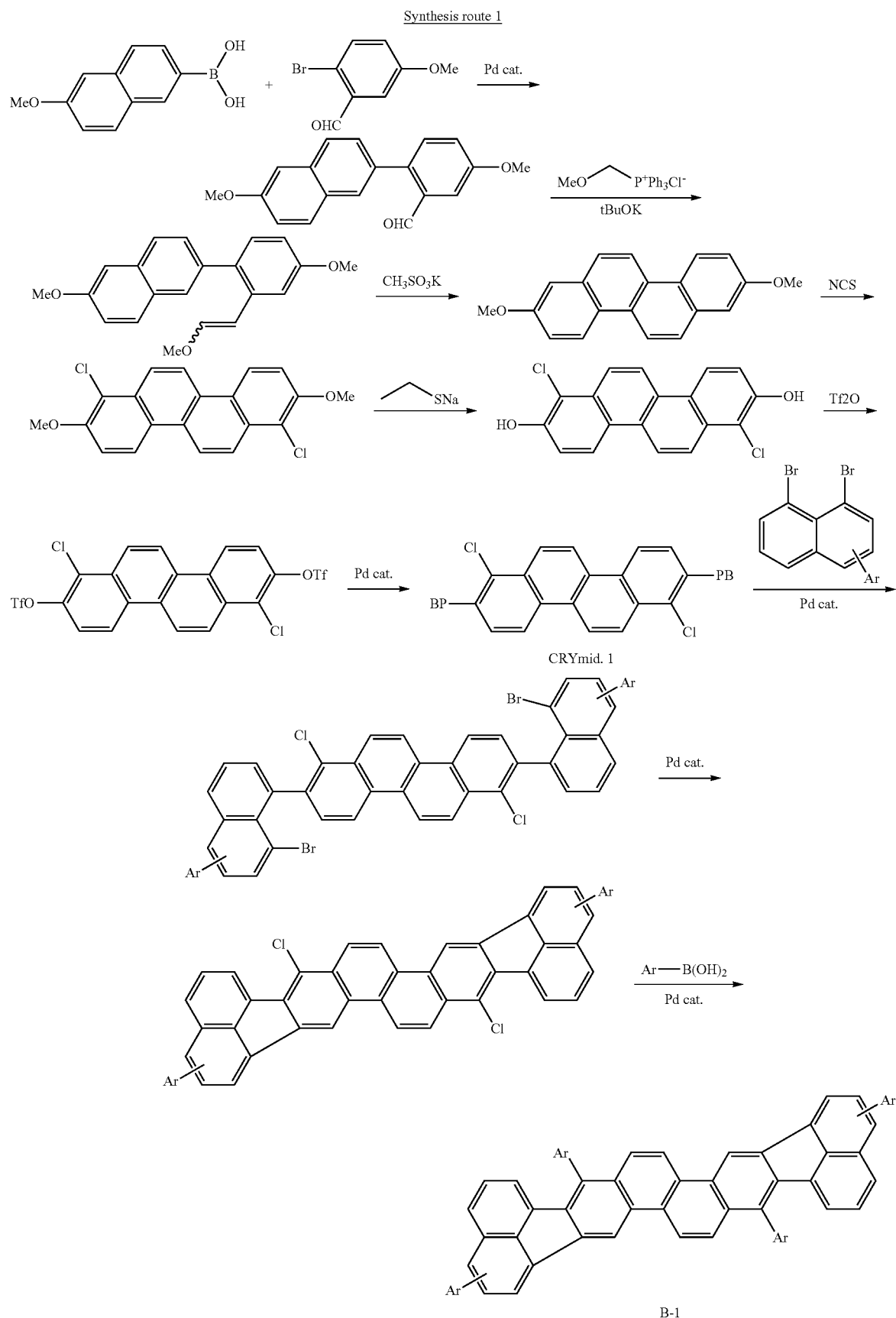

-continued
Synthesis route 2
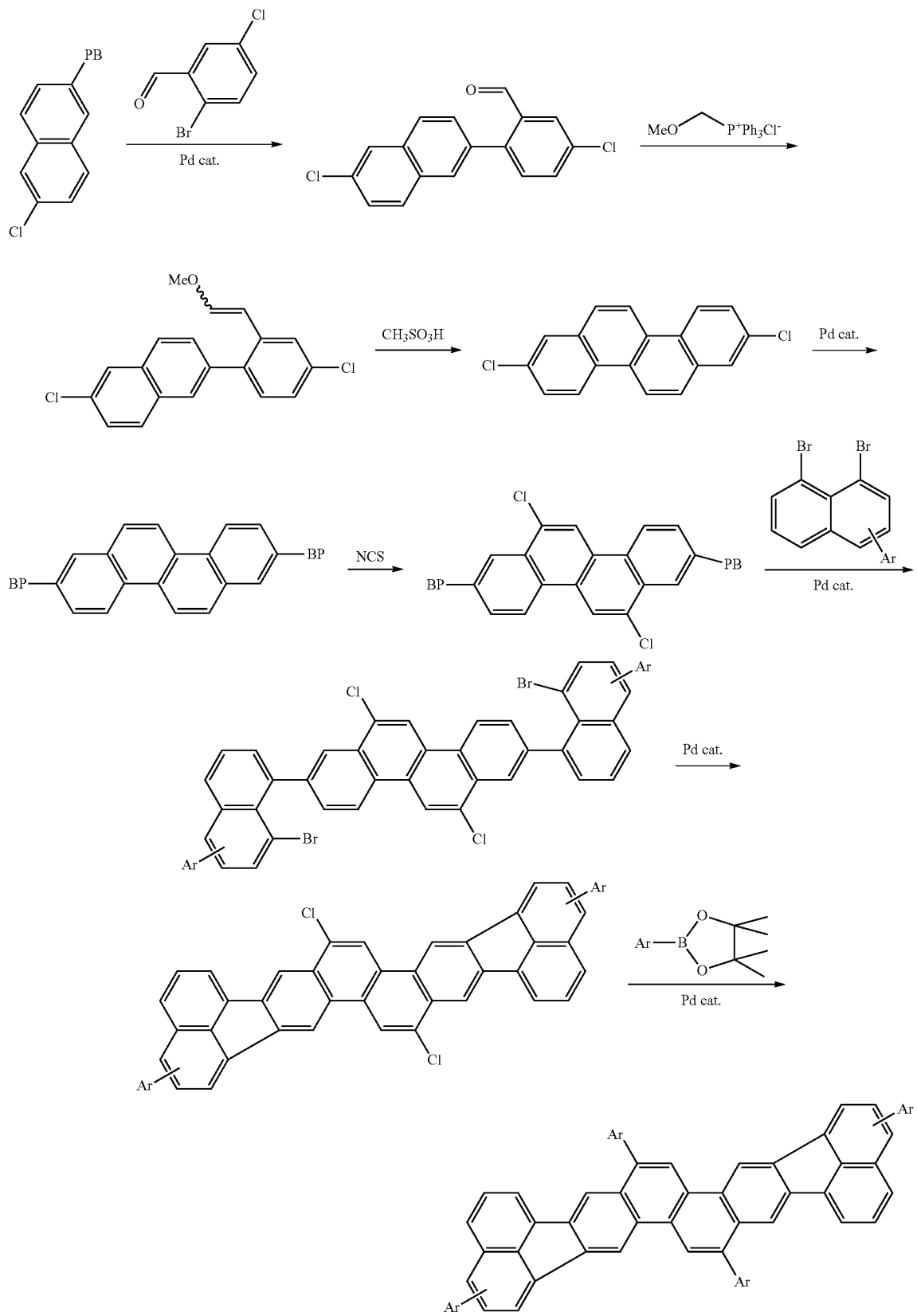
B-2

-continued
Synthesis route 3
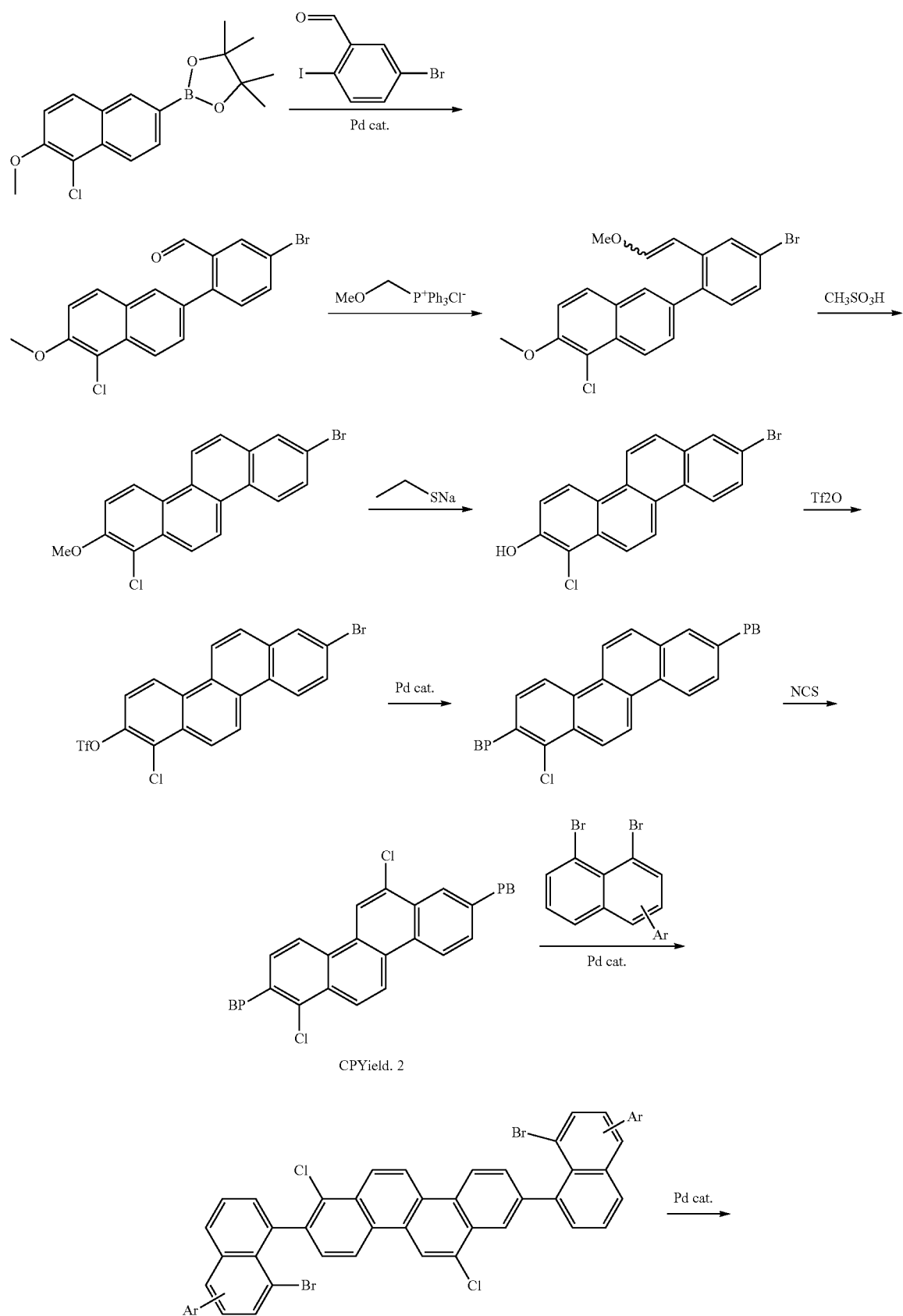

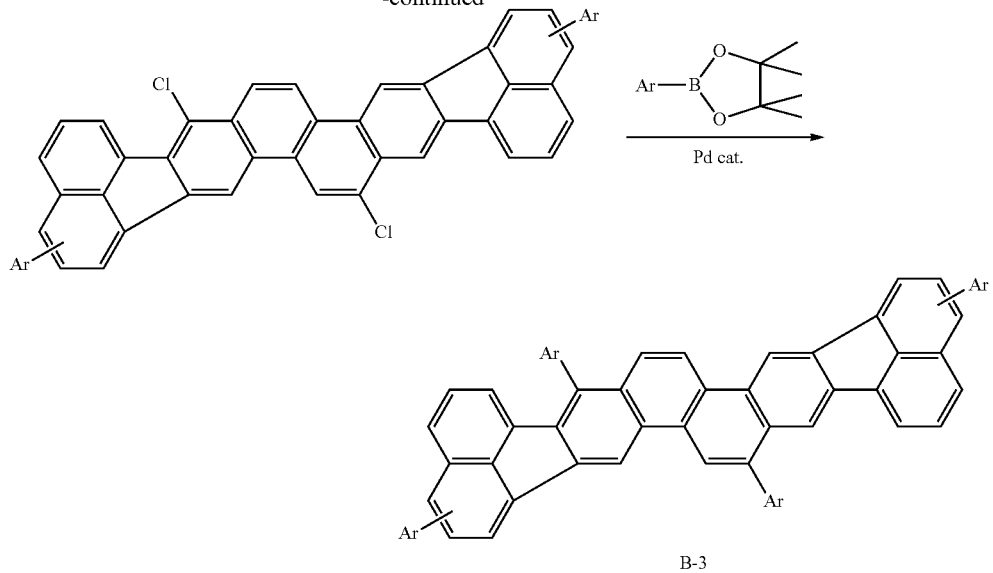

B-3

Herein, the organic compound represented by the formula (1) can be obtained by appropriately changing the substituent Ar. The details of the synthesis method will be described in Examples.

Next, an organic compound according to an embodiment of the present disclosure will be described.

When the organic compound represented by the formula (1) is made, the present inventors have focused on the basic skeleton itself. This is because light emitted from the basic skeleton is desirably in a blue region with a high color purity to obtain a blue light-emitting material with a high color purity. That is, the basic skeleton of the organic compound represented by the formula (1) is a skeleton suitable for emitting blue light with a high color purity. The present inventors have concluded the organic compound represented by the formula (1) in which the aryl group having at least one cyano group or the heterocyclic group having at least one cyano group is introduced to the basic skeleton.

Since the organic compound according to an embodiment of the present disclosure has the aryl group having at least one cyano group or the heterocyclic group having at least one cyano group on its basic skeleton with a high color purity, blue light having a higher color purity than light emitted from the basic skeleton itself is emitted.

In this specification, the blue region with a high color purity refers to a region in which the maximum emission wavelength is 430 nm or more and 445 nm or less in a dilute solution. The blue light with a high color purity may have a y coordinate of 0.10 or less on the CIE color coordinates.

Since the organic compound according to an embodiment of the present disclosure has the aryl group having at least one cyano group or the heterocyclic group having at least one cyano group on its basic skeleton, the organic compound has higher electron acceptability than the basic skeleton itself. The number of aryl groups having at least one cyano group or heterocyclic groups having at least one cyano group may be 1 to 4. The number of aryl groups having at least one cyano group or heterocyclic groups having at least one cyano group may be 1 or 2.

Organic compounds having high electron acceptability are compounds having high oxidation stability. In particular, organic light-emitting materials are required to have high oxidation stability. This is because an organic compound is repeatedly oxidized and reduced in an organic compound layer of an organic light-emitting element, thereby causing charge transfer and recombination. The compound that is unstable in terms of oxidation and reduction, that is, charge transfer is chemically changed to a different compound through an oxidation-reduction process and in an excited state. This impairs the intrinsic element characteristics, which decreases the luminance of the organic light-emitting element and decreases the life of the element. To suppress such deterioration, oxidation stability is required. One factor for achieving high oxidation stability is high electron acceptability.

Accordingly, the present inventors have focused on an increase in reduction potential as one of design strategies for materials having high electron acceptability, and have found the compound represented by the formula (1).

Specifically, the electron acceptability has been improved by introducing, to the basic skeleton, the aryl group having at least one cyano group or the heterocyclic group having at least one cyano group as an electron withdrawing substituent.

The electron withdrawing group is, for example, a halogen group such as a fluorine atom. However, such a halogen group has higher oxidation power than other electron withdrawing groups and thus readily affects other organic compounds constituting the organic light-emitting element. This may decrease the life of the element. The electron withdrawing group may be a carboxy group. When a carboxy group is introduced, the thermal stability of the organic compound deteriorates. Therefore, the organic compound to which a carboxy group is introduced may have difficulty in sublimation purification. If sublimation purification is not performed, it is difficult to increase the purity of the organic compound. The carboxy group is sometimes not suitable for materials of the organic light-emitting element. Accordingly, the present inventors have found a cyano group as an electron withdrawing substituent that does not impair thermal stability.

In Table 1 below, the organic compound represented by the formula (1) in which a cyano group is introduced to the basic skeleton as an electron withdrawing substituent and a comparative compound A that is different from the organic compound in the absence of a cyano group are compared with each other in terms of emission wavelength and reduction potential. The comparative compound A is an exemplary compound disclosed in PTL 1.

The emission wavelength was measured by photoluminescence measurement of a diluted toluene solution at an excitation wavelength of 350 nm at room temperature using an F-4500 manufactured by Hitachi, Ltd.

The reduction potential was determined by cyclic voltammetry (CV) measurement. The CV measurement was performed using a DMF solution of 0.1 M tetrabutylammonium perchlorate (for reduction potential measurement). The reference electrode was Ag/Ag$^+$, the counter electrode was Pt, and the working electrode was glassy carbon. The scanning speed of voltage was 1.0 V/s. The measurement instrument was an electrochemical analyzer 660C manufactured by ALS.

TABLE 1

| Name of compound | Molecular structure | Maximum emission wavelength (nm) | Reduction potential (V) |
| --- | --- | --- | --- |
| Comparative compound A | 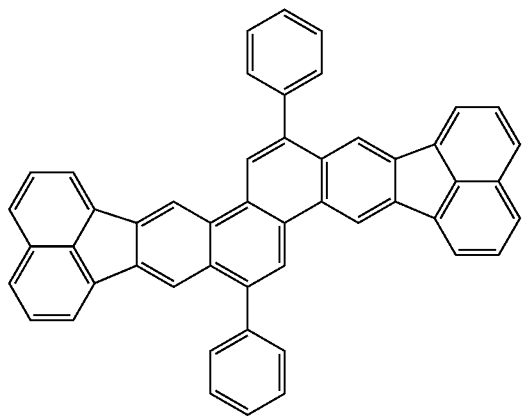 [SMILES: c1ccc(-c2cc3c4cc5c(cc4c(-c4ccccc4)cc3c3cc4c(cc23)-c2cccc3cccc-4c23)-c2cccc3cccc-5c23)cc1] | 448 | −2.1 |
| Embodiment compound D-3 | 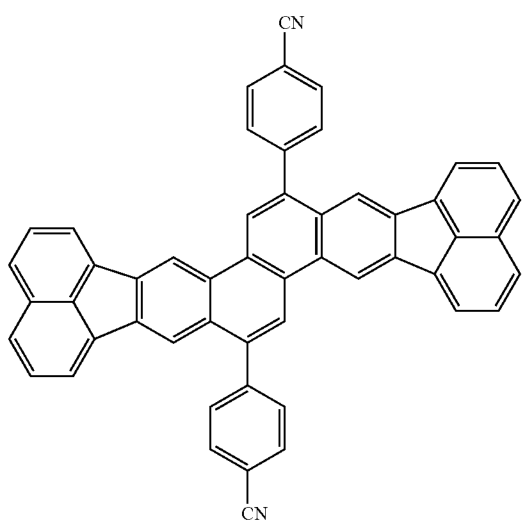 [SMILES: N#Cc1ccc(-c2cc3c4cc5c(cc4c(-c4ccc(C#N)cc4)cc3c3cc4c(cc23)-c2cccc3cccc-4c23)-c2cccc3cccc-5c23)cc1] | 444 | −2.0 |

TABLE 1-continued

| Name of compound | Molecular structure | Maximum emission wavelength (nm) | Reduction potential (V) |
|---|---|---|---|
| Embodiment compound E-5 | 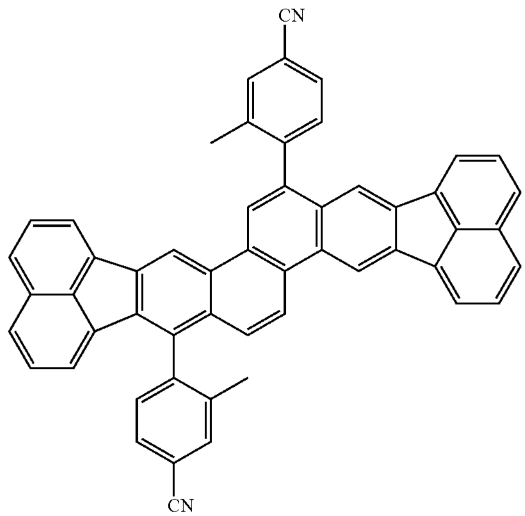 [SMILES: Cc1cc(C#N)ccc1-c1cc2c3cc4c(c(-c5ccc(C#N)cc5C)c3ccc2c2cc3c(cc12)-c1cccc2cccc-3c12)-c1cccc2cccc-4c12] | 441 | −2.0 |
| Embodiment compound D-34 | 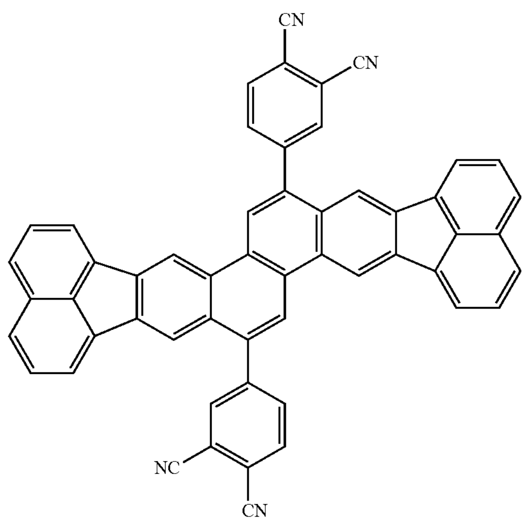 [SMILES: N#Cc1ccc(-c2cc3c4cc5c(cc4c(-c4ccc(C#N)c(C#N)c4)cc3c3cc4c(cc23)-c2cccc3cccc-4c23)-c2cccc3cccc-5c23)cc1C#N] | 442 | −1.9 |

Table 1 shows that the reduction potential of the compound according to this embodiment having a cyano group as an electron withdrawing substituent is higher than the comparative compound A by 0.1 eV or more. This indicates that the electron acceptability of the organic compound represented by the formula (1) is improved. Furthermore, the emission wavelength is shifted to shorter wavelengths by introducing a phenyl group having at least one cyano group, which is the aryl group having at least one cyano group.

As shown in Table 1, the blue purity is improved by introducing, to the basic skeleton, an aryl group having at least one cyano group or the heterocyclic group having at least one cyano group as an electron withdrawing substituent. This effect is considerably produced when an aryl group or the heterocyclic group having at least one cyano group is introduced to substitution positions indicated by arrows in the following structural formula. In other words, the blue purity is improved when the aryl group having at least one cyano group or the heterocyclic group having at least one cyano group is introduced to $R_7$, $R_8$, $R_9$, $R_{16}$, $R_{17}$, and $R_{18}$ in the organic compound represented by the formula (1).

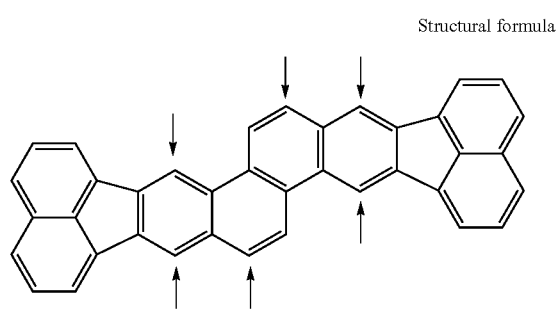 [SMILES: c1cc2c3c(cccc3c1)-c1cc3c(ccc4c5cc6c(cc5ccc34)-c3cccc4cccc-6c34)cc1-2]

Structural formula

For the substitution positions in the structural formula, the electron orbital distributions of HOMO and LUMO of the basic skeleton are compared with each other. The electron orbital distribution of LUMO is lower than the electron orbital distribution of HOMO. Therefore, a relatively large electron withdrawing effect is exerted to HOMO and the optical band gap is probably widened. The term "HOMO"

refers to the highest occupied molecular orbital, and "LUMO" refers to the lowest unoccupied molecular orbital.

To support the above consideration, the electron orbital distributions of HOMO and LUMO of the basic skeleton were calculated and illustrated using the molecular orbital calculations. FIG. 1 illustrates the results. The calculation results show that, at the substitution positions indicated by arrows in the above structural formula, the electron orbital distribution of LUMO is lower than that of HOMO and the orbital coefficient of LUMO is lower than that of HOMO.

The density functional theory (DFT), which has been widely used today, was used as a calculation technique of the molecular orbital calculations. The functional was B3LYP and the basis function was 6-31G*. The basis function is also referred to as 6-31G(d). The molecular orbital calculations were conducted by using Gaussian09 (Gaussian09, Revision C.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc., Wallingford Conn., 2010), which has been widely used today.

For the organic compound according to an embodiment of the present disclosure, the degree of intermolecular stacking can be decreased by introducing the aryl group having at least one cyano group or the heterocyclic group having at least one cyano group to $R_7$, $R_8$, $R_9$, $R_{16}$, $R_{17}$, and $R_{18}$ in the formula (1). By decreasing the degree of intermolecular stacking, the sublimability can be improved and the crystallinity can be reduced.

In this specification, the sublimability refers to a state in which the sublimation temperature of the organic compound is higher than the thermal decomposition temperature of the organic compound. The state in which the difference in temperature is large is referred to as high sublimability. The crystallinity refers to a state in which molecules keep an amorphous state at high entropy such as high temperature or application of an electric field. The property that keeps an amorphous state is referred to as low crystallinity.

The improvement in sublimability can decrease the number of molecules subjected to thermal decomposition during sublimation purification. By performing sublimation purification, the purity of the organic compound can be relatively easily improved. This can decrease the amount of impurities contained in the organic light-emitting element. Thus, a decrease in light emission efficiency due to impurities and a decrease in driving durability can be suppressed. By reducing the crystallinity, the concentration quenching can be reduced. The reduction in concentration quenching is suitable from the viewpoint of improving the light emission efficiency of the organic light-emitting element.

The basic skeleton plane of the organic compound represented by the formula (1) has a large ratio of long axis and short axis. Therefore, if the substituent is not introduced, the distance between basic skeleton planes is small in the form of thin film, which increases the intermolecular interaction. This may cause concentration quenching and decrease in sublimability. The organic compound represented by the formula (1) has high planarity in a portion in which four six-membered rings are fused. The portion in which four six-membered rings are fused is also referred to as a chrysene portion of the basic skeleton or a central portion of the molecule. Therefore, a substituent may be introduced near the center of the molecule, which has high molecular planarity, to decrease the intermolecular interaction, improve the sublimability, and reduce the concentration quenching. In other words, a substituent may be introduced to at least one of $R_7$, $R_8$, $R_9$, $R_{16}$, $R_{17}$, and $R_{18}$ in the organic compound represented by the formula (1).

The basic skeleton of the organic compound according to an embodiment of the present disclosure is constituted by only a hydrocarbon. Therefore, the organic compound has a chemically stable skeleton with high bond energy. To maintain high bond energy of the whole organic compound, a substituent to be introduced to the basic skeleton may be a substituent with high bond energy. For example, if a compound having low bond energy such as a compound having an amino group is used as light-emitting materials for the organic light-emitting element, the compound is easily deteriorated during driving of the element, which may decrease the durability life of the organic light-emitting element.

With reference to the following compounds A-1, A-2, and B-1, the bond having low bond stability is a bond between a carbazole ring and a phenylene group and a bond between an amino group and a phenyl group (nitrogen-carbon bond). The carbon-carbon bond in the compound B-1 has higher bond stability.

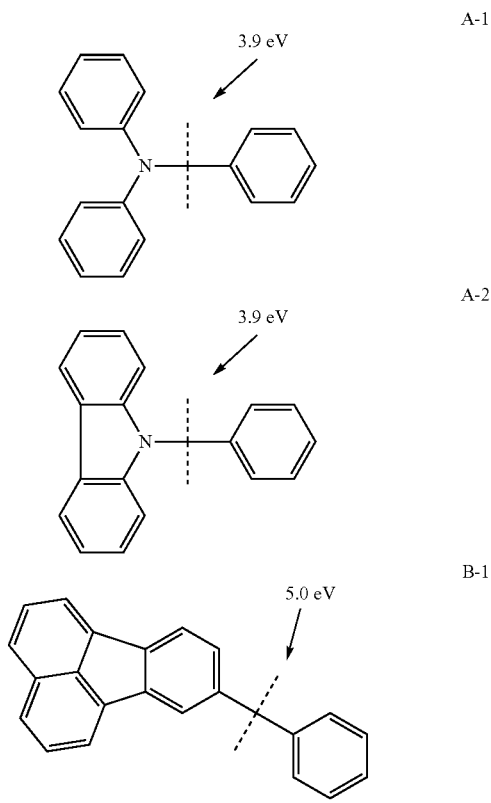

As described above, the organic compound according to an embodiment of the present disclosure can emit blue light with a higher color purity than the comparative compound. The organic compound is a chemically stable compound because of its high reduction potential.
The organic compound according to an embodiment of the present disclosure will be specifically described below. However, the present disclosure is not limited thereto.
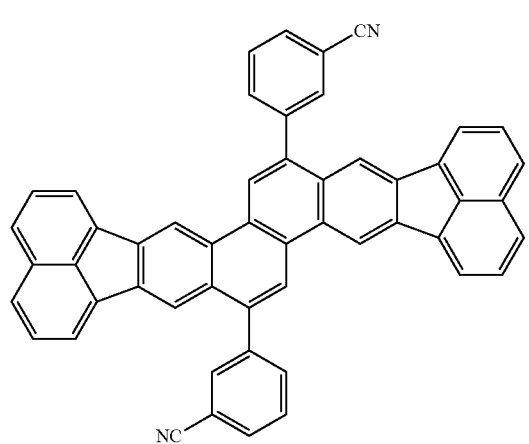
D-1
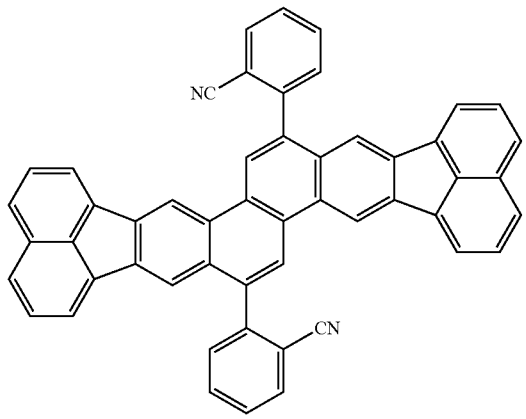
D-2
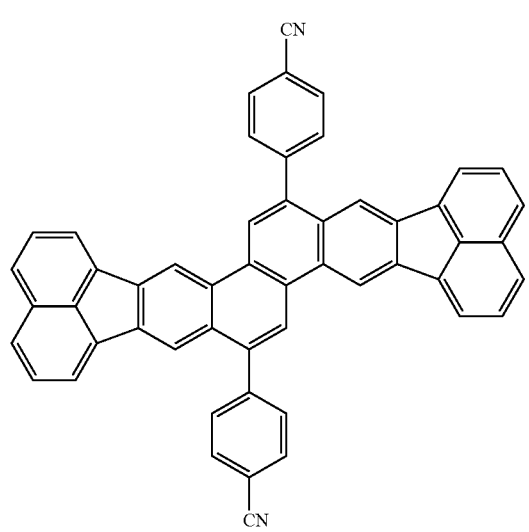
D-3
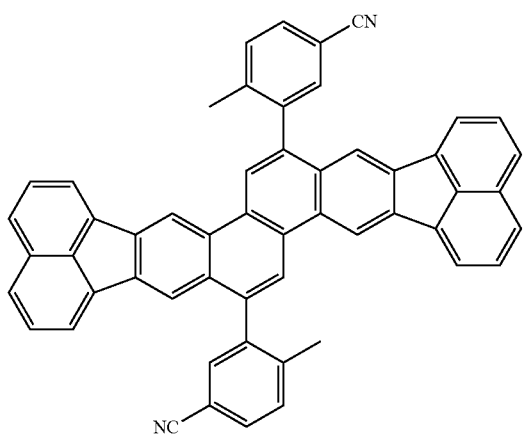
D-4
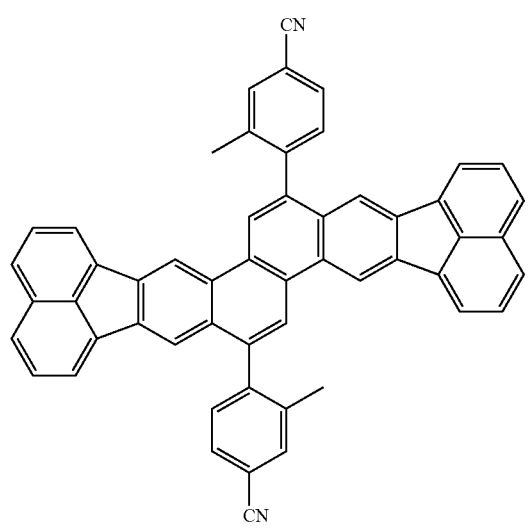
D-5
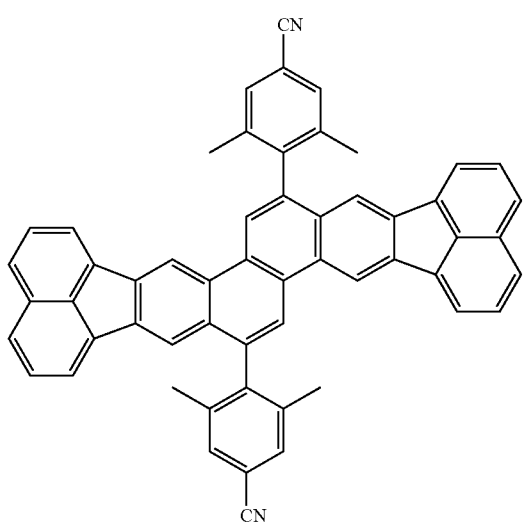
D-6

-continued
D-7
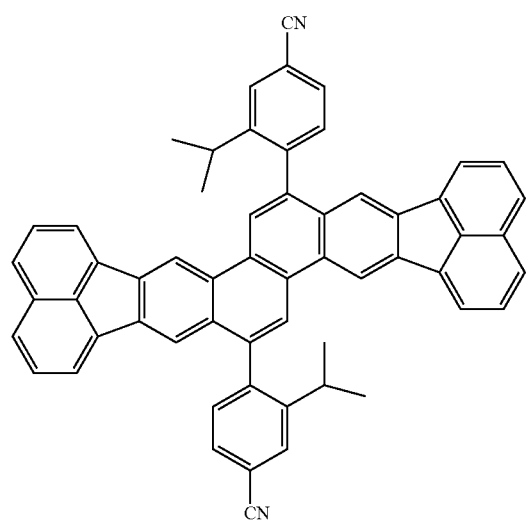
D-8
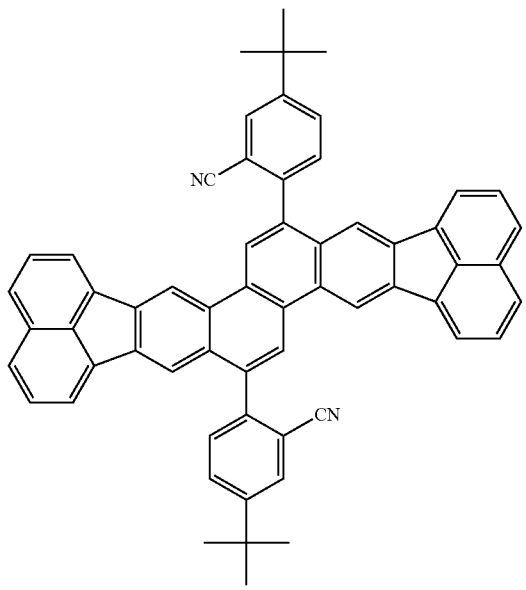
D-9
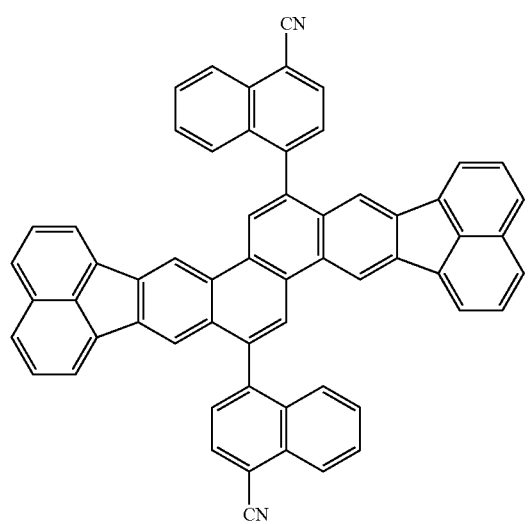
D-10
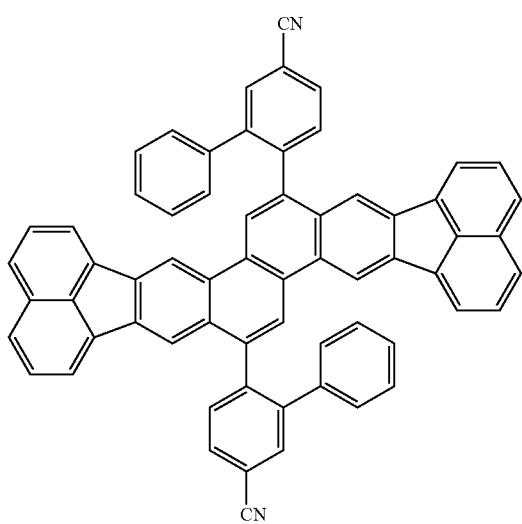
D-11
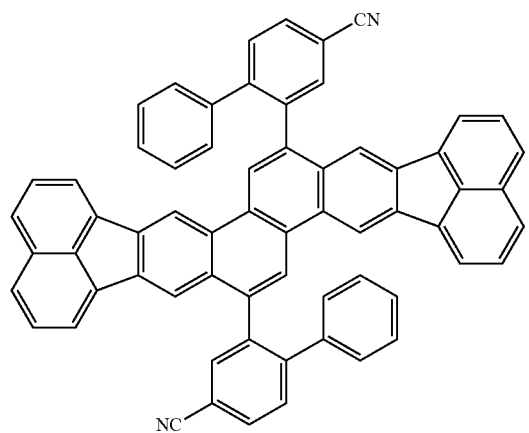
D-12
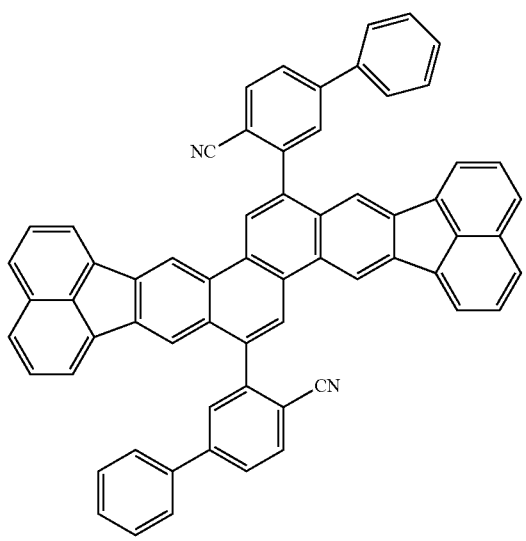

-continued
D-13
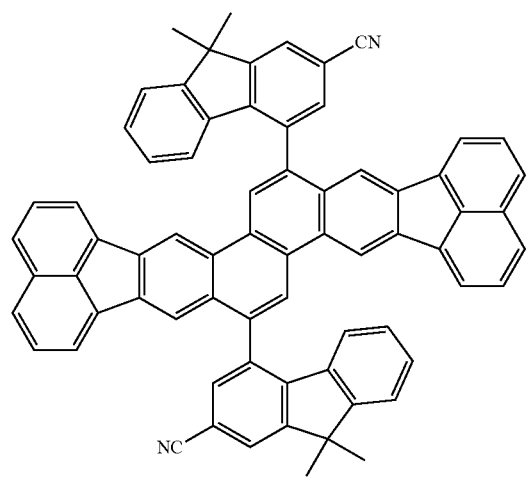
D-14
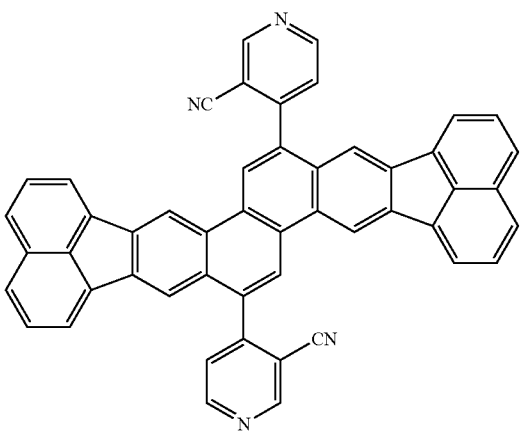
D-15
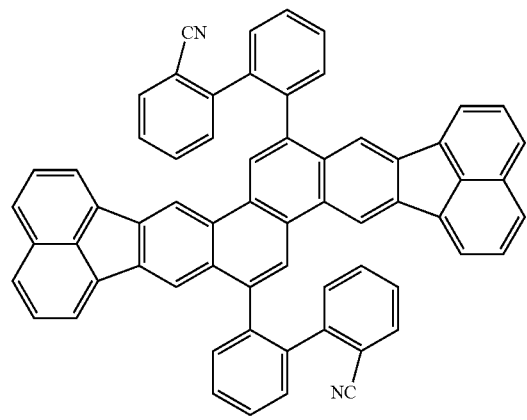
D-16
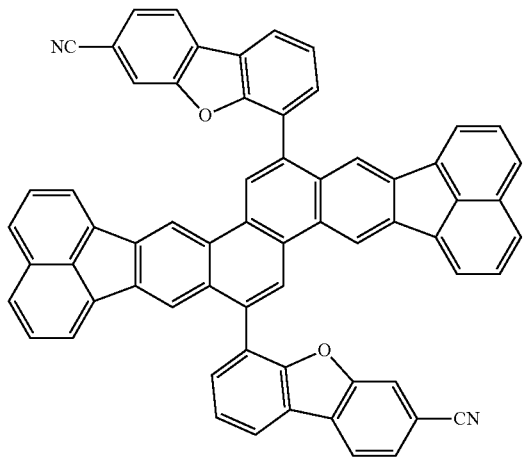
D-17
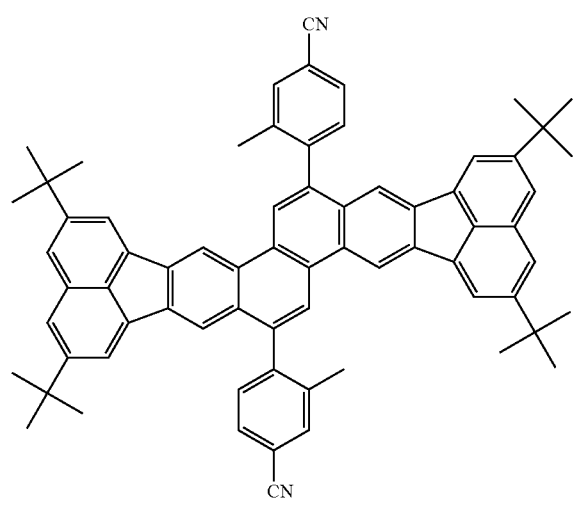
D-18
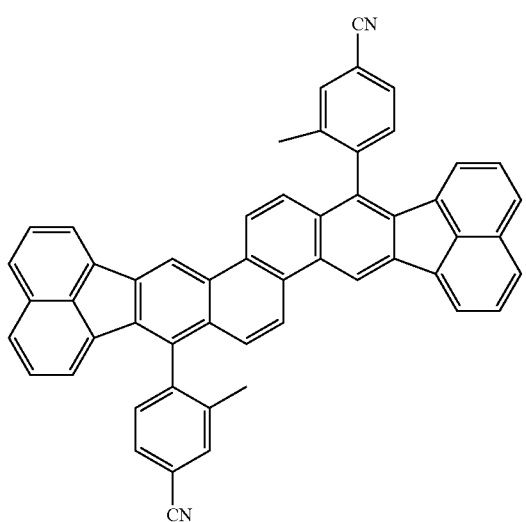

-continued
D-19
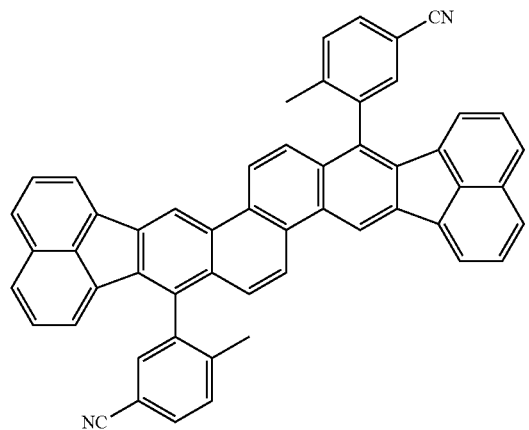
D-20
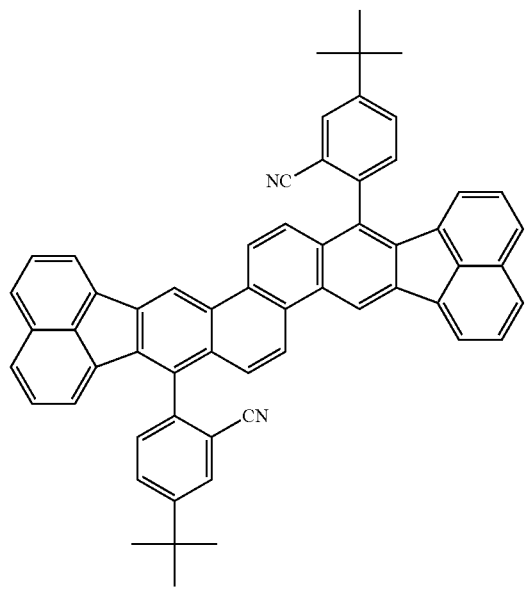
D-21
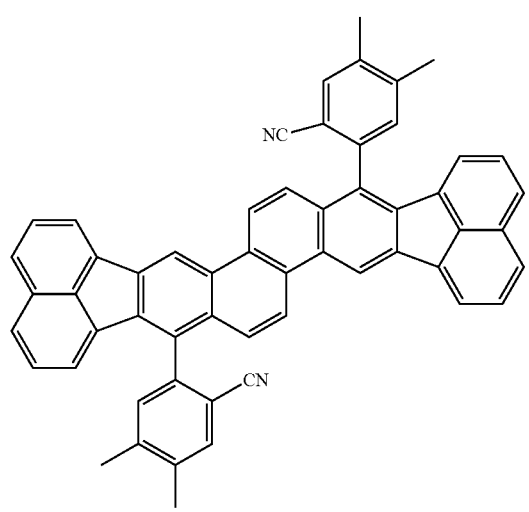
D-22
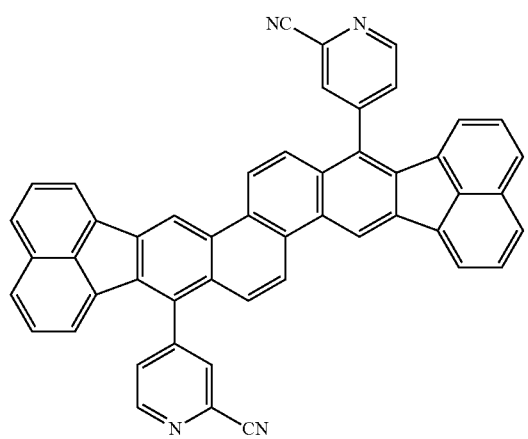
D-23
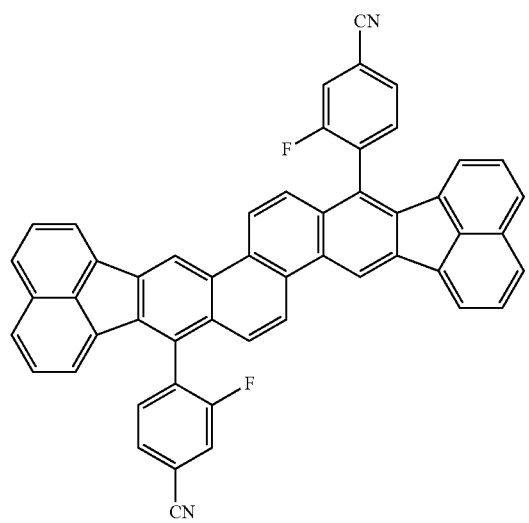
D-24
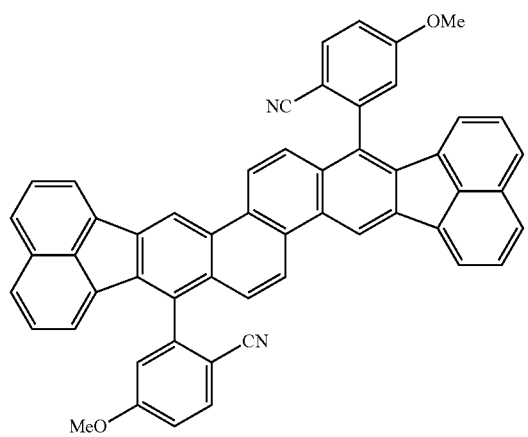

-continued
D-25
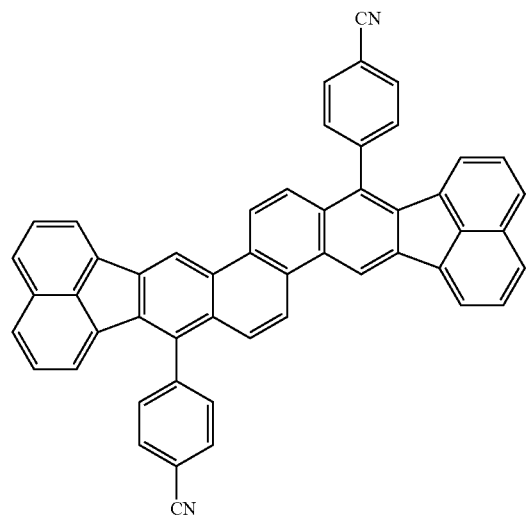
D-26
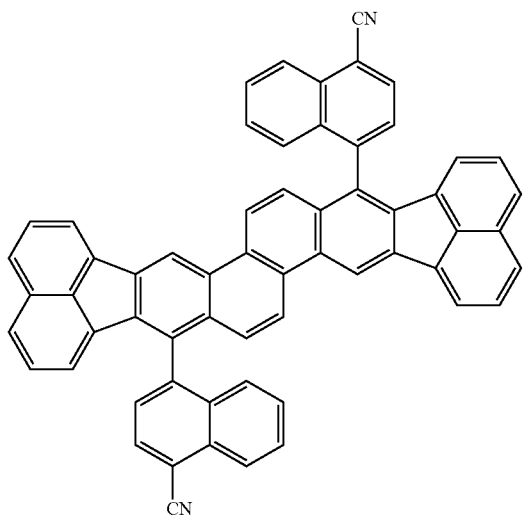
D-27
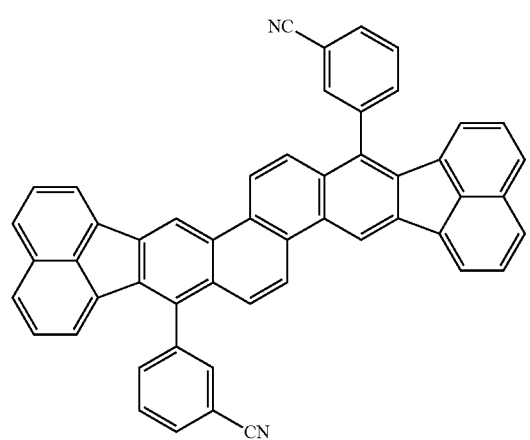
D-28
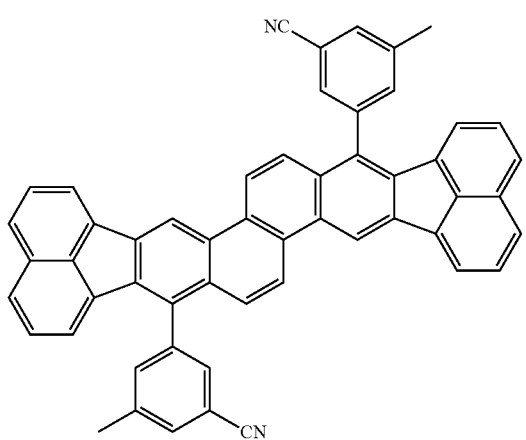
D-29
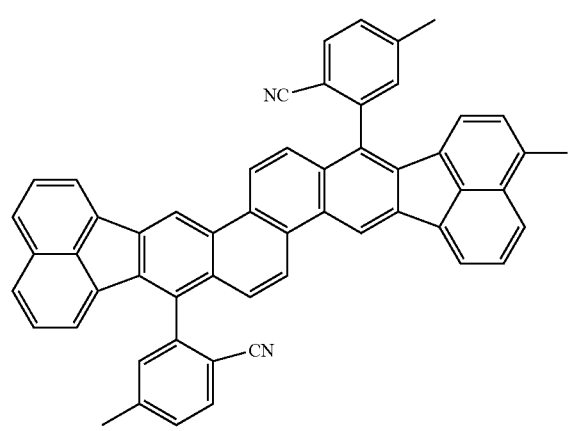
D-30
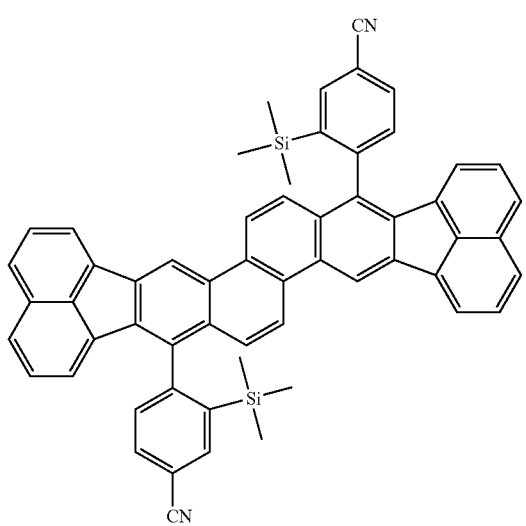

-continued
D-31
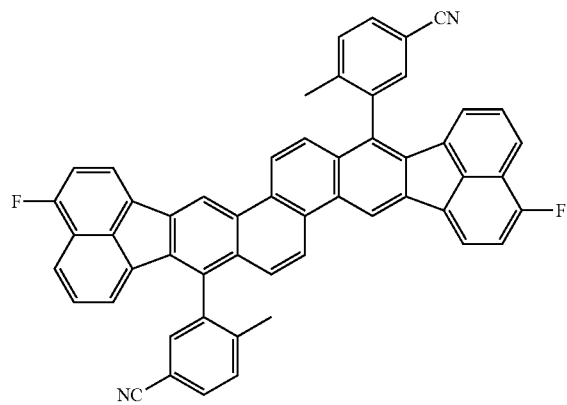
D-32
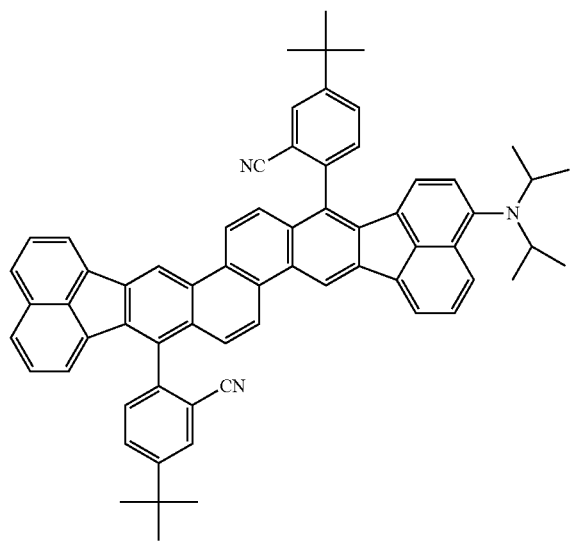
D-33
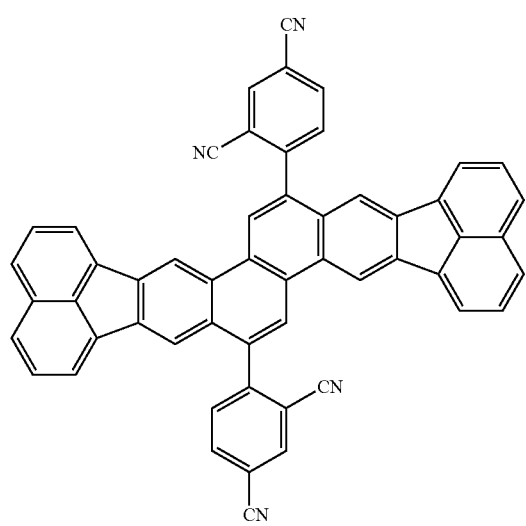
D-34
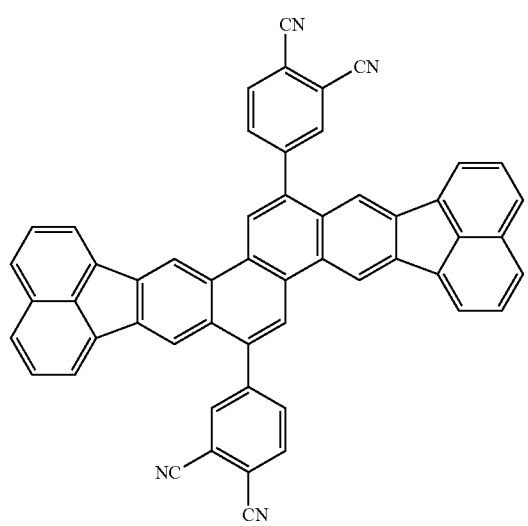
D-35
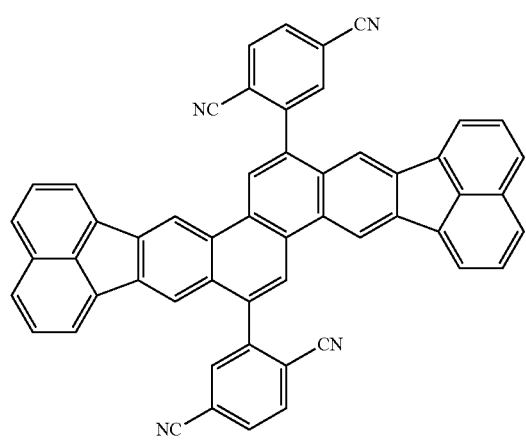
D-36
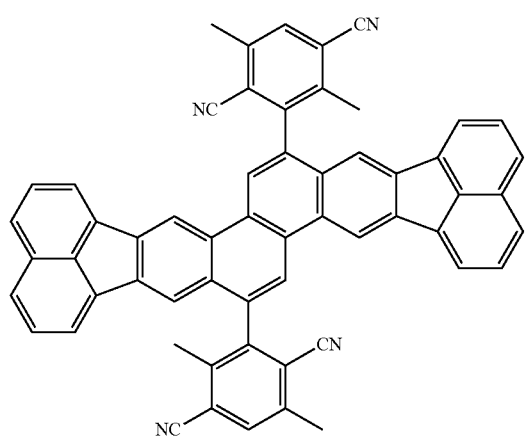

-continued
D-37
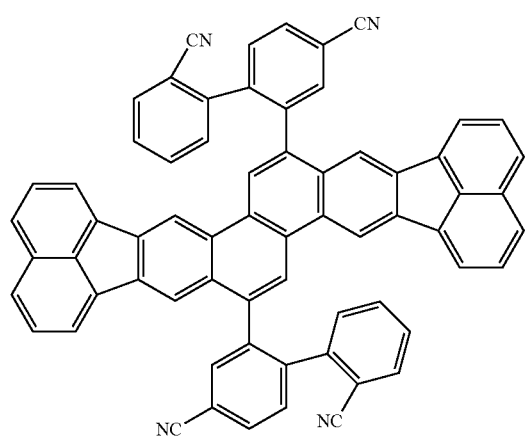
D-38
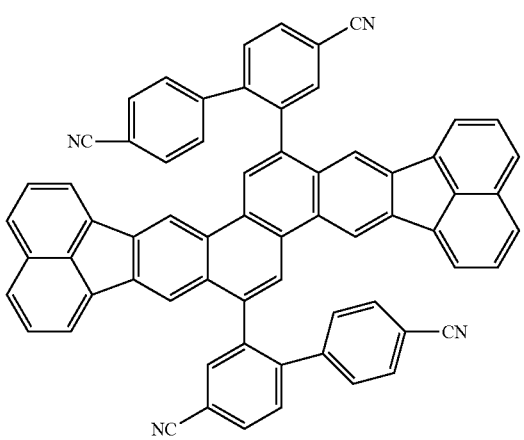
D-39
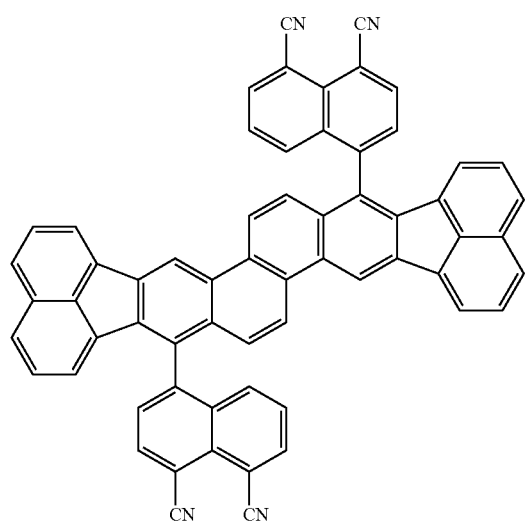
D-40
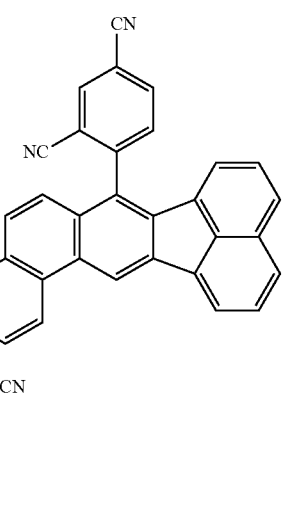
D-41
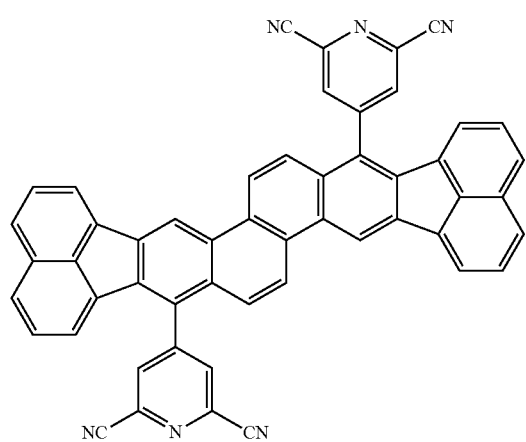
D-42
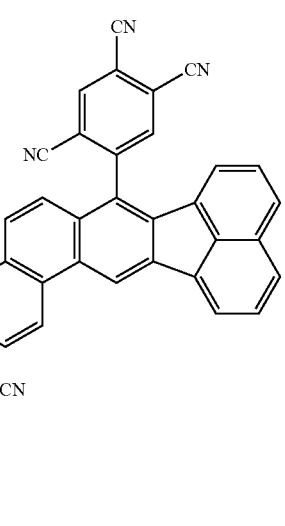

-continued
D-43
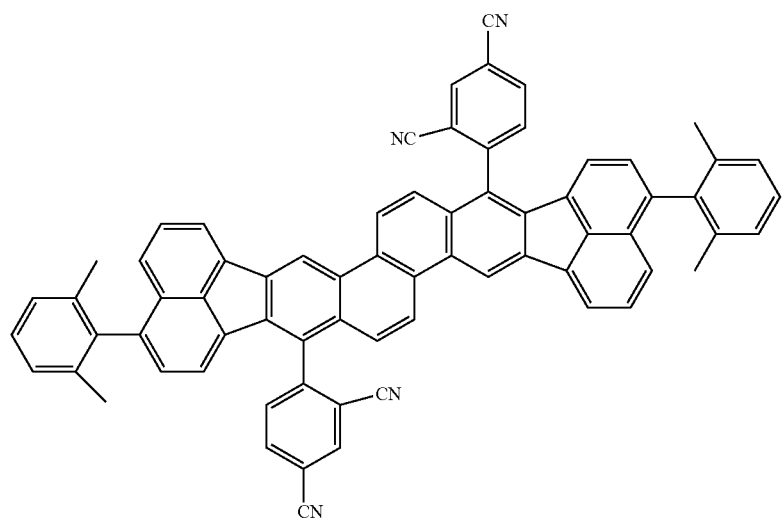
D-44
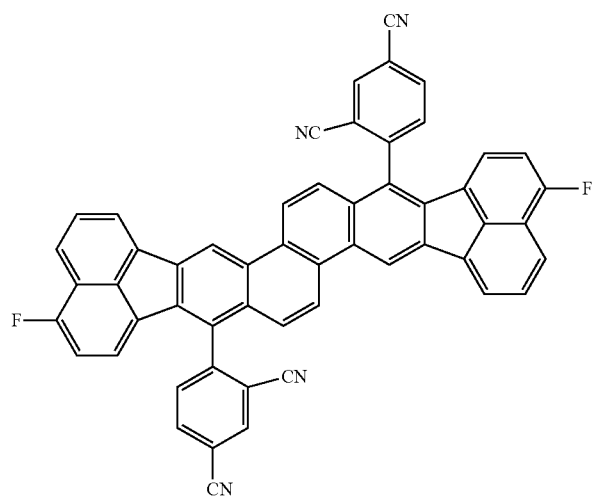
D-45
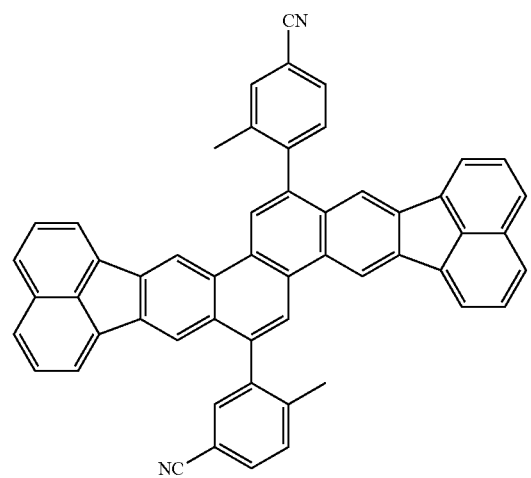
D-46
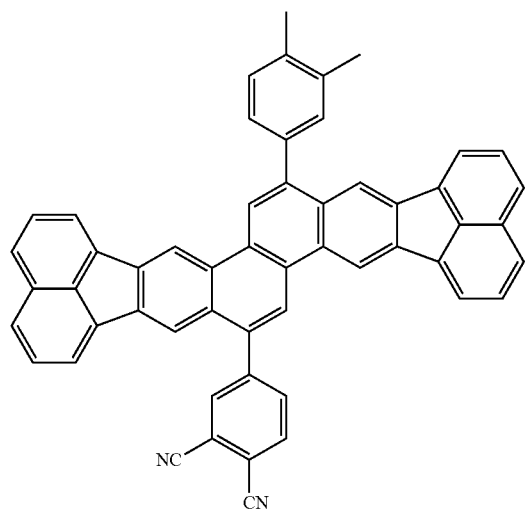
D-47
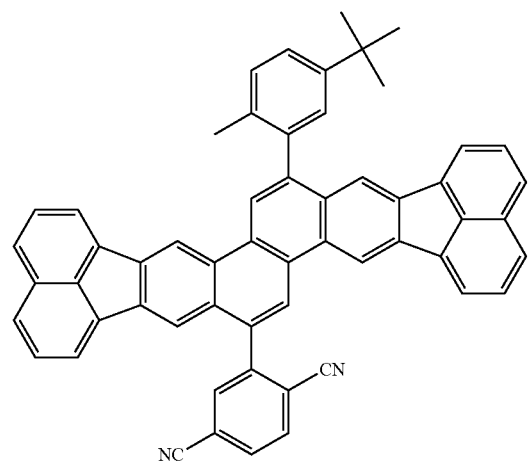

D-48
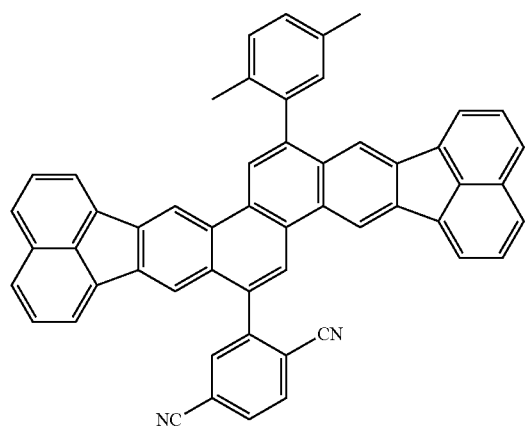
D-49
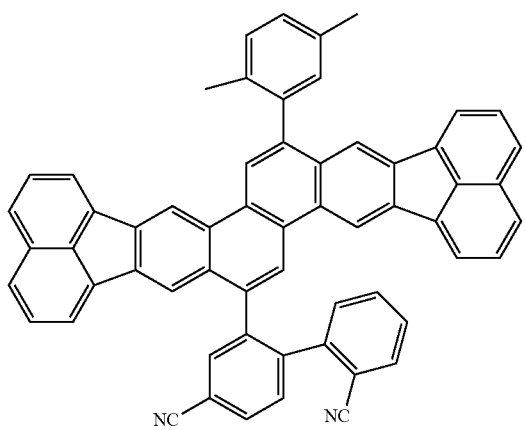
D-50
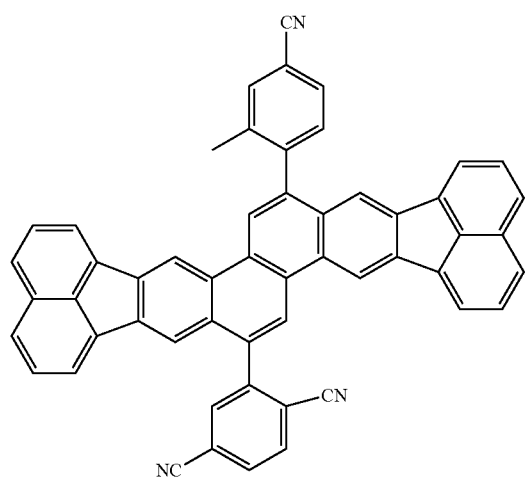
D-51
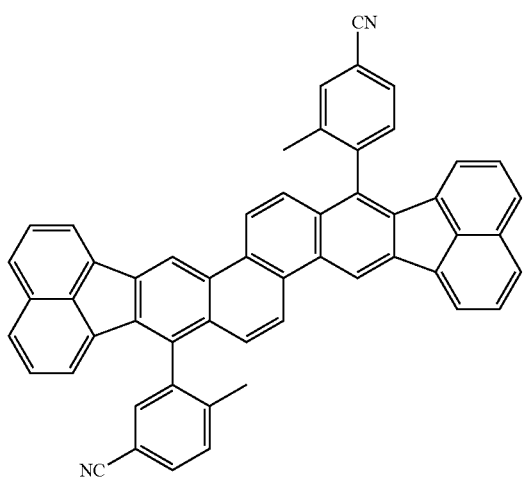
D-52
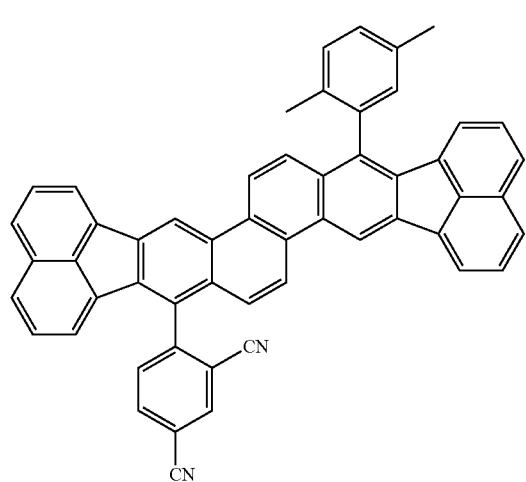
D-53
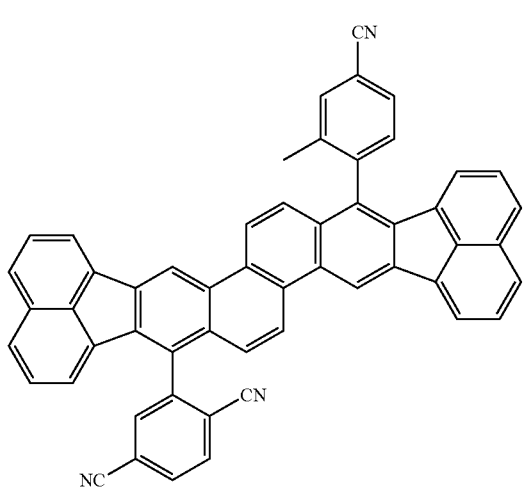

-continued
D-54
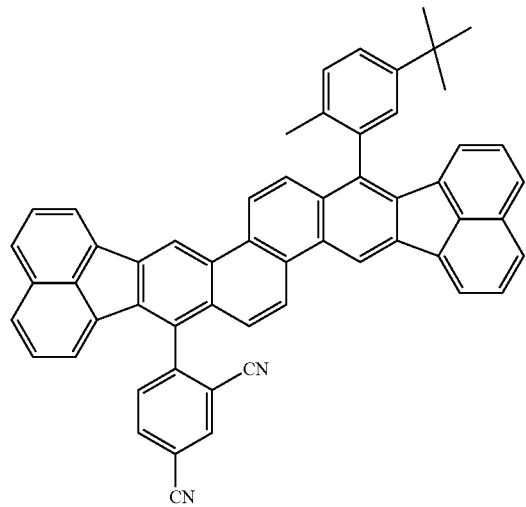
D-55
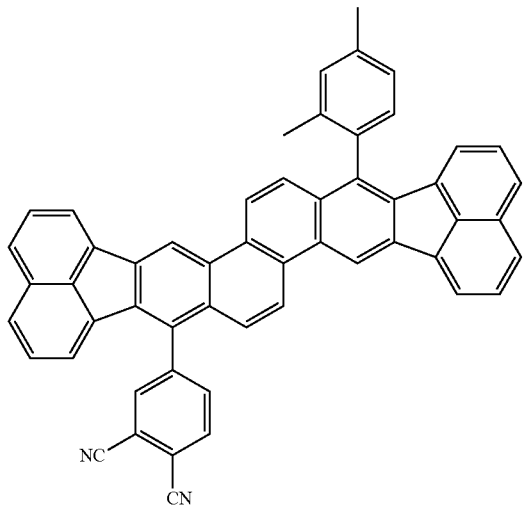
D-56
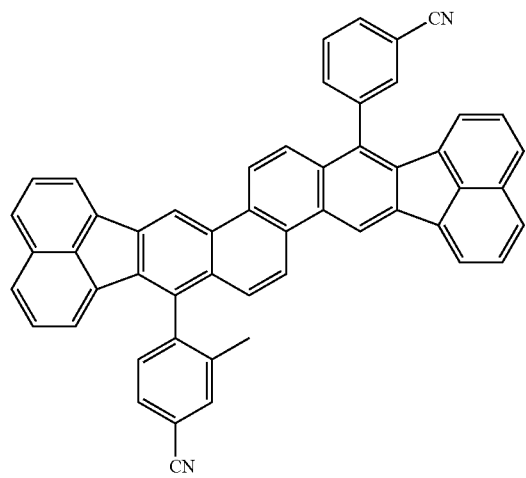
D-57
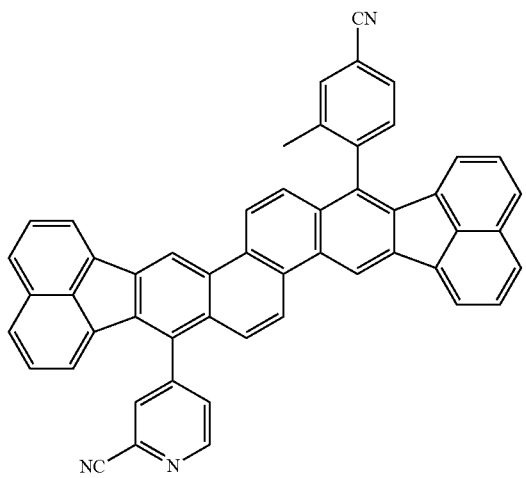
D-58
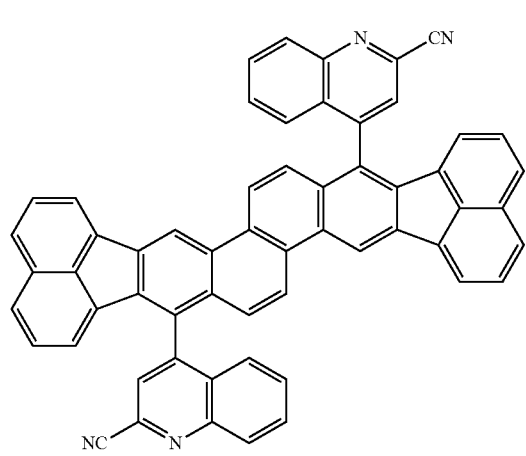
D-59
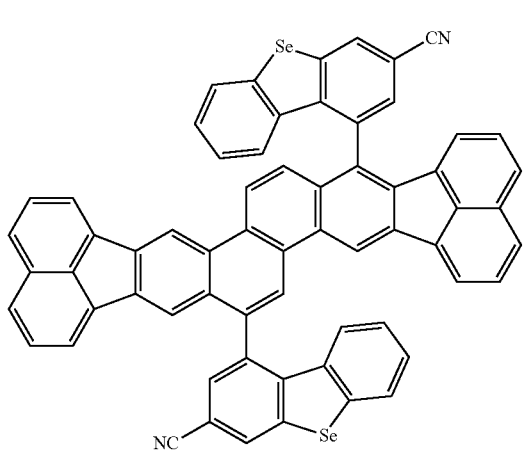

-continued
D-60
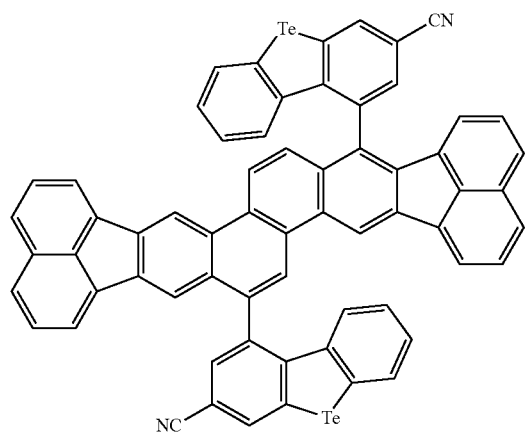
E-1
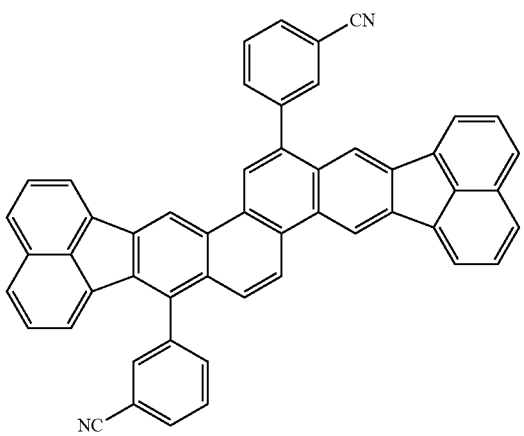
E-2
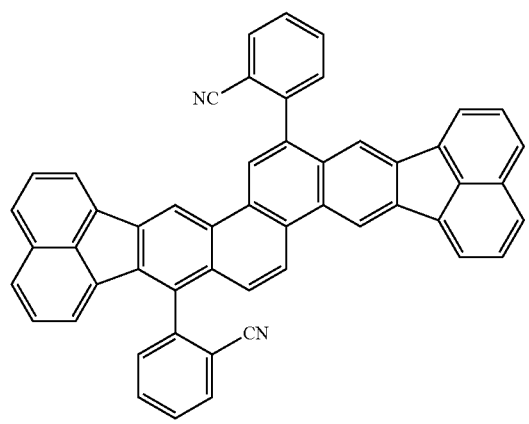
E-3
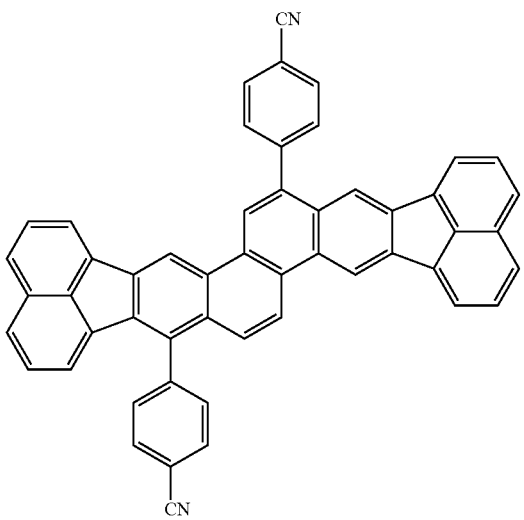
E-4
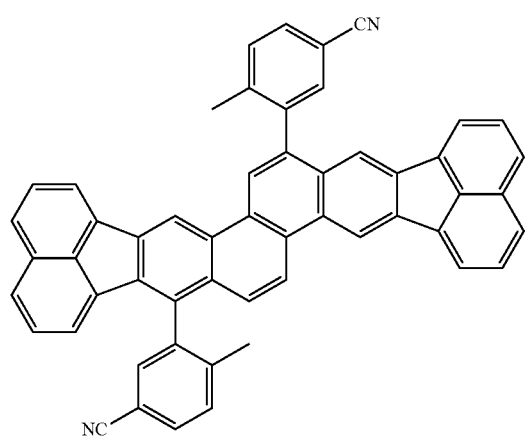
E-5
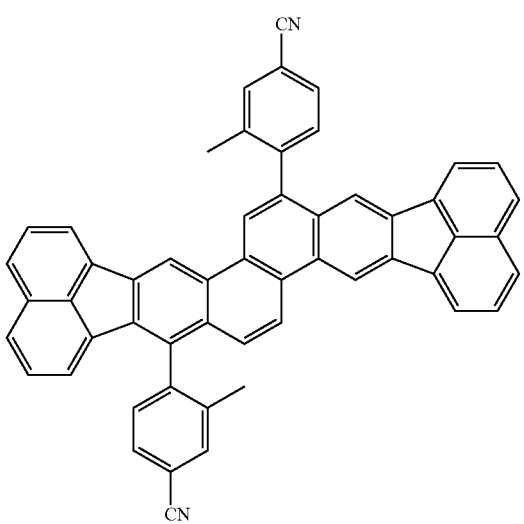

-continued
E-6
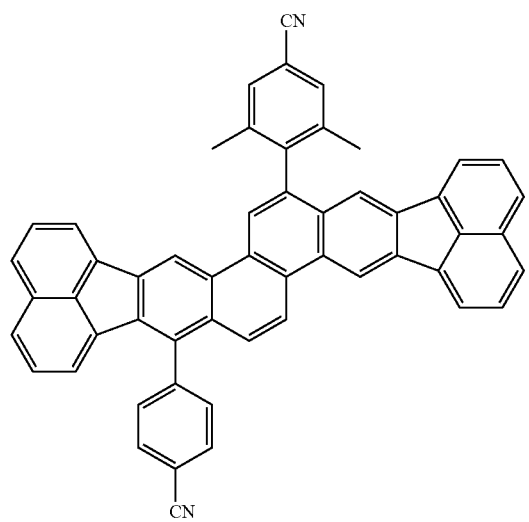
E-7
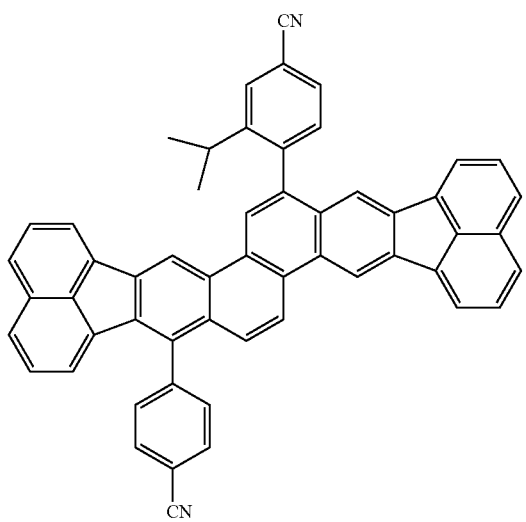
E-8
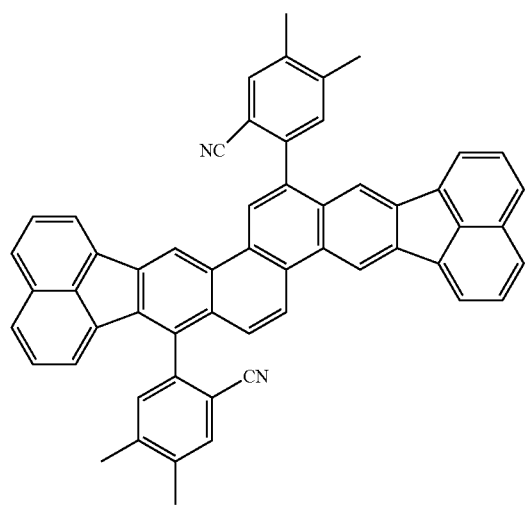
E-9
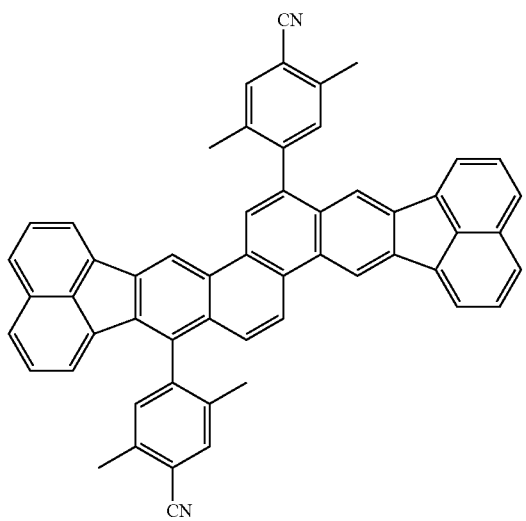
E-10
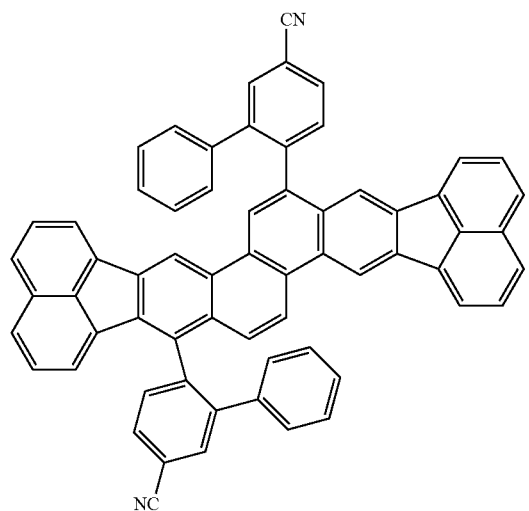
E-11
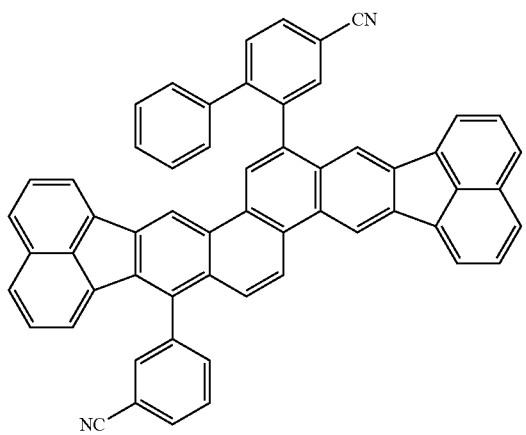

-continued
E-12
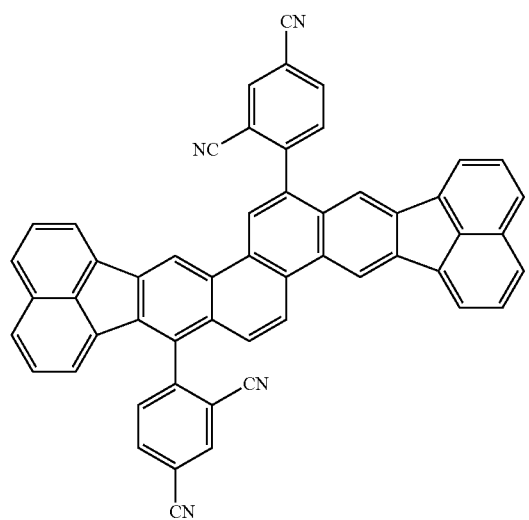
E-13
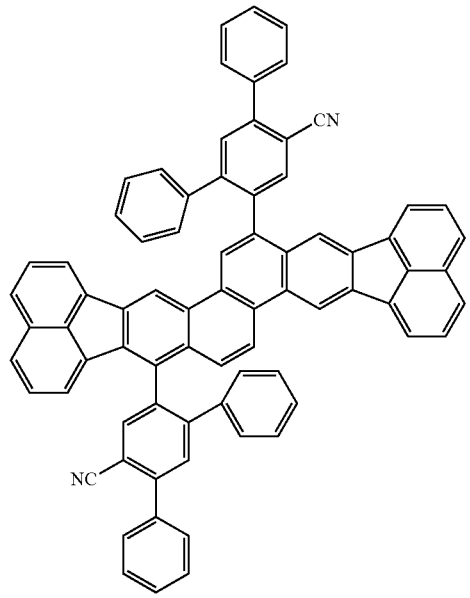
E-14
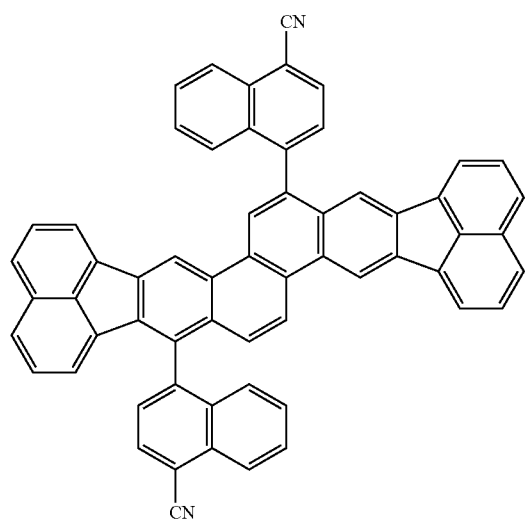
E-15
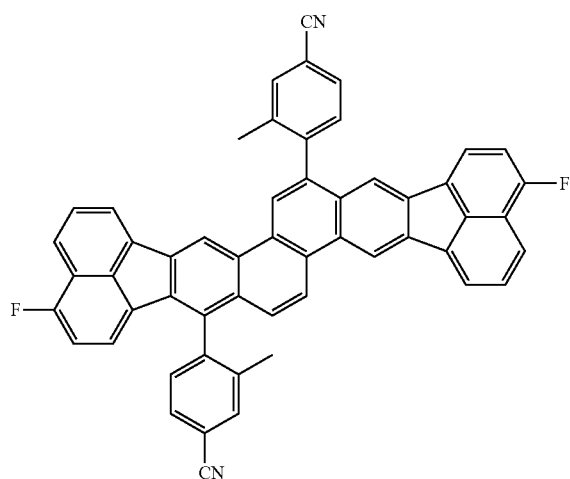
E-16
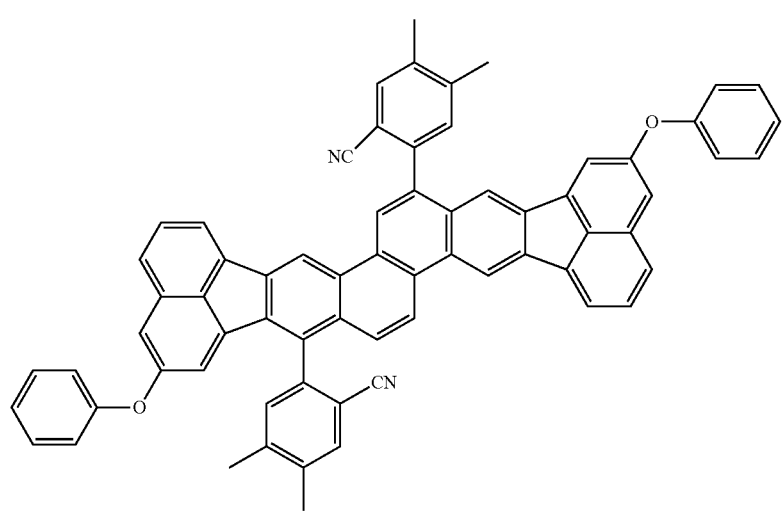

-continued
E-17
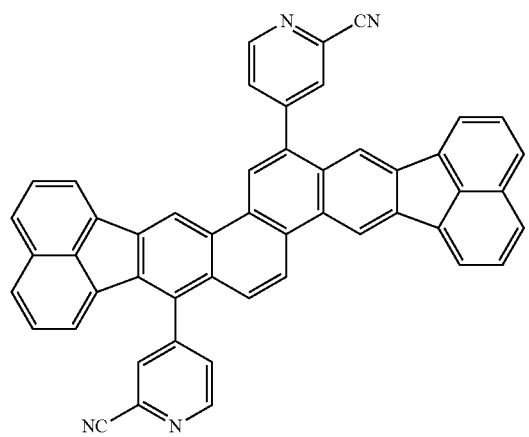
E-18
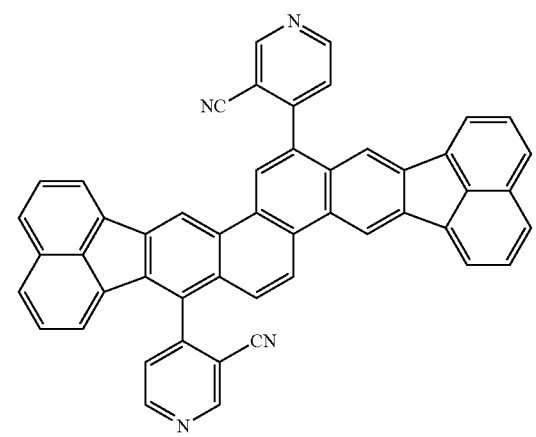
E-19
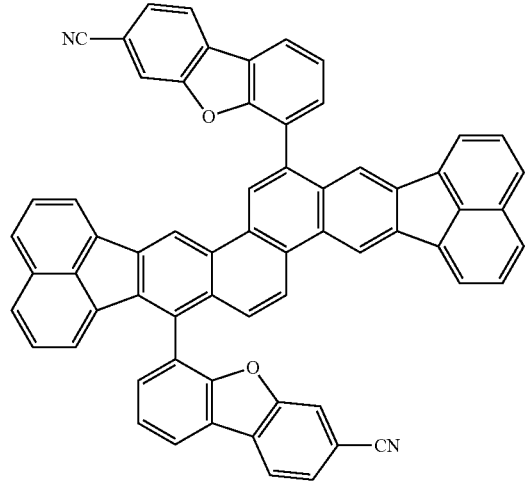
E-20
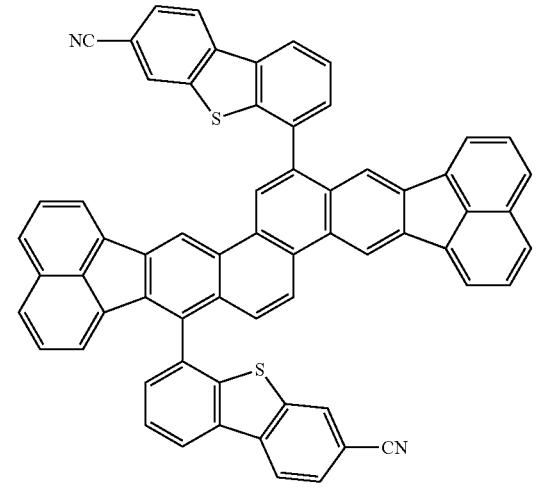
E-21
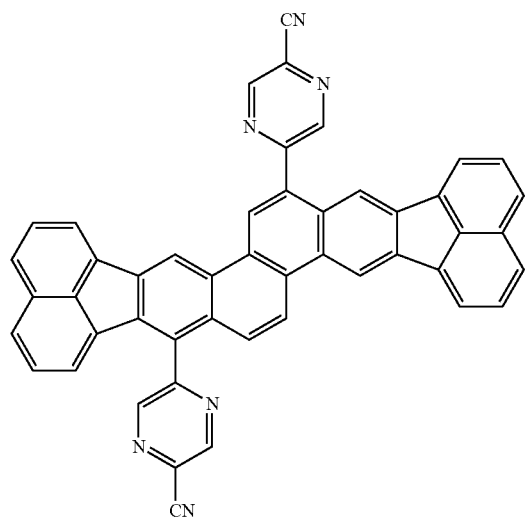
E-22
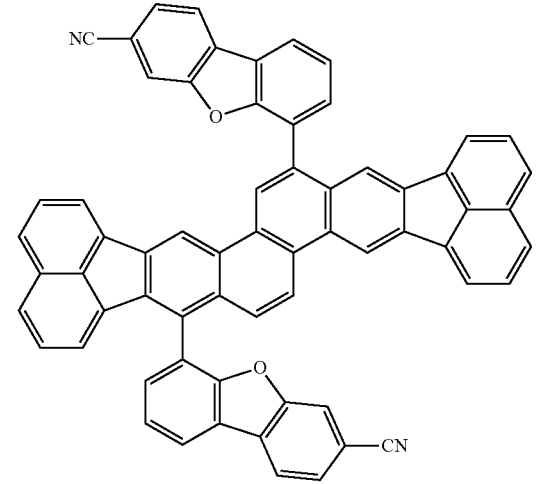

-continued
E-23
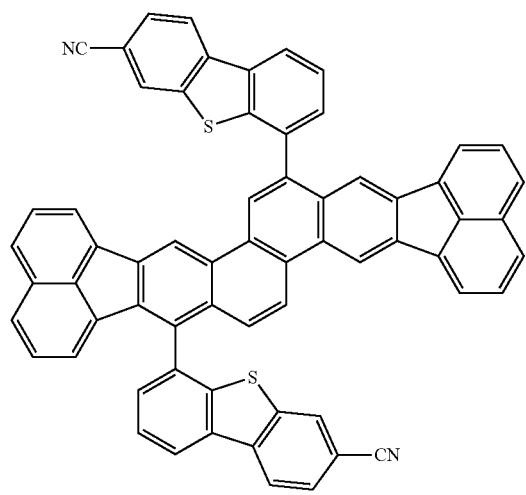
E-24
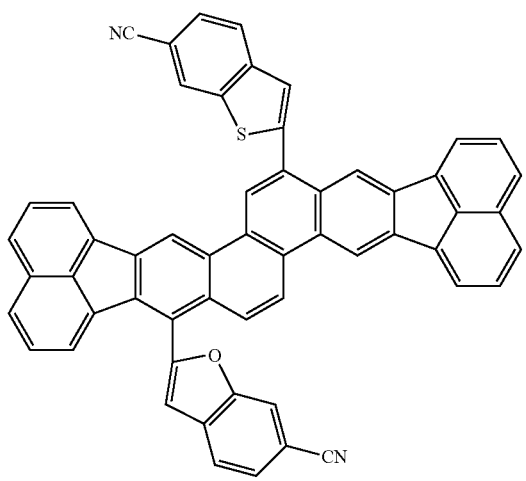
E-25
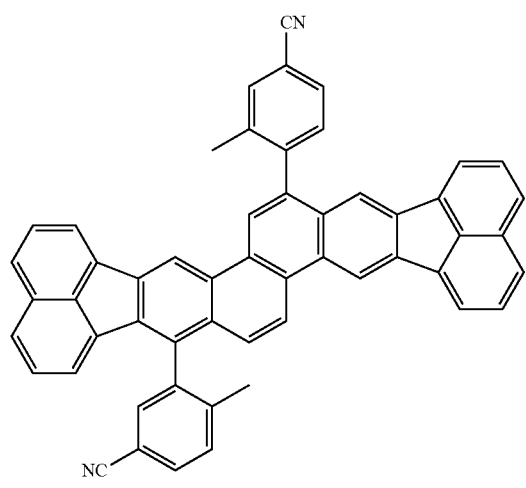
E-26
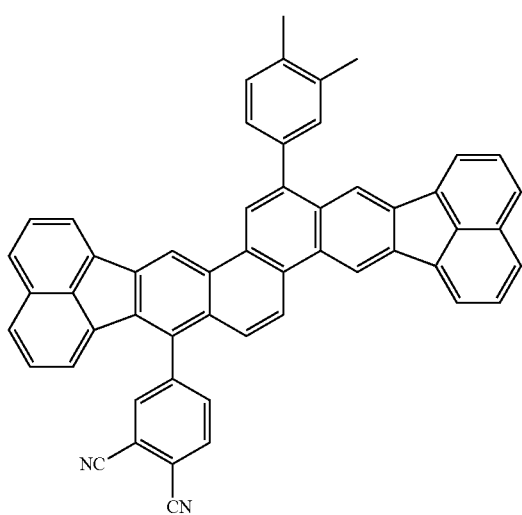
E-27
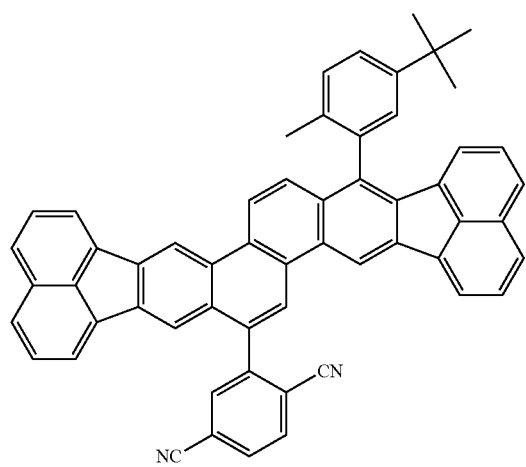
E-28
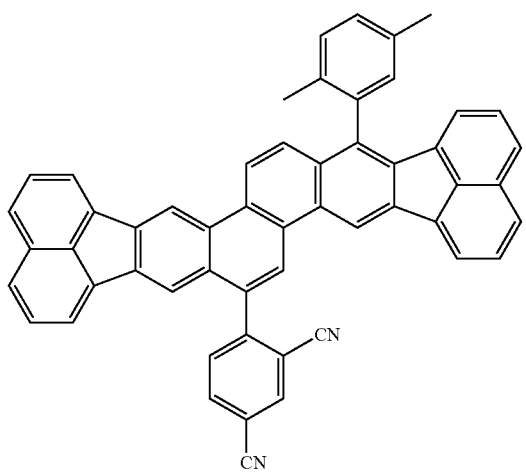

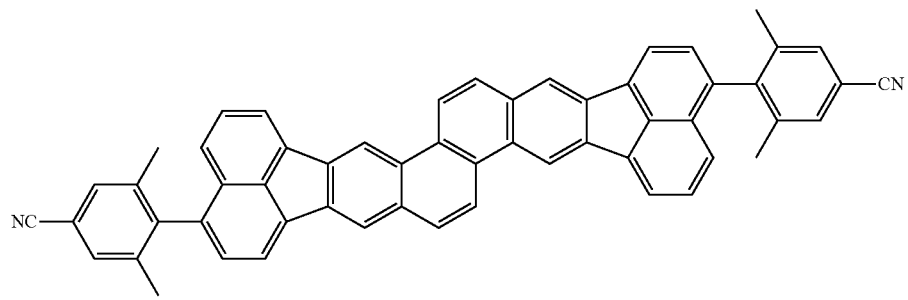
F-1
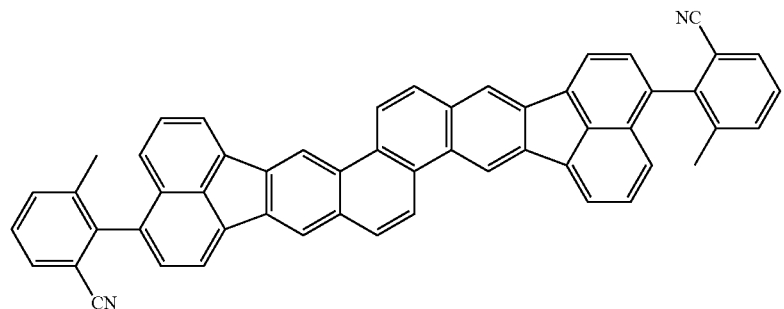
F-2
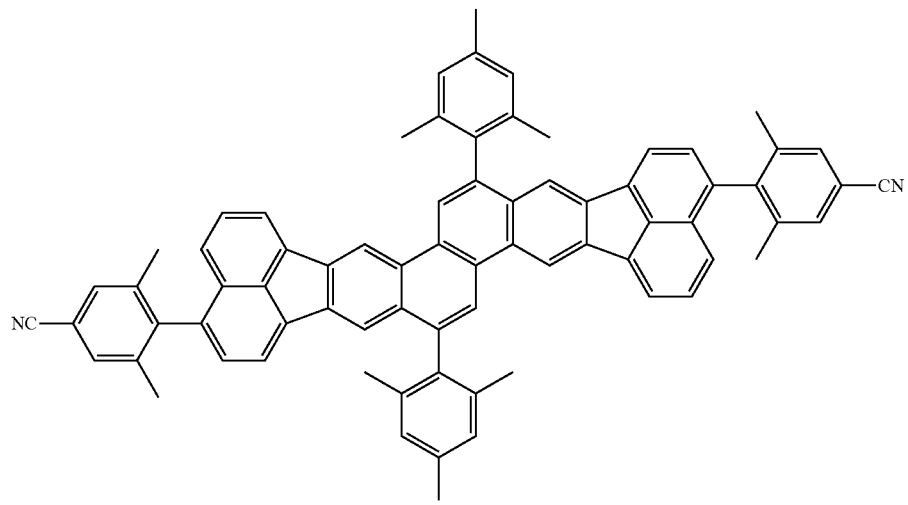
F-3
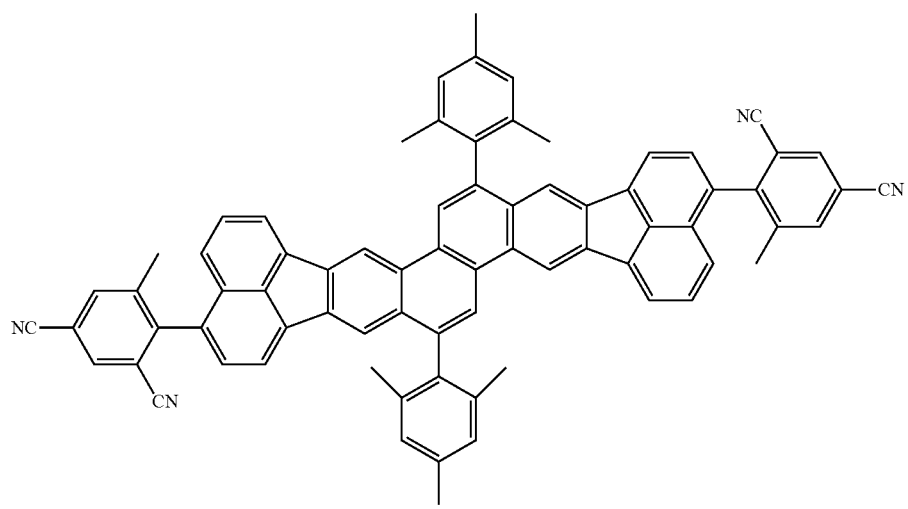
F-4

F-5
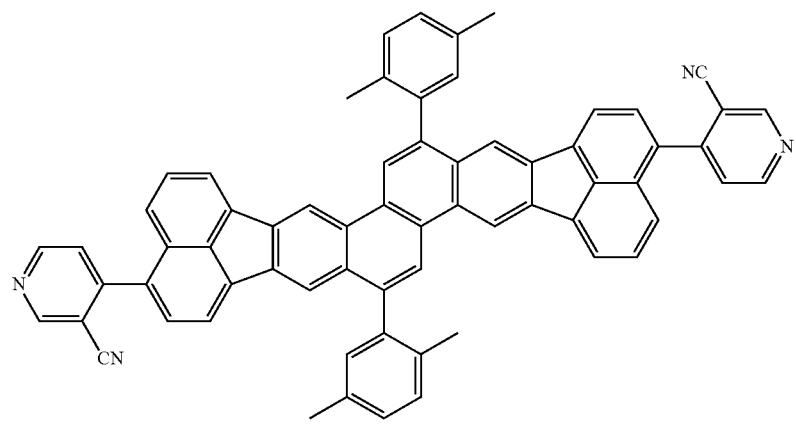
F-6
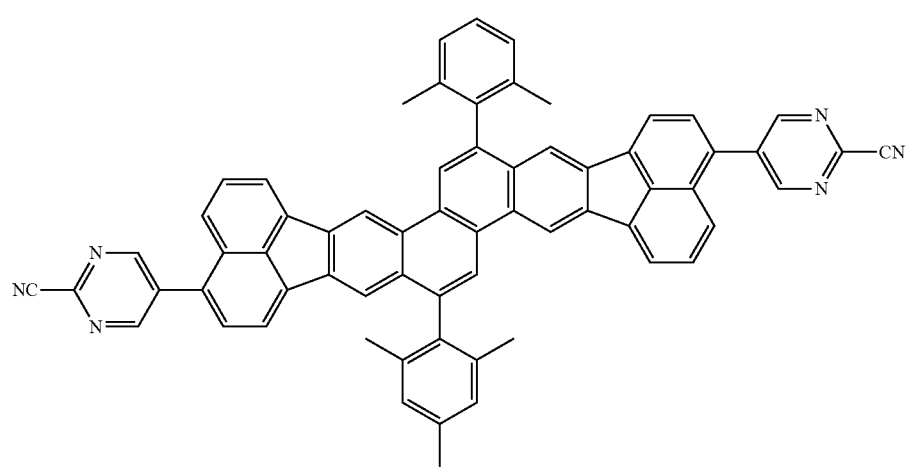
G-1
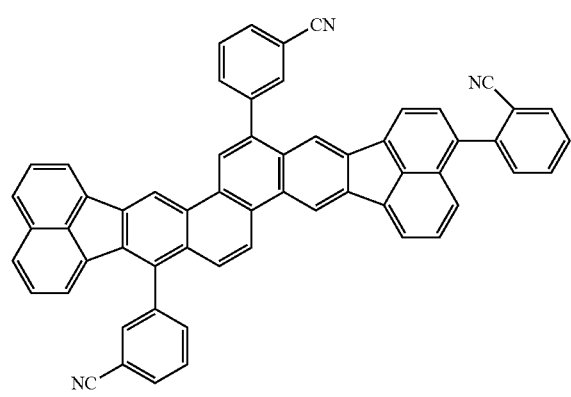
G-2
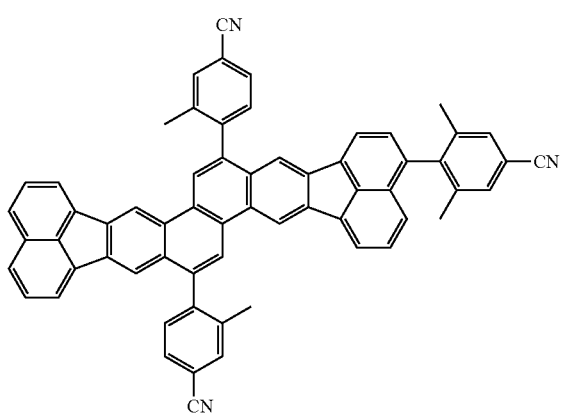

-continued
G-3
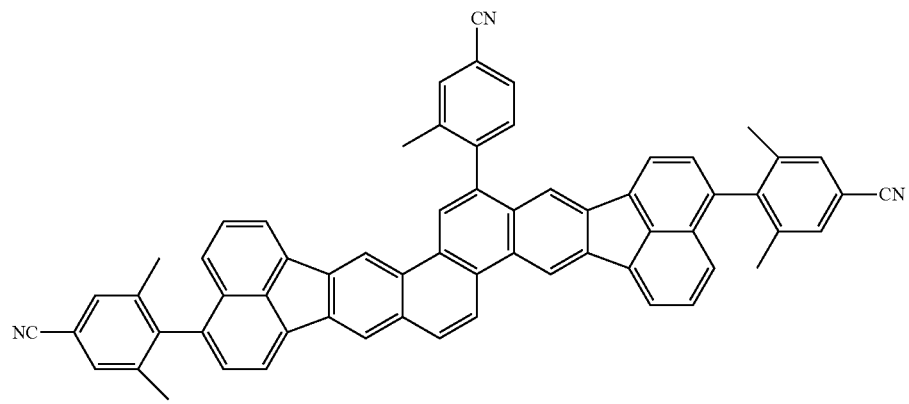
G-4
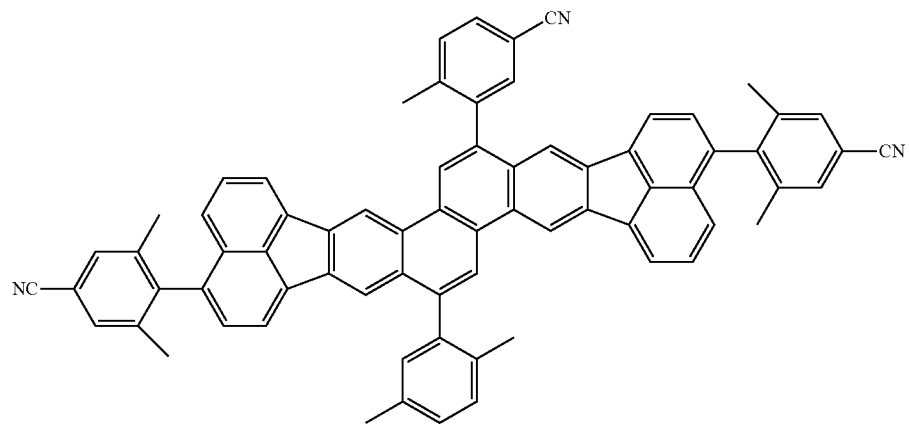
G-5
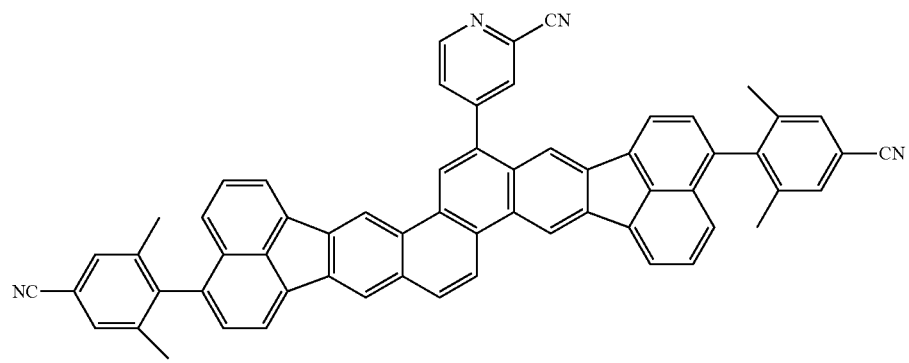
G-6
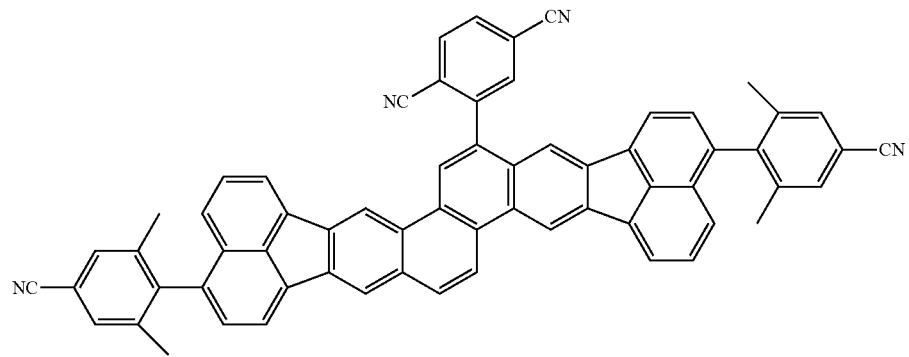

-continued
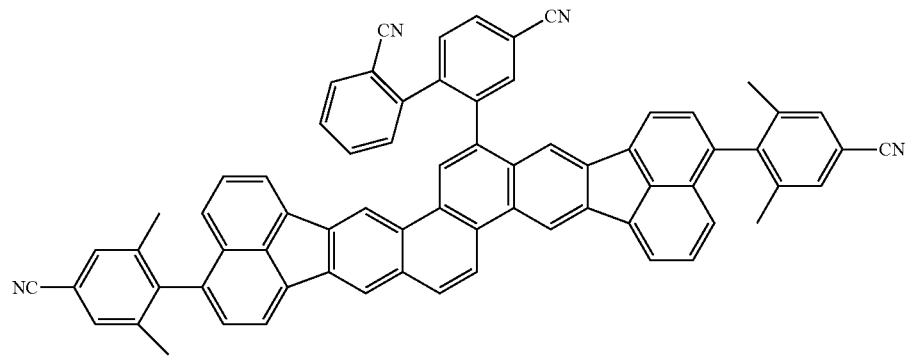
G-7
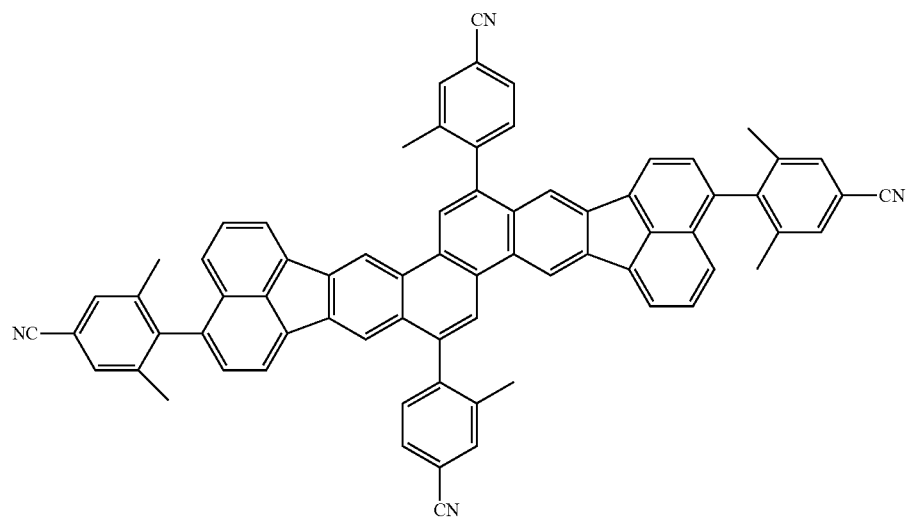
G-8
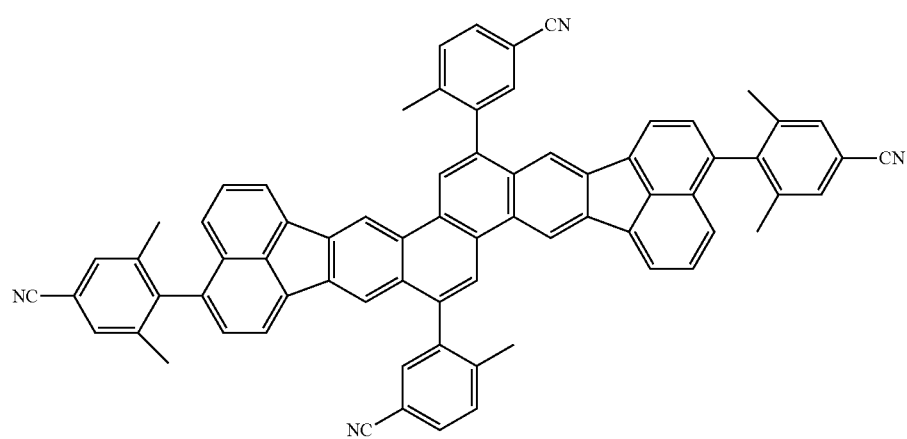
G-9

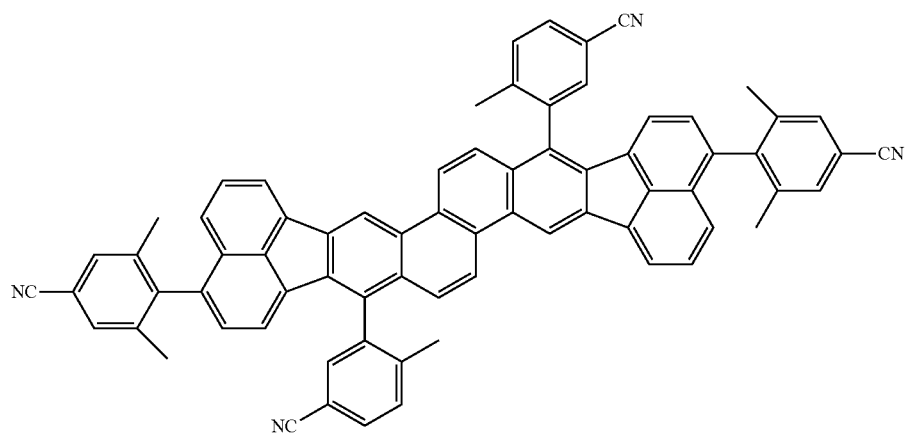
G-10
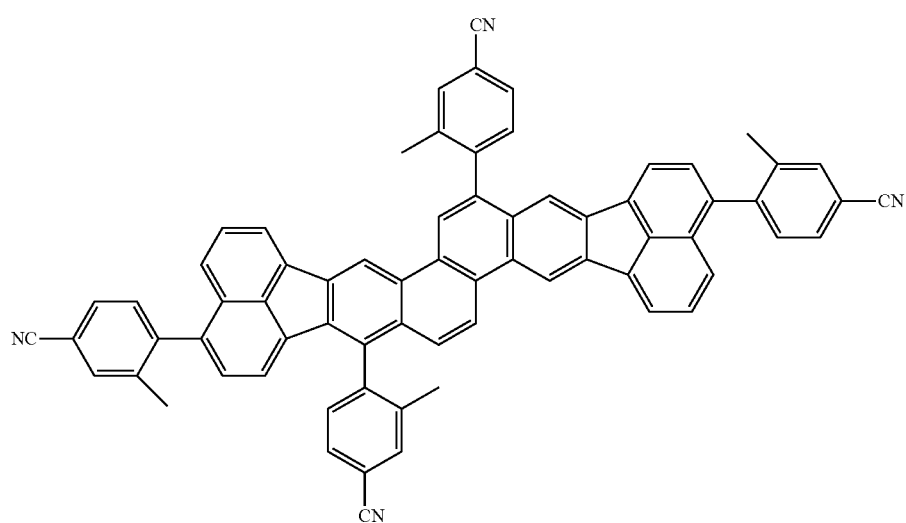
G-11
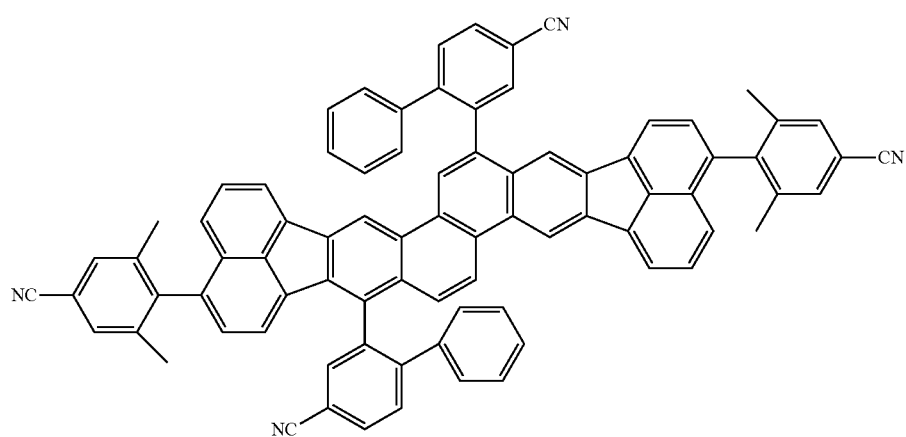
G-12

-continued

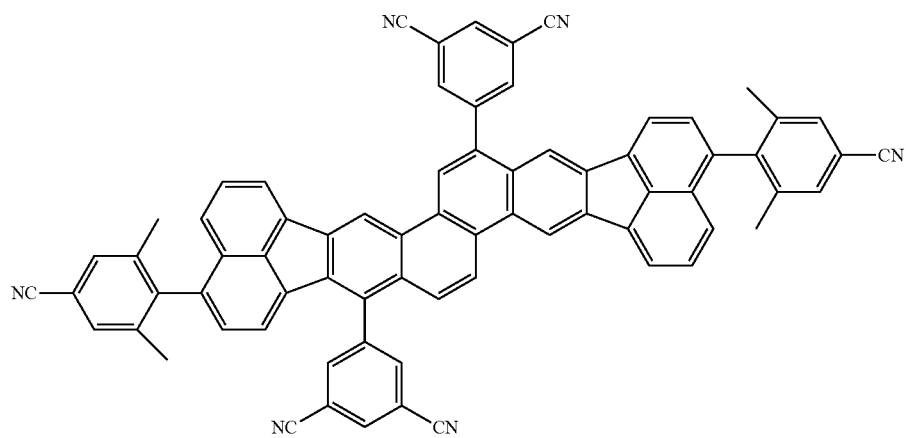
G-13

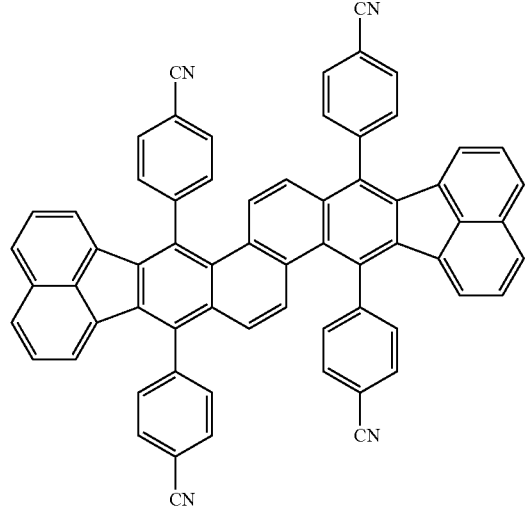
G-14

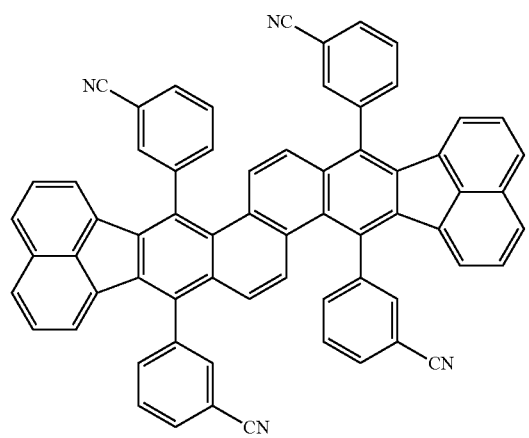
G-14

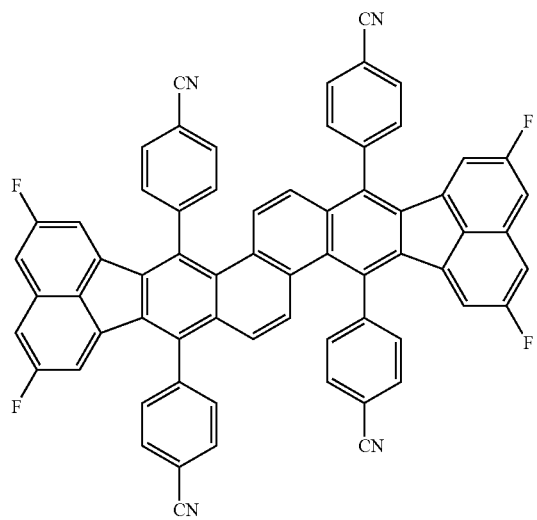
G-15

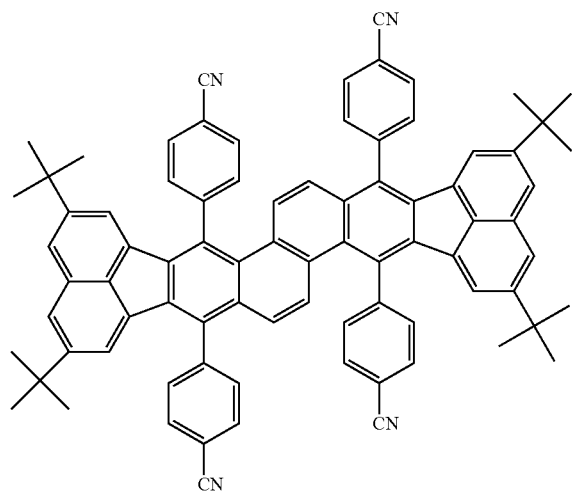
G-16

Among the above exemplary compounds, the exemplary compounds that belong to the D group are organic compounds in which a substituted or unsubstituted aryl group or heterocyclic group having at least one cyano group is introduced to at least one of $R_7$, $R_8$, $R_9$, $R_{16}$, $R_{17}$, and $R_{18}$ in the organic compound represented by the formula (1). As described above, such an organic compound has high electron acceptability and contributes to emitting blue light with a short wavelength, which achieves a high blue purity. Since the organic compound has high stability, the organic light-emitting element including the organic compound has a long life. Since a substituent is introduced to at least one of $R_7$, $R_8$, $R_9$, $R_{16}$, $R_{17}$, and $R_{18}$ in the formula (1), the planarity of the whole molecule is low and thus the degree of intermolecular stacking is decreased. Therefore, the organic compound has reduced crystallinity, reduced concentration quenching, and high sublimability.

Among the above exemplary compounds, the exemplary compounds that belong to the E group are compounds in which a substituent is asymmetrically introduced and thus have C1 symmetry, which is low symmetry, whereas the exemplary compounds that belong to the D group have C2 symmetry. Therefore, the intermolecular stacking on the whole molecule is suppressed and thus the crystallinity is reduced, which further reduces concentration quenching and improves sublimability.

Among the above exemplary compounds, the exemplary compounds that belong to the F group are organic compounds in which a substituted or unsubstituted aryl group or heterocyclic group having at least one cyano group is introduced to at least one of $R_3$, $R_4$, $R_{12}$, and $R_{13}$ in the formula (1). Since the substituent is introduced in the longitudinal direction of the molecule, the oscillator strength of the molecule is high.

Among the above exemplary compounds, the exemplary compounds that belong to the G group are organic compounds in which three or more of substituted or unsubstituted aryl groups or heterocyclic groups having at least one cyano group are introduced. Therefore, the exemplary compounds are chemically stable organic compounds having higher electron acceptability. The number of substituted or unsubstituted aryl groups or heterocyclic groups having at least one cyano group may be 4 or less.

Only one of $R_7$, $R_8$, $R_9$, $R_{16}$, $R_{17}$, and $R_{18}$ in the formula (1) may represent the aryl group or heterocyclic group having at least one cyano group. This is because, in this case, light with a shorter wavelength is emitted compared with the case where the aryl group or heterocyclic group having at least one cyano group is introduced to positions other than $R_7$, $R_8$, $R_9$, $R_{16}$, $R_{17}$, and $R_{18}$ in the formula (1), and thus an organic compound that provides a higher color purity is obtained. In particular, when none of $R_3$, $R_4$, $R_{12}$, and $R_{13}$ represents the aryl group having at least one cyano group or the heterocyclic group having at least one cyano group, light with a shorter wavelength is emitted. More specifically, $R_3$, $R_4$, $R_{12}$, and Ria in the formula (1) may represent a hydrogen atom.

Instead of the above-described exemplary compounds, the organic compound according to an embodiment of the present disclosure may be an organic compound having both the aryl group having at least one cyano group and the heterocyclic group having at least one cyano group.

Next, an organic light-emitting element according to an embodiment of the present disclosure will be described.

The organic light-emitting element according to this embodiment at least includes a first electrode and a second electrode, which are a pair of electrodes, and an organic compound layer disposed between the electrodes. In the organic light-emitting element according to this embodiment, the organic compound layer may have a single-layer structure or a multilayer structure including a plurality of layers as long as the organic compound layer includes a light-emitting layer. The pair of electrodes may be an anode and a cathode.

When the organic compound layer has a multilayer structure including a plurality of layers, the organic compound layer may include, in addition to the light-emitting layer, a hole injection layer, a hole transport layer, an electron blocking layer, a hole/exciton blocking layer, an electron transport layer, and an electron injection layer. The light-emitting layer may have a single-layer structure or a multilayer structure including a plurality of layers.

In the organic light-emitting element according to this embodiment, the organic compound according to this embodiment is contained in at least one layer of the organic compound layer. Specifically, the organic compound according to this embodiment is contained in any of the hole injection layer, the hole transport layer, the electron blocking layer, the light-emitting layer, the hole/exciton blocking layer, the electron transport layer, and the electron injection layer. The organic compound according to this embodiment may be contained in the light-emitting layer.

In the organic light-emitting element according to this embodiment, when the organic compound according to this embodiment is contained in the light-emitting layer, the light-emitting layer may be a layer formed of only the organic compound according to this embodiment or may be a layer containing a first compound serving as the organic compound according to this embodiment and a second compound different from the first compound. When the light-emitting layer is a layer containing the first compound and the second compound, the first compound may be used as a host of the light-emitting layer or a guest of the light-emitting layer. Alternatively, the organic compound may be used as an assist material that can be contained in the light-emitting layer.

Herein, the host refers to a compound having the highest weight ratio among the compounds that form the light-emitting layer. The guest refers to a compound that has a lower weight ratio than the host and that is responsible for main light emission among the compounds that form the light-emitting layer. The assist material refers to a compound that has a lower weight ratio than the host and that assists light emission of the guest among the compounds that form the light-emitting layer. The assist material is also referred to as a second host.

When the organic compound according to this embodiment is used as a guest of the light-emitting layer, the concentration of the guest is preferably 0.01 wt % or more and 20 wt % or less and more preferably 0.1 wt % or more and 5.0 wt % or less relative to the whole light-emitting layer.

When the organic compound according to this embodiment is used as a guest of the light-emitting layer, a material having a higher LUMO energy level than the organic compound according to this embodiment (a material having a LUMO energy level closer to the vacuum level) may be used as the host. This is because when a material having a higher LUMO energy level than the organic compound according to this embodiment having a low LUMO energy level is used as the host, the organic compound according to this embodiment can accept a larger amount of electrons supplied to the host of the light-emitting layer.

As a result of thorough studies, the present inventors have found that when the organic compound according to this embodiment is used as the host or guest of the light-emitting layer, in particular, as the guest of the light-emitting layer, an element that produces an optical output with high efficiency and high luminance and that has very high durability is provided. This light-emitting layer may have a single-layer structure or a multilayer structure, or a blue emission color that is an emission color of this embodiment can be mixed with another color by adding a light-emitting material having another emission color. The multilayer structure refers to a state in which the light-emitting layer and another light-emitting layer are stacked. In this case, the emission color of the organic light-emitting element is not limited to blue. The emission color may be specifically white or an intermediate color. In the case of white, the other light-emitting layer emits light having a color other than blue, such as red or green. The light-emitting layers are formed by a method such as vapor deposition or coating. The details of the method will be specifically described in Examples below.

The organic compound according to this embodiment can be used as a material for organic compound layers other than the light-emitting layer that constitute the organic light-emitting element according to this embodiment. Specifically, the organic compound may be used as a material for, for example, electron transport layers, electron injection layers, hole transport layers, hole injection layers, and hole blocking layers. In this case, the emission color of the organic light-emitting element is not limited to blue. The emission color may be specifically white or an intermediate color.

When the organic light-emitting element according to this embodiment is produced, the organic compound according to this embodiment may be used in combination with, for example, a publicly known low-molecular-weight or high-molecular-weight compound such as a hole injection or transport compound, a compound serving as the host, a luminous compound, an electron injection or transport compound if necessary.

Examples of these compounds will be described below.

A hole injection or transport material may be a material having a high hole mobility such that injection of holes from the anode is facilitated and the injected holes can be transported to the light-emitting layer. The hole injection or transport material may also be a material having a high glass transition temperature in order to suppress the deterioration of the film quality, such as crystallization in the organic light-emitting element. Examples of the low-molecular-weight or high-molecular-weight material having hole injectability or transportability include triarylamine derivatives, arylcarbazole derivatives, phenylenediamine derivatives, stilbene derivatives, phthalocyanine derivatives, porphyrin derivatives, poly(vinylcarbazole), poly(thiophene), and other electrically conductive polymers. The above hole injection or transport material is also suitably used for the electron blocking layer.

Non-limiting specific examples of the compound used as the hole injection or transport material are shown below.

HT1

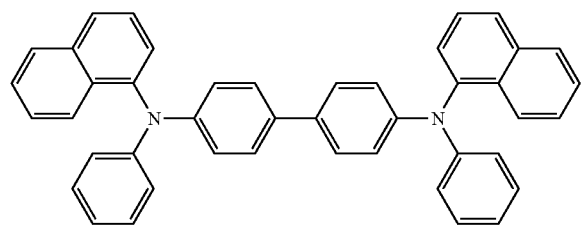

HT2

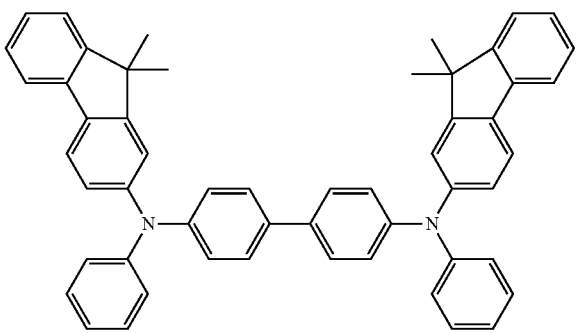

HT3

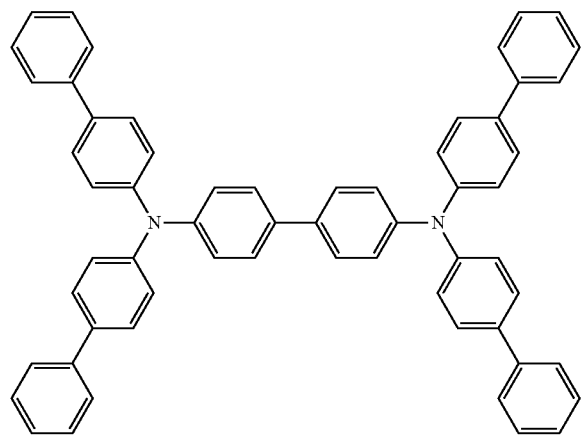

HT4

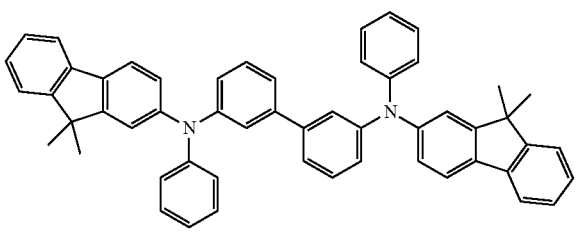

-continued
HT5 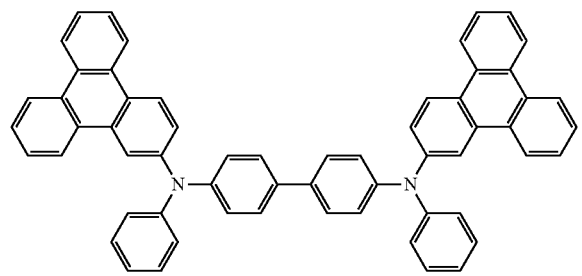 HT6
HT7 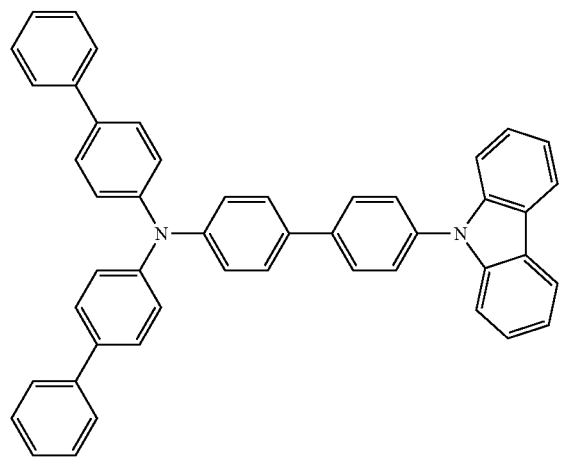 HT8 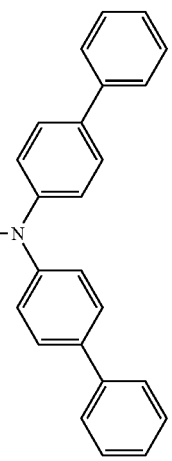
HT9 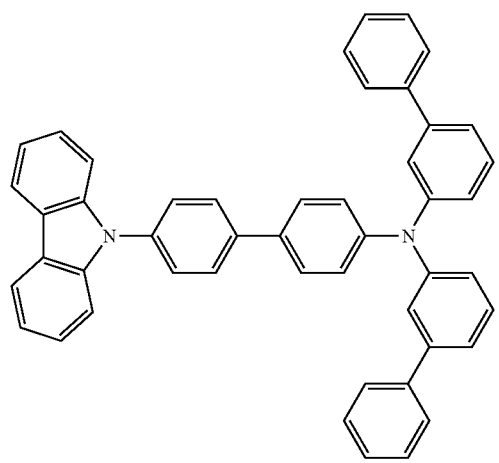 HT10
HT11 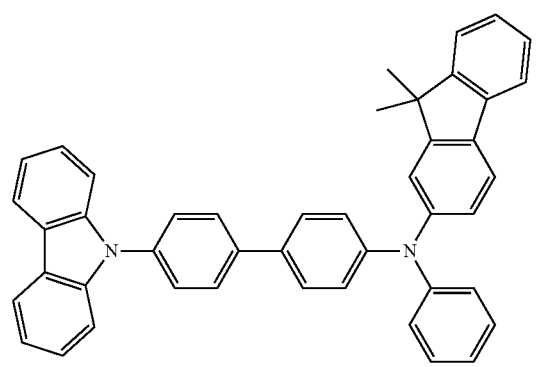 HT12 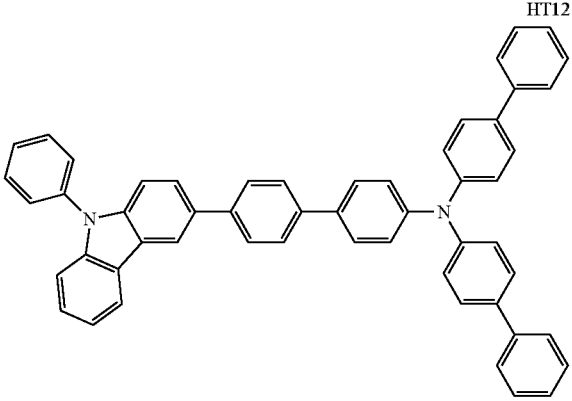

-continued

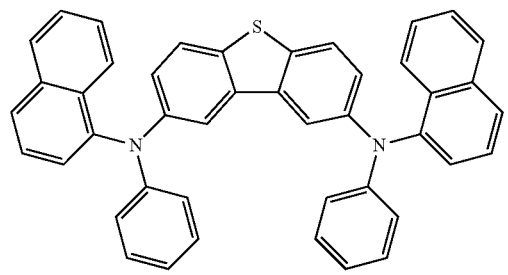

HT13

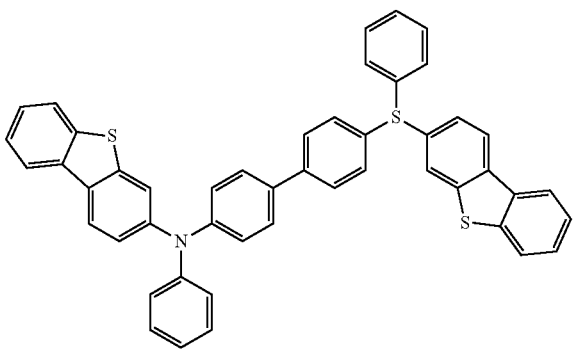

HT14

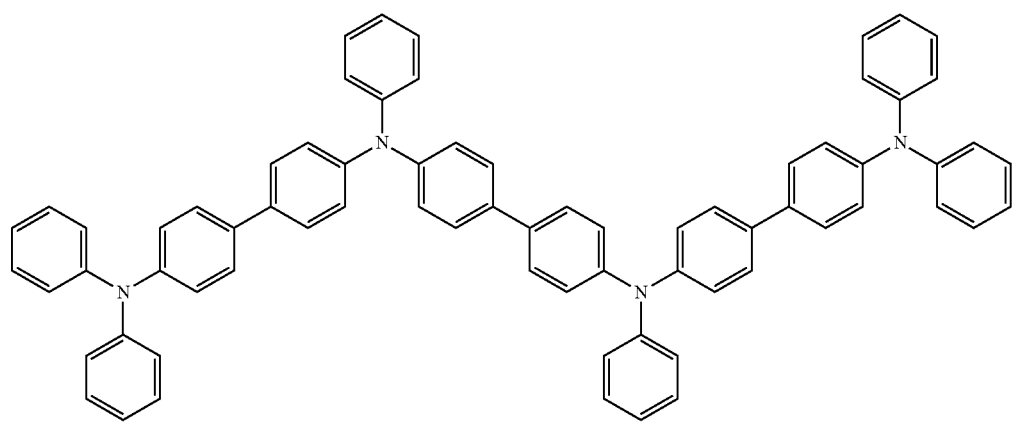

HT15

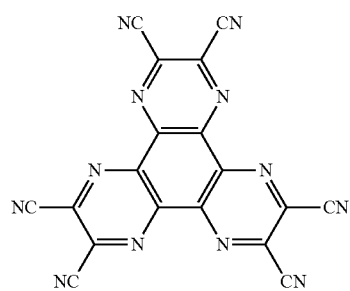

HT16

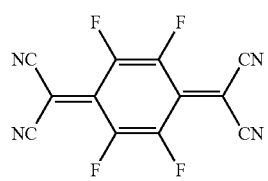

HT17

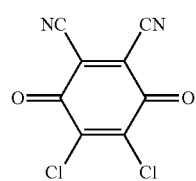

HT18

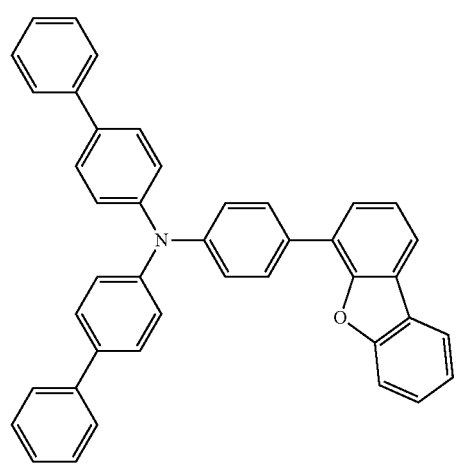

HT19

When HT16 to HT18 among the hole transport materials are used for a layer in contact with the anode, the driving voltage can be decreased. HT16 is widely used for organic light-emitting elements. HT2, HT3, HT10, and HT12 may be used for the organic compound layer adjacent to HT 16. One organic compound layer may be formed of a plurality of materials. For example, combinations of HT2 and HT4, HT3 and HT10, and HT8 and HT9 may be used.

Examples of the light-emitting material mainly concerned with a light-emitting function include, in addition to the organic compound represented by the formula (1), fused ring compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organoaluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

Non-limiting specific examples of the compound used as the light-emitting material are shown below.

BD1
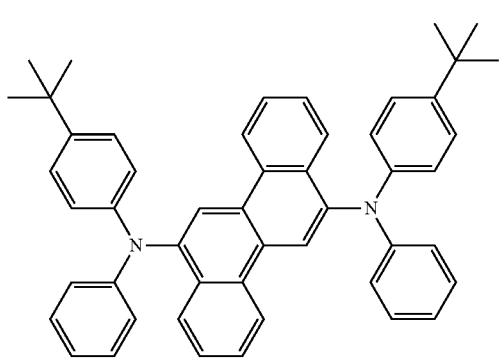

BD2
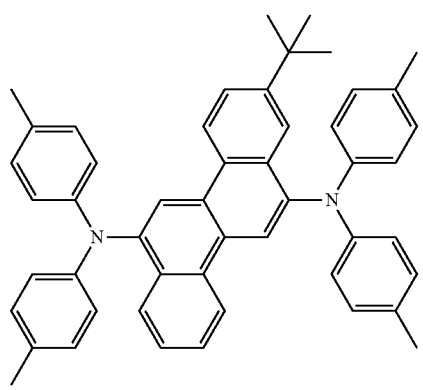

BD3
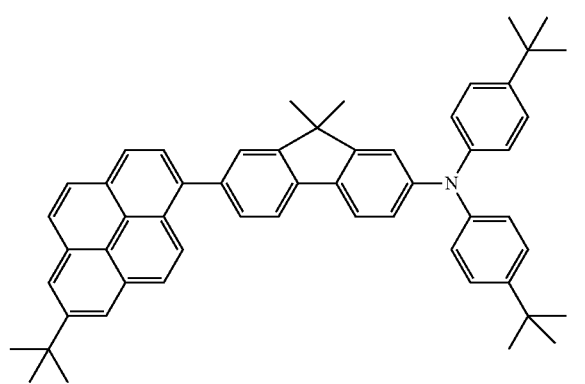

BD4
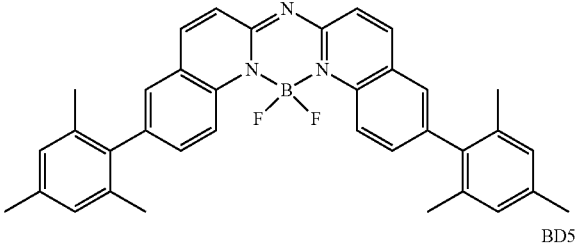

BD5
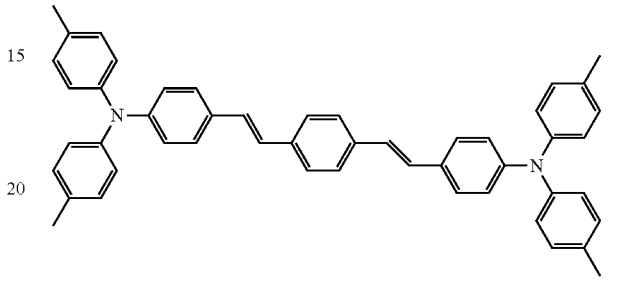

BD6
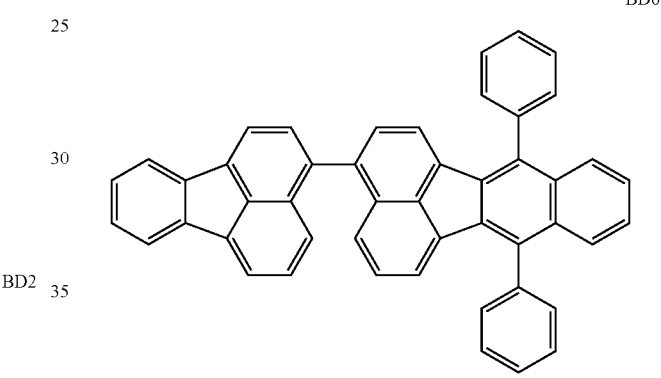

BD7
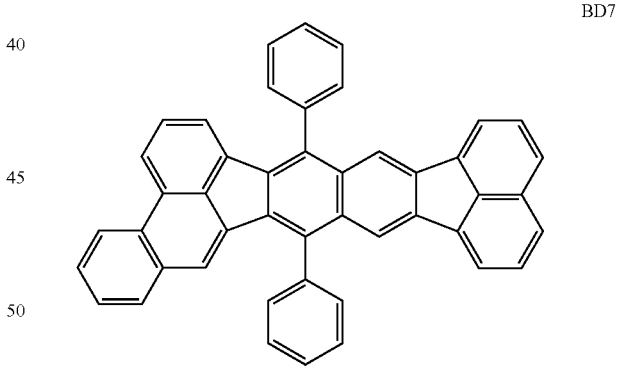

BD8
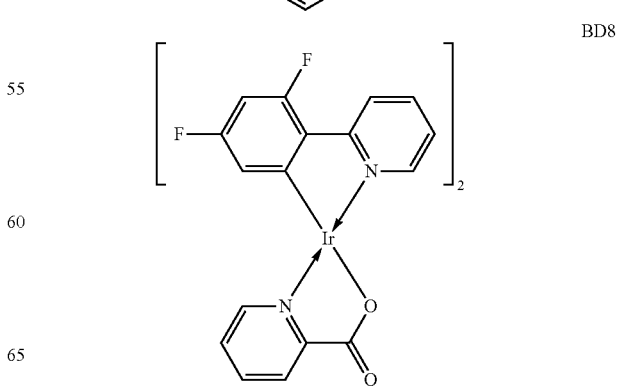

GD1
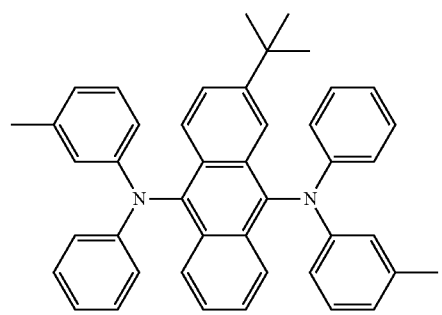
GD2
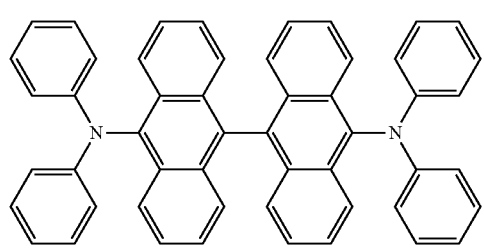
GD3
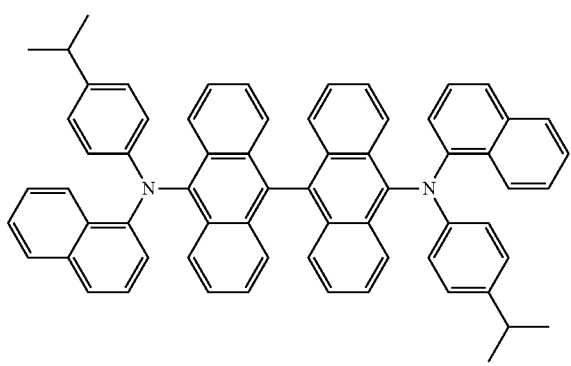
GD4
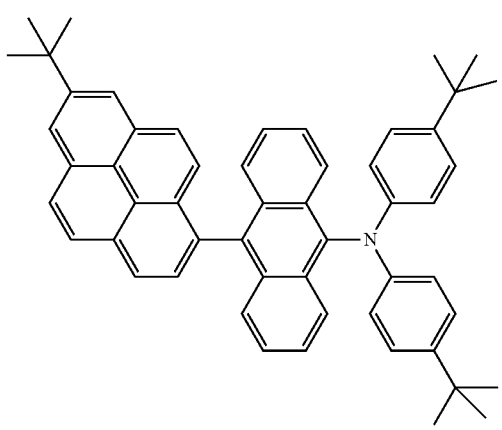
GD5
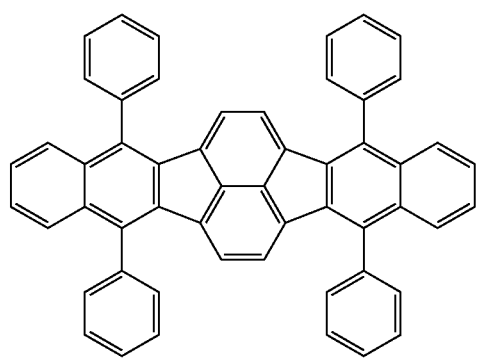
GD6
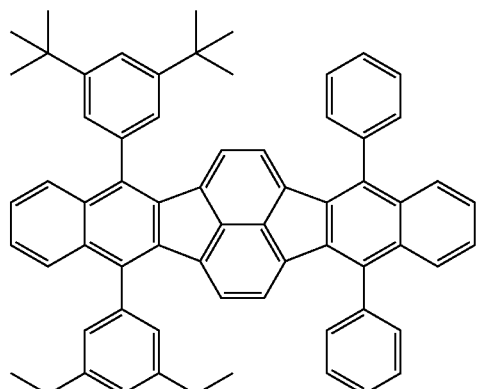
GD7
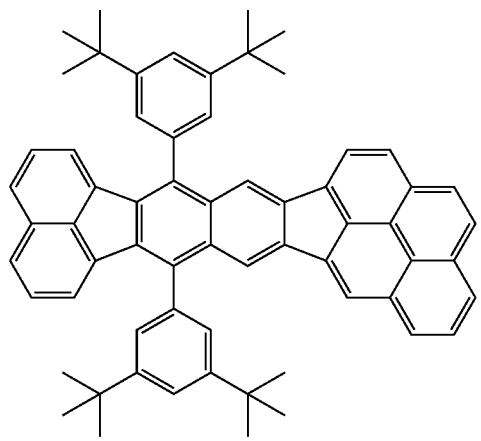
GD8
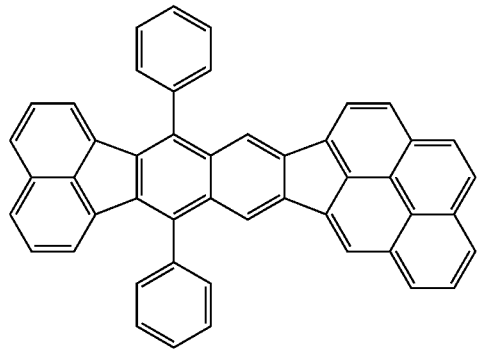

-continued
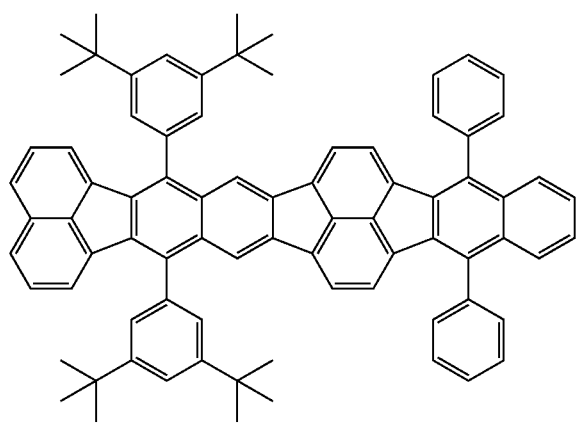
GD9
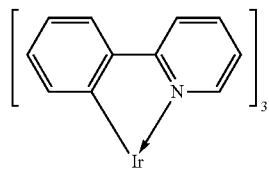
GD10
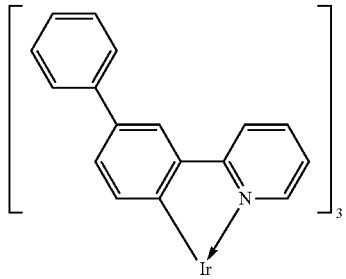
GD11
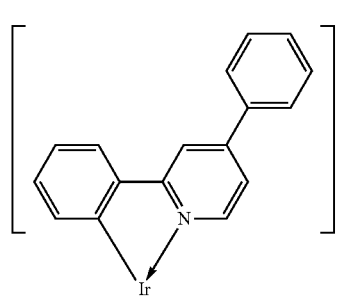
GD12
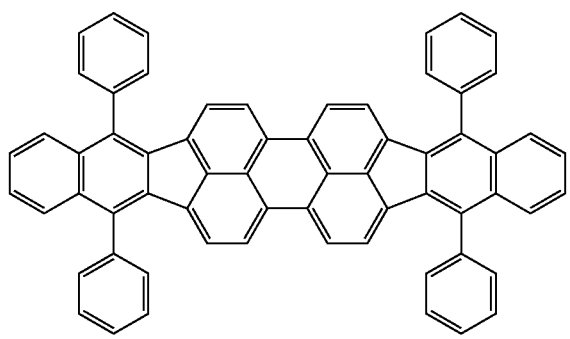
RD1
-continued
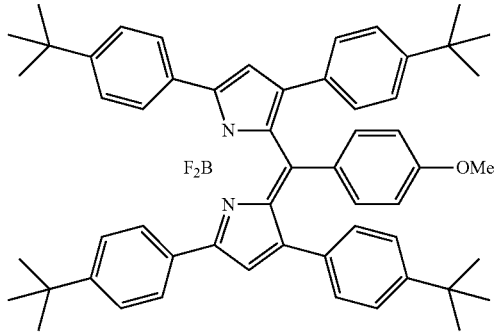
RD2
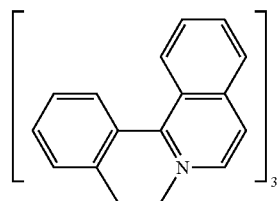
RD3
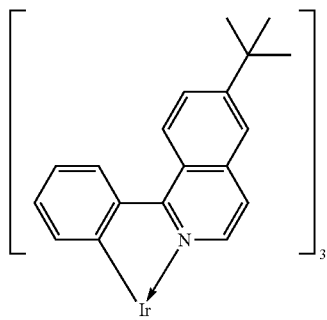
RD4
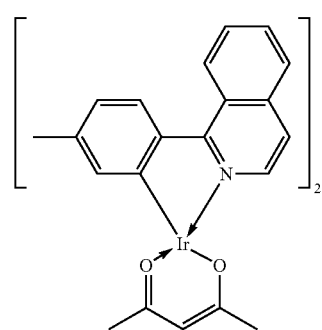
RD5

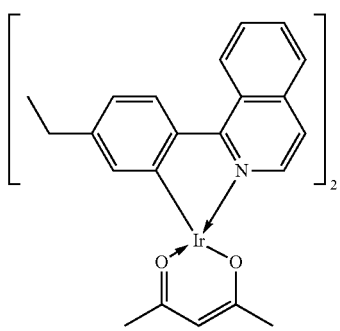

RD6

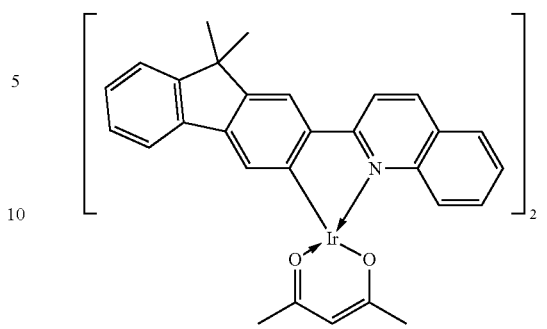

RD8

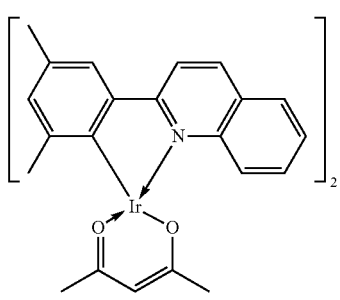

RD7

Examples of the light-emitting-layer host or light emission assist material contained in the light-emitting layer include aromatic hydrocarbon compounds and derivatives thereof, carbazole derivatives, dibenzofuran derivatives, dibenzothiophene derivatives, organoaluminum complexes such as tris(8-quinolinolato)aluminum, and organoberyllium complexes.

In particular, the host material may have an anthracene, tetracene, perylene, fluorene, or pyrene skeleton in its molecular skeleton. This is because the host material is formed of a hydrocarbon as described above and also has an S1 energy capable of causing sufficient energy transfer to the organic compound according to an embodiment of the present disclosure.

Non-limiting specific examples of the compound used as the light-emitting-layer host or light emission assist material contained in the light-emitting layer are shown below.

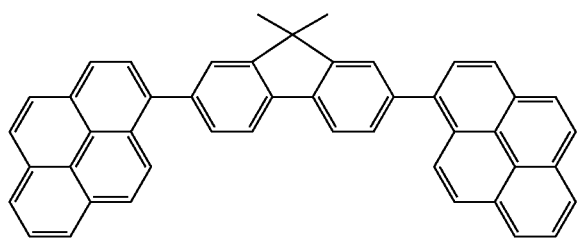

EM1

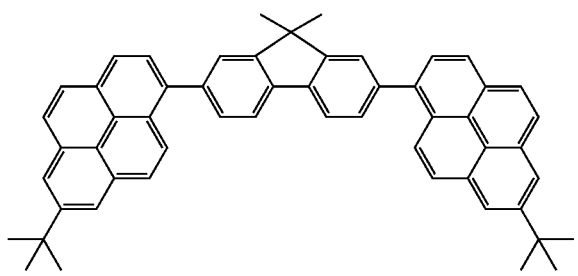

EM2

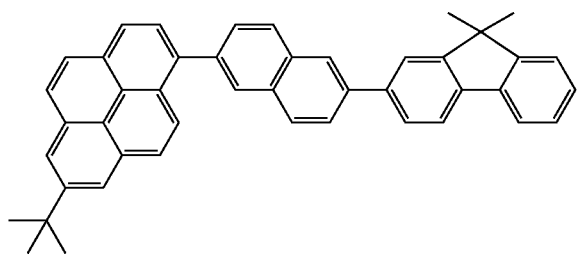

EM3

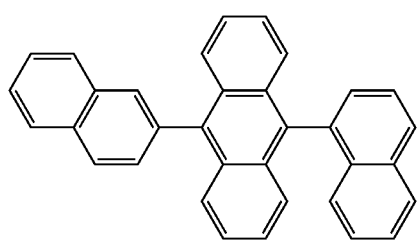

EM5

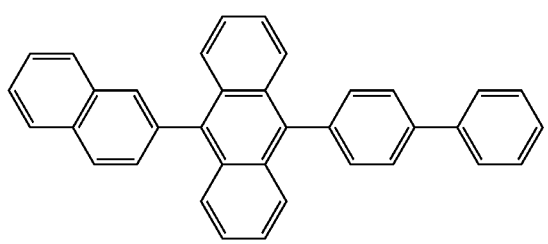

EM6

EM4

-continued
EM7
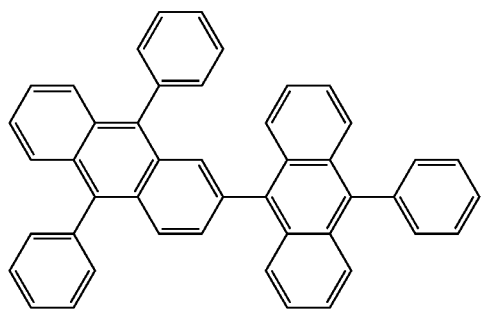
EM8
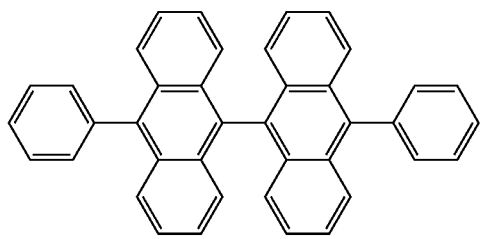
EM9
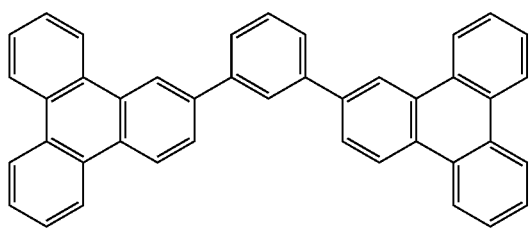
EM10
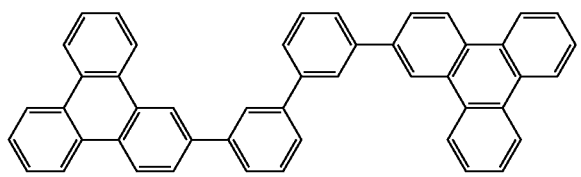
EM11
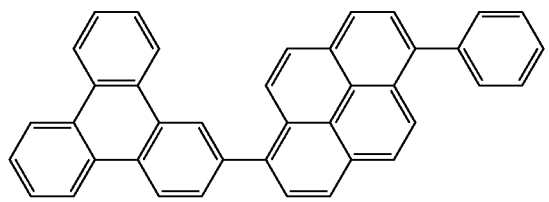
EM12
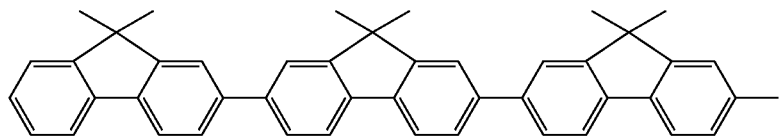
EM13
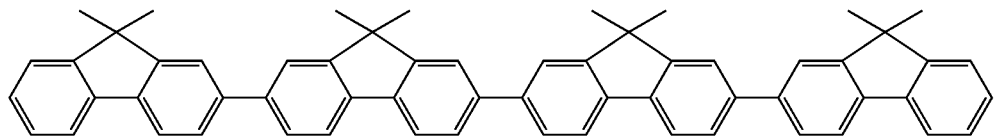
EM14
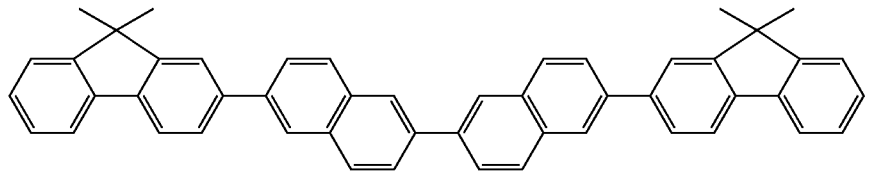
EM15
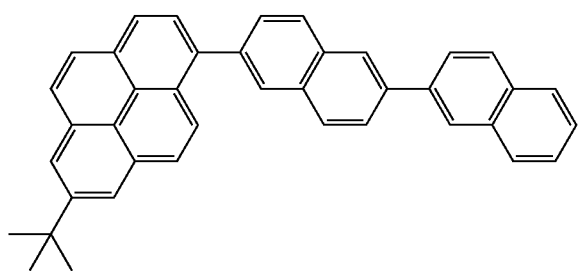
EM16
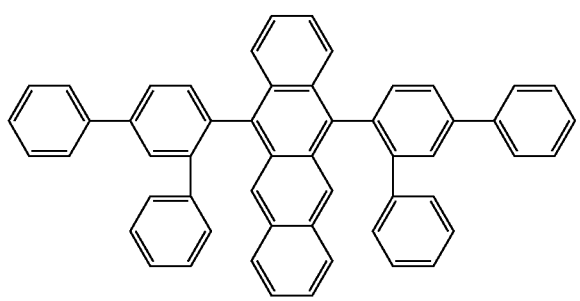

-continued
EM17
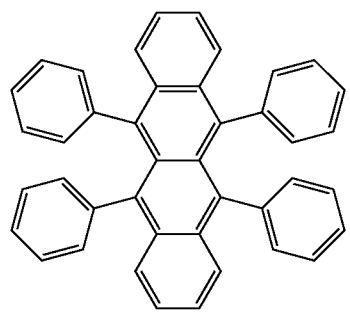
EM18
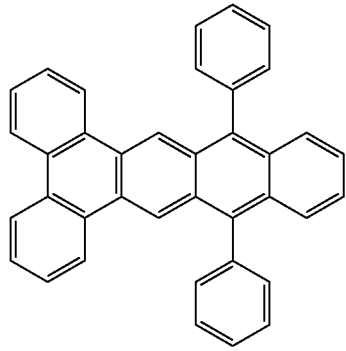
EM19
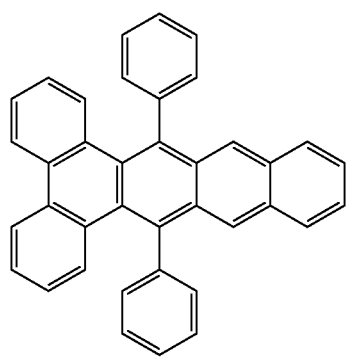
EM20
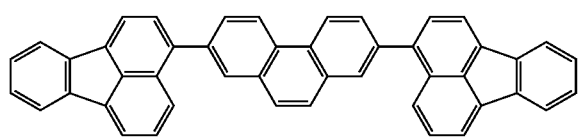
EM21
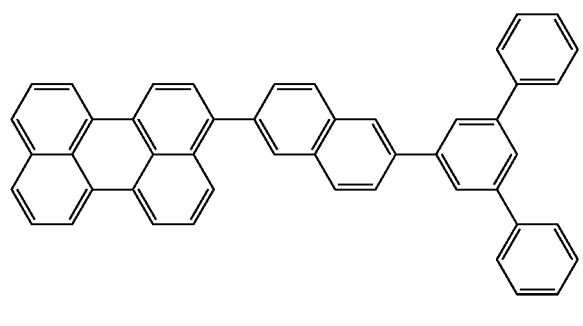
EM22
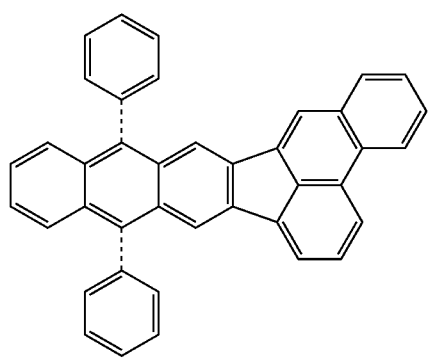
EM23
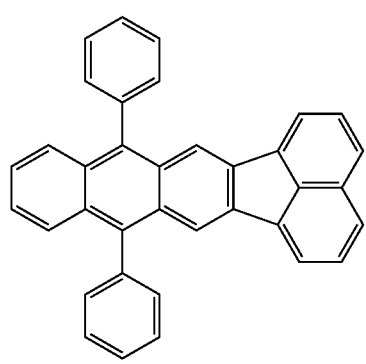
EM24

-continued

EM25
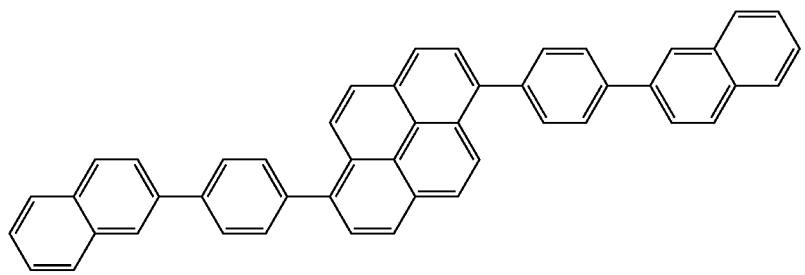

EM26
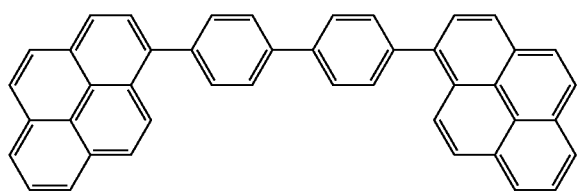

EM27
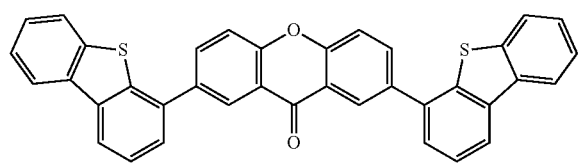

EM28
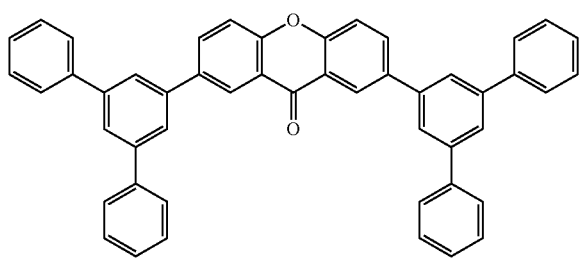

EM29
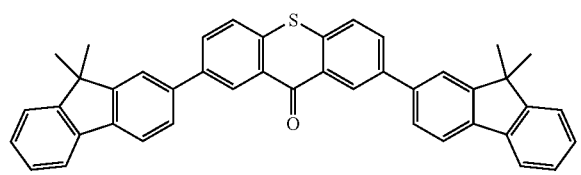

EM30
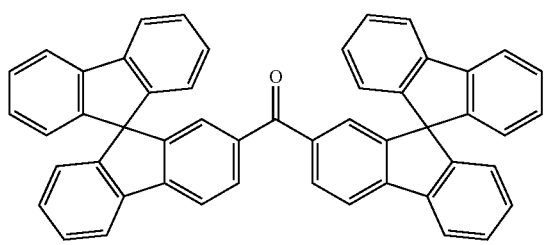

EM31
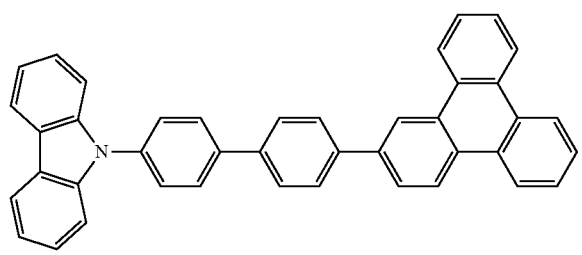

EM32
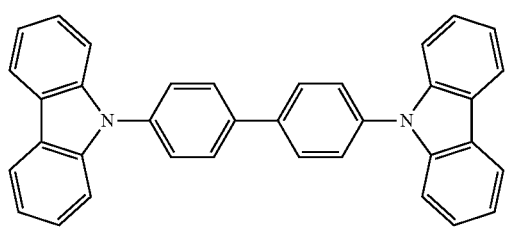

The electron transport material can be freely selected from materials capable of transporting electrons injected from the cathode to the light-emitting layer. The electron transport material is selected in consideration of, for example, the balance with the hole mobility of the hole transport material. Examples of the material having electron transportability include oxadiazole derivatives, oxazole derivatives, pyrazine derivatives, triazole derivatives, triazine derivatives, quinoline derivatives, quinoxaline derivatives, phenanthroline derivatives, organoaluminum complexes, and fused ring compounds (e.g., fluorene derivatives, naphthalene derivatives, chrysene derivatives, and anthracene derivatives). The above electron transport material is also suitably used for the hole blocking layer.

Non-limiting specific examples of the compound used as the electron transport material are shown below.

ET1
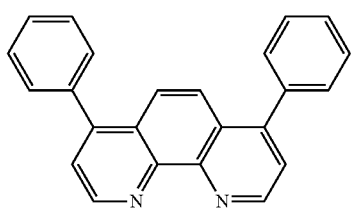

ET2
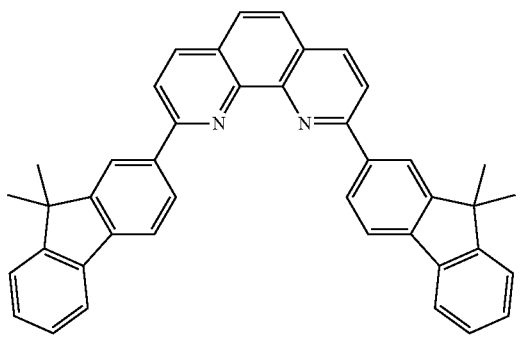
ET3
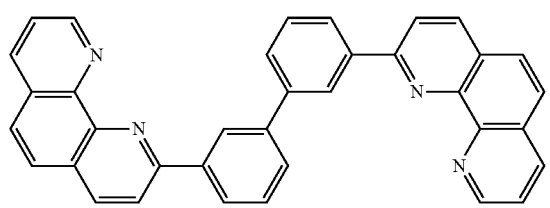
ET4
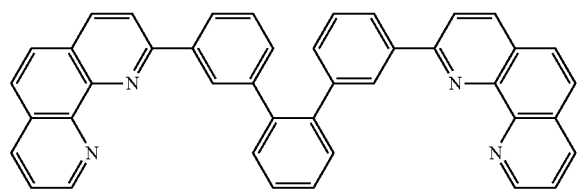
ET5
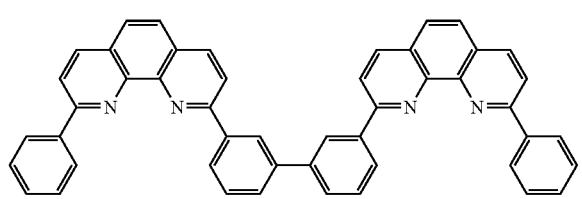
ET6
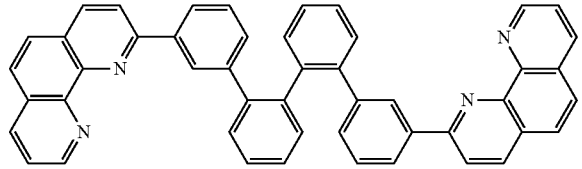
ET7
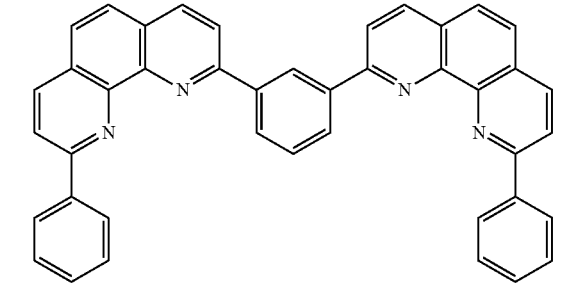
ET8
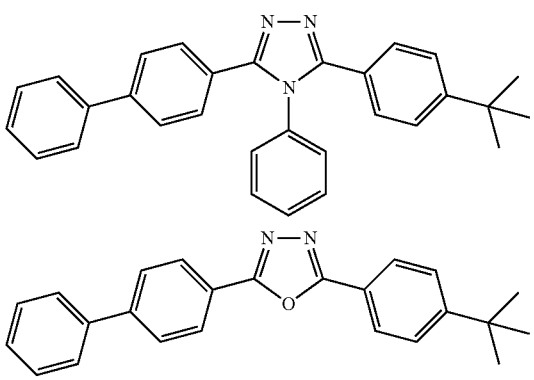
ET10
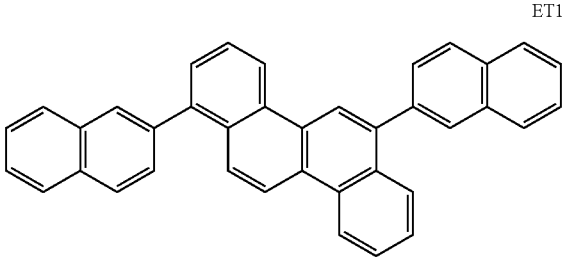
ET11
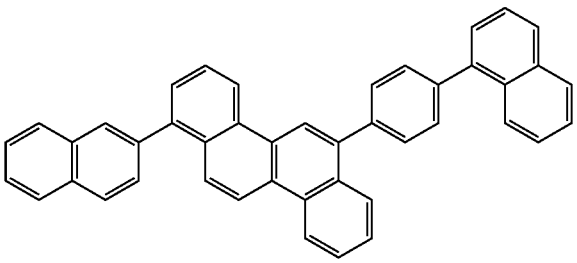
ET12
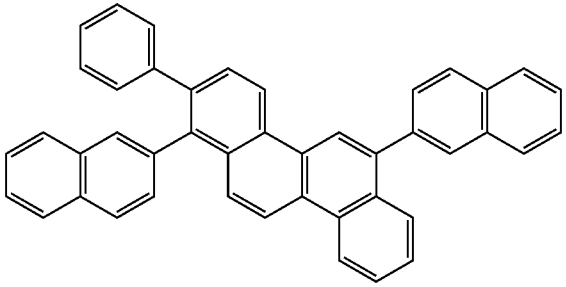
ET13
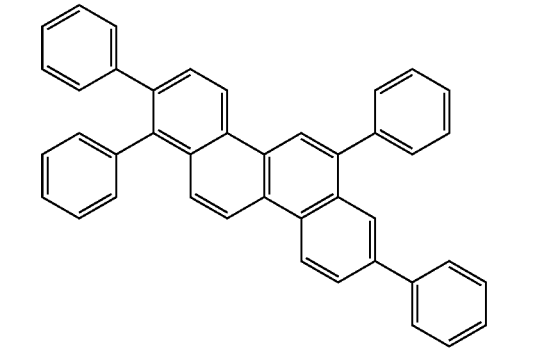

ET14
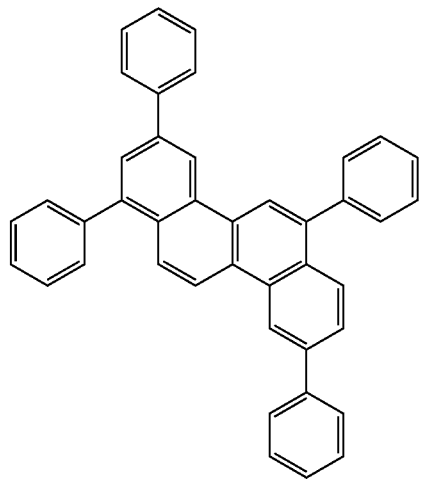
ET15
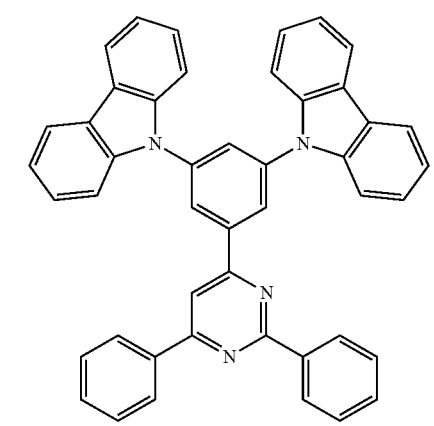
ET16
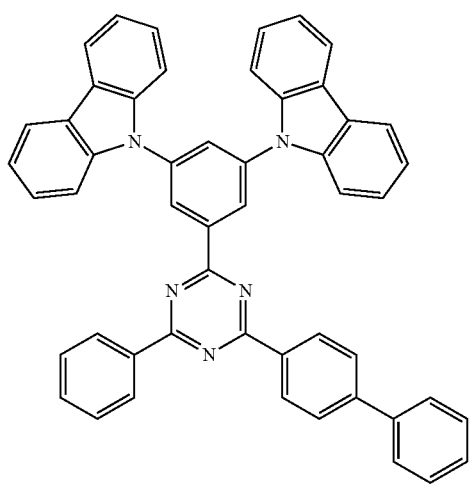
ET17
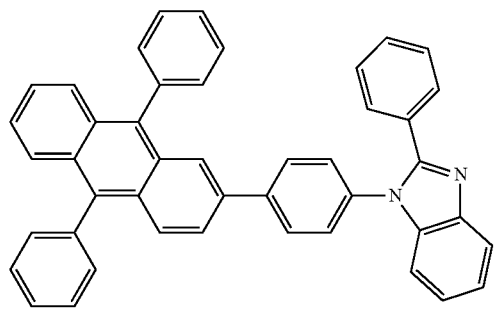
ET18
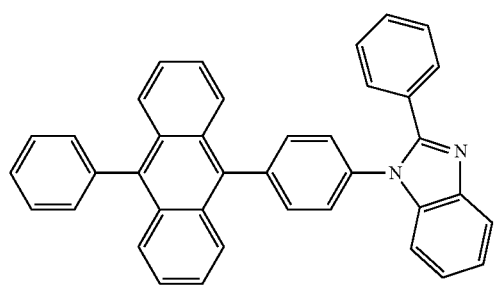
ET19
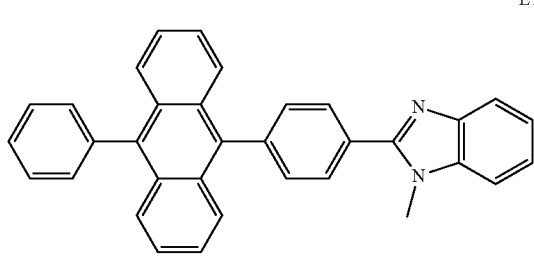
ET20
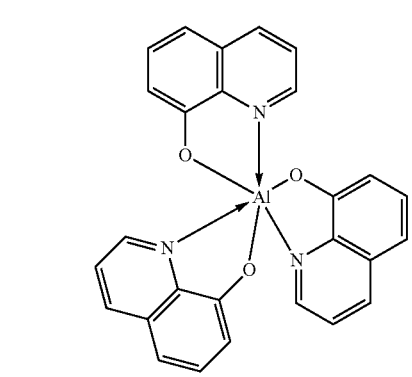
ET21
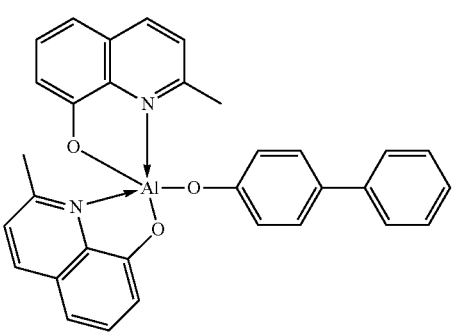

-continued

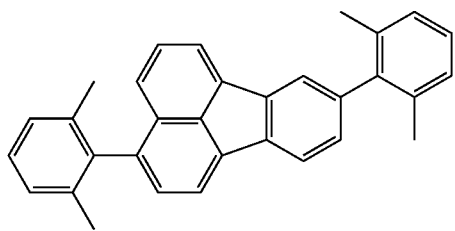
ET22

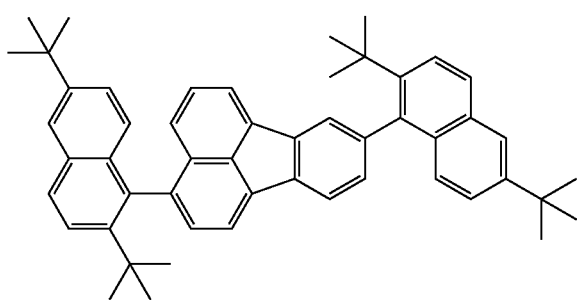
ET23

The electron injection material can be freely selected from materials capable of readily injecting electrons from the cathode in consideration of, for example, the balance with hole injection property. An n-type dopant and a reducing dopant are contained as an organic compound. Examples of the electron injection material include compounds containing an alkali metal such as lithium fluoride, lithium complexes such as lithium quinolinol, benzimidazolidene derivatives, imidazolidene derivatives, fulvalene derivatives, and acridine derivatives.

Configuration of Organic Light-Emitting Element

The organic light-emitting element is provided by forming a first electrode, an organic compound layer, and a second electrode on an insulating layer disposed on a substrate. For example, a protective layer and a color filter may be disposed on the second electrode. If the color filter is disposed, a planarizing layer may be disposed between the protective layer and the color filter. The planarizing layer may be formed of, for example, an acrylic resin. One of the first electrode and the second electrode may be an anode, and the other may be a cathode.

Substrate

The substrate is formed of, for example, quartz, glass, silicon wafer, resin, or metal. A switching element such as a transistor and a wire may be disposed on the substrate, and an insulating layer may be disposed thereon. The insulating layer may be formed of any material as long as contact holes can be formed to establish electrical connection between the anode and the wire and the anode can be insulated from wires to which the anode is not connected. Examples of the material for the insulating layer include resins such as polyimide, silicon oxide, and silicon nitride.

Electrode

The electrode may be a pair of electrodes. The pair of electrodes may be an anode and a cathode. When an electric field is applied in a direction in which the organic light-emitting element emits light, the electrode having a high electric potential is an anode and the other electrode is a cathode. It can also be said that the electrode that supplies holes to the light-emitting layer is an anode and the electrode that supplies electrons is a cathode.

The material for the anode desirably has as high a work function as possible. Examples of the material for the anode include elemental metals such as gold, platinum, silver, copper, nickel, palladium, cobalt, selenium, vanadium, and tungsten; mixtures containing these metals; alloys of these metals; and metal oxides such as tin oxide, zinc oxide, indium oxide, indium tin oxide (ITO), and indium zinc oxide. Conductive polymers such as polyaniline, polypyrrole, and polythiophene can also be used.

These electrode materials may be used alone or in combination of two or more. The anode may have a single-layer structure or a multilayer structure.

When the anode is used as a reflective electrode, for example, chromium, aluminum, silver, titanium, tungsten, molybdenum, an alloy thereof, or a laminate thereof can be used. When the anode is used as a transparent electrode, a transparent conductive oxide layer made of, for example, indium tin oxide (ITO) or indium zinc oxide can be used, but the materials are not limited thereto. The electrode can be formed by photolithography.

On the other hand, the material for the cathode desirably has a low work function. Examples of the material for the cathode include alkali metals such as lithium; alkaline earth metals such as calcium; elemental metals such as aluminum, titanium, manganese, silver, lead, and chromium; mixtures containing these metals; alloys of these metals, such as magnesium-silver, aluminum-lithium, aluminum-magnesium, silver-copper, and zinc-silver; and metal oxides such as indium tin oxide (ITO). These electrode materials may be used alone or in combination of two or more. The cathode may have a single-layer structure or a multilayer structure. In particular, silver is preferably used and a silver alloy is more preferably used to suppress aggregation of silver. The silver alloy may have any mixing ratio such as 1:1 as long as the aggregation of silver can be suppressed.

Any device may be employed, such as a top emission device obtained by using a conductive oxide layer made of, for example, ITO as a cathode or a bottom emission device obtained by using a reflective electrode made of, for example, aluminum (Al) as a cathode. The method for forming a cathode is not particularly limited. For example, a DC and AC sputtering method may be employed because good film coverage can be achieved to readily reduce the resistance.

Protective Layer

A protective layer may be disposed on the cathode. For example, a glass plate including a moisture absorbent is bonded to the cathode. This suppresses permeation of water or the like into the organic compound layer and thus can suppress occurrence of display defects. In another embodiment, a passivation film made of silicon nitride or the like may be disposed on the cathode to suppress permeation of water or the like into the organic EL layer. For example, after the formation of the cathode, the resulting substrate may be transferred to another chamber without breaking the vacuum, and a silicon nitride film having a thickness of 2 µm may be formed by a chemical vapor deposition (CVD) method to provide a protective layer. After the film formation by the CVD method, a protective layer may be disposed by an atomic layer deposition method (ALD method).

Color Filter

A color filter may be disposed on the protective layer. For example, a color filter provided in consideration of the size of organic light-emitting elements is disposed on another substrate, and this substrate may be bonded to the substrate on which the organic light-emitting elements have been disposed. Alternatively, a color filter may be patterned on the above-described protective layer by photolithography. The color filter may be formed of a polymer.

Planarizing Layer

A planarizing layer may be disposed between the color filter and the protective layer. The planarizing layer may be formed of an organic compound. The organic compound may be a low-molecular-weight organic compound or may be a high-molecular-weight organic compound, but is desirably a high-molecular-weight organic compound.

The planarizing layer may be disposed on and below the color filter, and both the planarizing layers may be formed of the same material or different materials. Specific examples of the material include polyvinyl carbazole resin, polycarbonate resin, polyester resin, ABS resin, acrylic resin, polyimide resin, phenolic resin, epoxy resin, silicone resin, and urea resin.

Counter Substrate

A counter substrate may be disposed on the planarizing layer. The name of the counter substrate is derived from the fact that the counter substrate is disposed at a position corresponding to that of the above-described substrate. The counter substrate may be formed of the same material as the above-described substrate. If the above-described substrate is a first substrate, the counter substrate may be a second substrate.

Organic Compound Layer

The organic compound layers (e.g., a hole injection layer, a hole transport layer, an electron blocking layer, a light-emitting layer, a hole blocking layer, an electron transport layer, and an electron injection layer) that constitute the organic light-emitting element according to an embodiment of the present disclosure are formed by the following method.

The organic compound layers that constitute the organic light-emitting element according to an embodiment of the present disclosure can be formed by a dry process such as a vacuum vapor deposition method, an ionized vapor deposition method, a sputtering method, or a method using plasma. Instead of the dry process, a wet process in which an organic compound is dissolved in an appropriate solvent and a layer is formed by a publicly known coating method (e.g., spin coating, dipping, a casting method, a Langmuir-Blodgett (LB) method, or an ink jet method) can also be employed.

When a layer is formed by, for example, a vacuum vapor deposition method or a solution coating method, crystallization or the like is unlikely to occur and the resulting layer has high stability over time. When a layer is formed by a coating method, the layer can be formed by using an appropriate binder resin in combination.

Non-limiting examples of the binder resin include polyvinyl carbazole resin, polycarbonate resin, polyester resin, ABS resin, acrylic resin, polyimide resin, phenolic resin, epoxy resin, silicone resin, and urea resin.

These binder resins may be used alone as a homopolymer or in combination as a mixture of two or more as a copolymer. Furthermore, publicly known additives such as a plasticizer, an antioxidant, and an ultraviolet absorber may be optionally used in combination.

Application of Organic Light-Emitting Element According to Embodiment of the present Disclosure The organic light-emitting element according to an embodiment of the present disclosure can be used as a member of display apparatuses and lighting apparatuses. In addition, the organic light-emitting element may be used as, for example, an exposure light source for electrophotographic image forming apparatuses, a backlight of liquid crystal display apparatuses, and a light-emitting device including a white light source having a color filter.

The display apparatus may be an image information processing apparatus that includes an image input unit which inputs image information from an area CCD, a linear CCD, a memory card, or the like and an information processing unit which processes the input information and that displays the input image on a display unit.

The display unit included in an image pickup apparatus or an ink jet printer may have a touch panel function. The touch panel function may be driven by any method such as a method that uses infrared rays, electrostatic capacitance, a resistive film, or electromagnetic induction. The display apparatus may be used as a display unit of multifunction printers.

Next, a display apparatus according to this embodiment will be described with reference to the attached drawings.

Figure 2A:
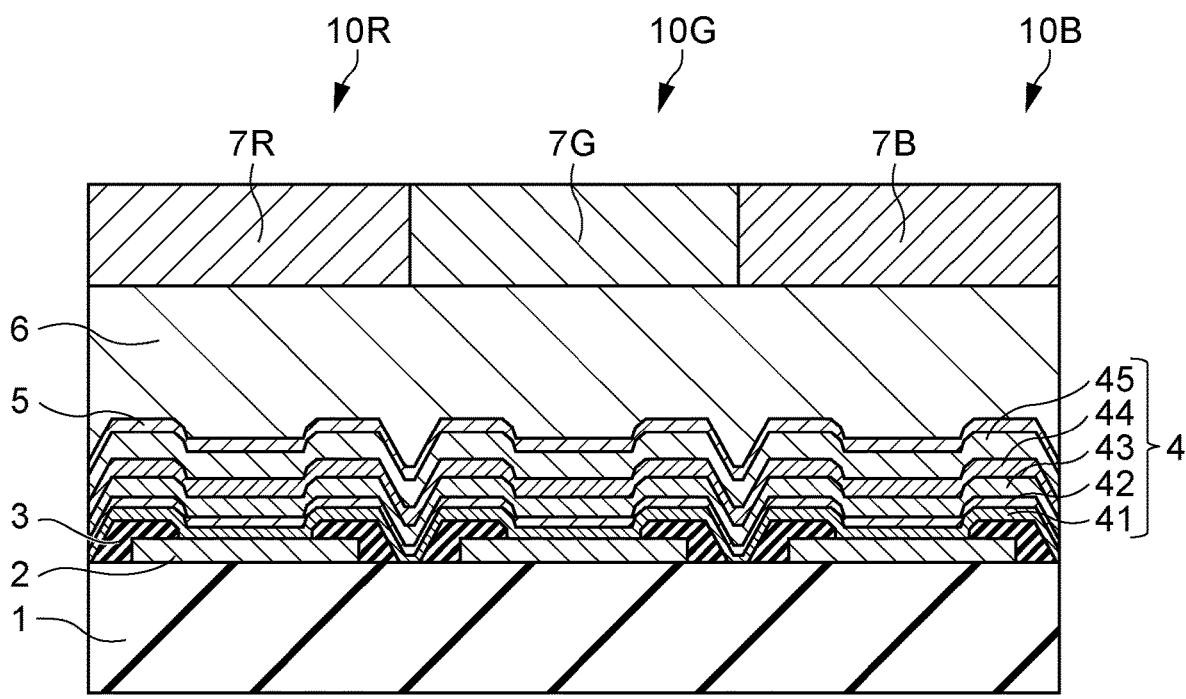
FIG. 2A is a schematic sectional view illustrating an example of a pixel of a display apparatus according to an embodiment of the present disclosure.

FIG. 2A is a schematic sectional view illustrating an example of a pixel constituting a display apparatus according to this embodiment. The pixel has subpixels 10. The subpixels are classified into subpixels 10R, 10G, and 10B in accordance with their light emission. The emission color may be differentiated by the wavelength of light emitted from a light-emitting layer. Alternatively, light emitted from subpixels may be selectively transmitted through a color filter or the like or subjected to color conversion by a color filter or the like. Each of the subpixels includes, on an interlayer insulating layer 1, a reflective electrode 2 serving as a first electrode, an insulating layer 3 that covers the edge of the reflective electrode 2, an organic compound layer 4 that covers the first electrode and the insulating layer, a transparent electrode 5, a protective layer 6, and a color filter 7.

The interlayer insulating layer 1 may include a transistor and a capacitor element below or inside the interlayer insulating layer 1. The transistor and the first electrode may be electrically connected to each other through a contact hole (not illustrated) or the like.

The insulating layer 3 is also referred to as a bank or a pixel-separating film. The insulating layer 3 is disposed so as to cover the edge of the first electrode and surround the first electrode. The organic compound layer 4 is in contact with a portion in which the insulating layer is not disposed. This portion serves as a light-emitting region.

The organic compound layer 4 includes a hole injection layer 41, a hole transport layer 42, a first light-emitting layer 43, a second light-emitting layer 44, and an electron transport layer 45.

The second electrode 5 may be a transparent electrode, a reflective electrode, or a semitransparent electrode.

The protective layer 6 suppresses the permeation of water into the organic compound layer. The protective layer is illustrated as if having a single-layer structure, but may be constituted by a plurality of layers. The layers may be constituted by an inorganic compound layer and an organic compound layer.

The color filter 7 is classified into color filters 7R, 7G, and 7B in accordance with its color. The color filter may be formed on a planarizing film (not illustrated). A resin protective layer (not illustrated) may be disposed on the color filter. The color filter may be formed on the protective layer 6. The color filter may be bonded after the color filter is formed on a counter substrate such as a glass substrate.

Figure 2B:
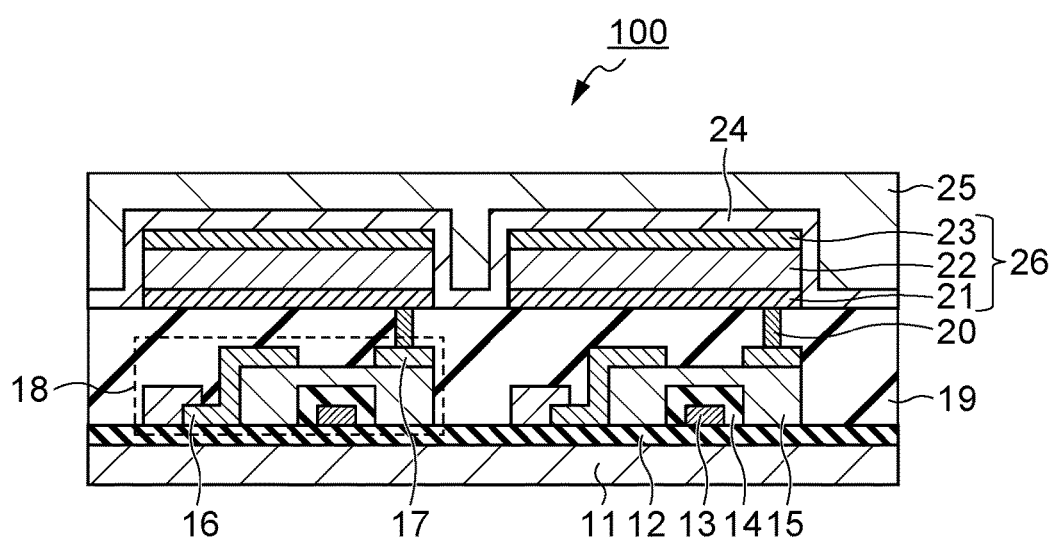
FIG. 2B is a schematic sectional view illustrating an example of a display apparatus including an organic light-emitting element according to an embodiment of the present disclosure.

FIG. 2B is a schematic sectional view illustrating an example of a display apparatus including organic light-emitting elements and transistors connected to the organic light-emitting elements. The transistor is an example of active elements. The transistor may be a thin film transistor (TFT).

A display apparatus 100 in FIG. 2B includes a substrate 11 made of, for example, glass or silicon and an insulating layer 12 disposed on the substrate 11. An active element 18 such as a TFT is disposed on the insulating layer, and the active element 18 is constituted by a gate electrode 13, a gate insulating film 14, and a semiconductor layer 15. The TFT 18 is also constituted by the semiconductor layer 15, a drain electrode 16, and a source electrode 17. An insulating film 19 is disposed on the TFT 18. An anode 21 that constitutes an organic light-emitting element and the source electrode 17 are connected to each other through a contact hole 20 disposed in the insulating film.

The form of electrical connection between electrodes (anode and cathode) included in the organic light-emitting element and electrodes (source electrode and drain electrode) included in the TFT is not limited to the form illustrated in FIG. 2B. That is, it suffices that one of the anode and the cathode is electrically connected to one of the source electrode and the drain electrode of the TFT. The TFT refers to a thin film transistor.

In the display apparatus 100 in FIG. 2B, an organic compound layer 22 is illustrated as if having a single-layer structure, but may have a multilayer structure. A first protective layer 24 and a second protective layer 25 for suppressing the deterioration of the organic light-emitting element are disposed on the cathode 23.

In the display apparatus 100 in FIG. 2B, a transistor is used as a switching element. Instead, another switching element may be used.

The transistor used in the display apparatus 100 in FIG. 2B is not limited to transistors that use a single-crystal silicon wafer, but may be thin-film transistors including an active layer on an insulating surface of a substrate. Examples of the active layer include single-crystal silicon, amorphous silicon, non-single-crystal silicon such as microcrystalline silicon, and non-single-crystal oxide semiconductors such as indium zinc oxide and indium gallium zinc oxide. The thin-film transistors are also referred to as TFT elements.

The transistor included in the display apparatus 100 in FIG. 2B may be formed in a substrate such as a Si substrate. Herein, the phrase "formed in a substrate" means that a transistor is produced by processing the substrate itself, such as a Si substrate. That is, a transistor formed in a substrate can be regarded as a transistor integrally formed with a substrate.

In the organic light-emitting element according to this embodiment, the emission luminance is controlled by a TFT that is an example of a switching element. When a plurality of such organic light-emitting elements are arranged in a plane, an image can be displayed using an emission luminance of each of the organic light-emitting elements. The switching element according to this embodiment is not limited to TFTs. The switching element may be a transistor formed of low-temperature polysilicon or an active matrix driver formed on a substrate such as a Si substrate. The phrase "on a substrate" may also refer to "in a substrate". The size of a display unit determines whether a transistor is disposed in a substrate or a TFT is used. For example, in the case of a size of about 0.5 inches, the organic light-emitting element may be disposed on a Si substrate.

Figure 3:
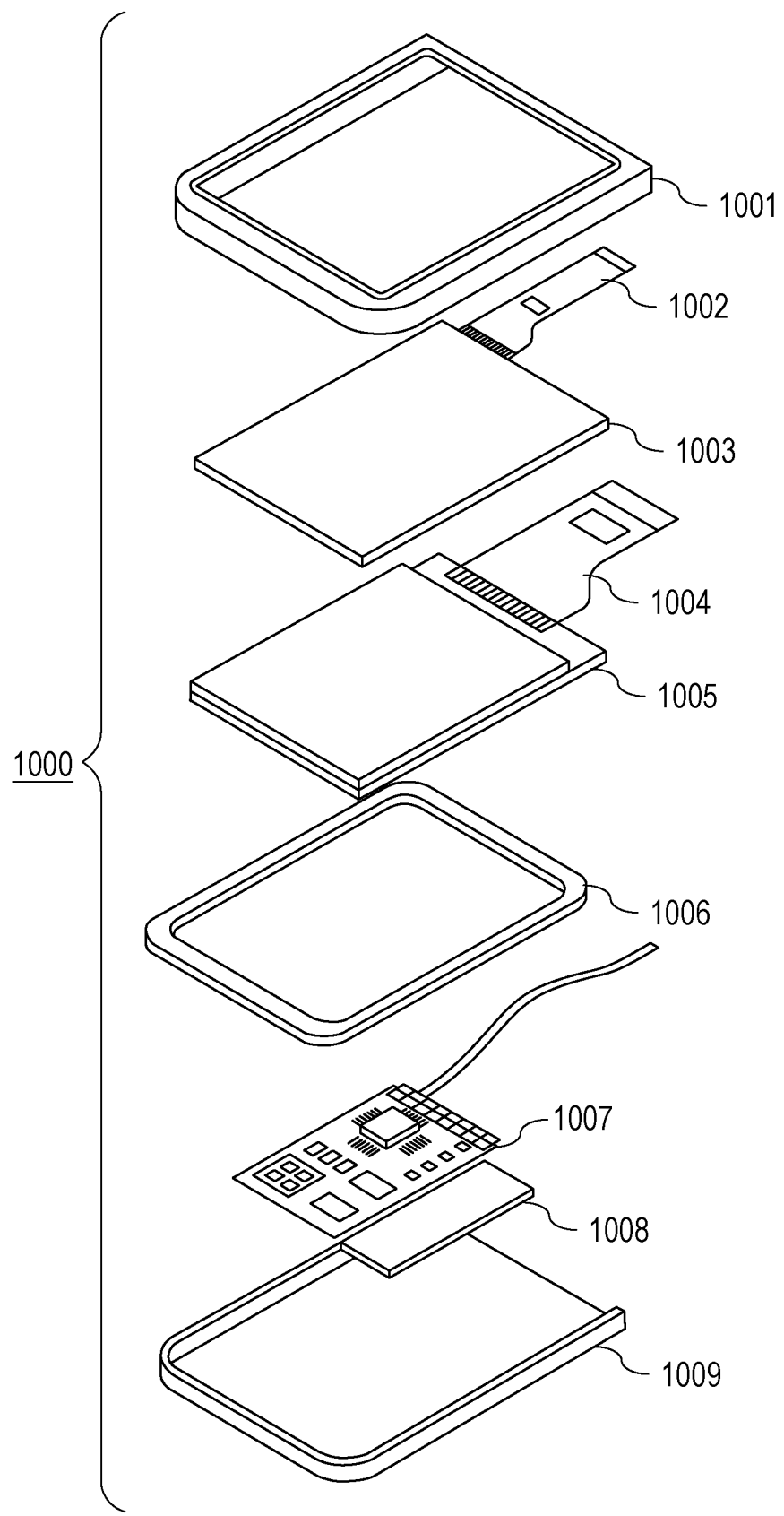
FIG. 3 schematically illustrates an example of a display apparatus including an organic light-emitting element according to an embodiment of the present disclosure.

FIG. 3 schematically illustrates an example of a display apparatus according to this embodiment. A display apparatus 1000 may include a touch panel 1003, a display panel 1005, a frame 1006, a circuit board 1007, and a battery 1008 between an upper cover 1001 and a lower cover 1009. Flexible printed circuits FPC 1002 and 1004 are connected to the touch panel 1003 and the display panel 1005, respectively. A transistor is printed on the circuit board 1007. The battery 1008 is not necessarily disposed if the display apparatus is not a mobile apparatus. Even if the display apparatus is a mobile apparatus, the battery 1008 may be disposed at a different position.

The display apparatus according to this embodiment may include red, green, and blue color filters. The red, green, and blue color filters may be disposed in a delta arrangement.

The display apparatus according to this embodiment may be used in a display unit of a mobile terminal. The display unit may have both a display function and an operational function. Examples of the mobile terminal include cellular phones such as smartphones, tablet computers, and head-mounted displays.

The display apparatus according to this embodiment may be used in a display unit of an image pickup apparatus that includes an optical unit including a plurality of lenses and an image pickup element configured to receive light that has passed through the optical unit. The image pickup apparatus may include a display unit configured to display information obtained by the image pickup element. The display unit may be a display unit exposed to the outside of the image pickup apparatus or a display unit disposed in a viewfinder. The image pickup apparatus may be a digital camera or a digital camcorder. The image pickup apparatus can also be referred to as a photoelectric conversion apparatus.

Figure 4A:
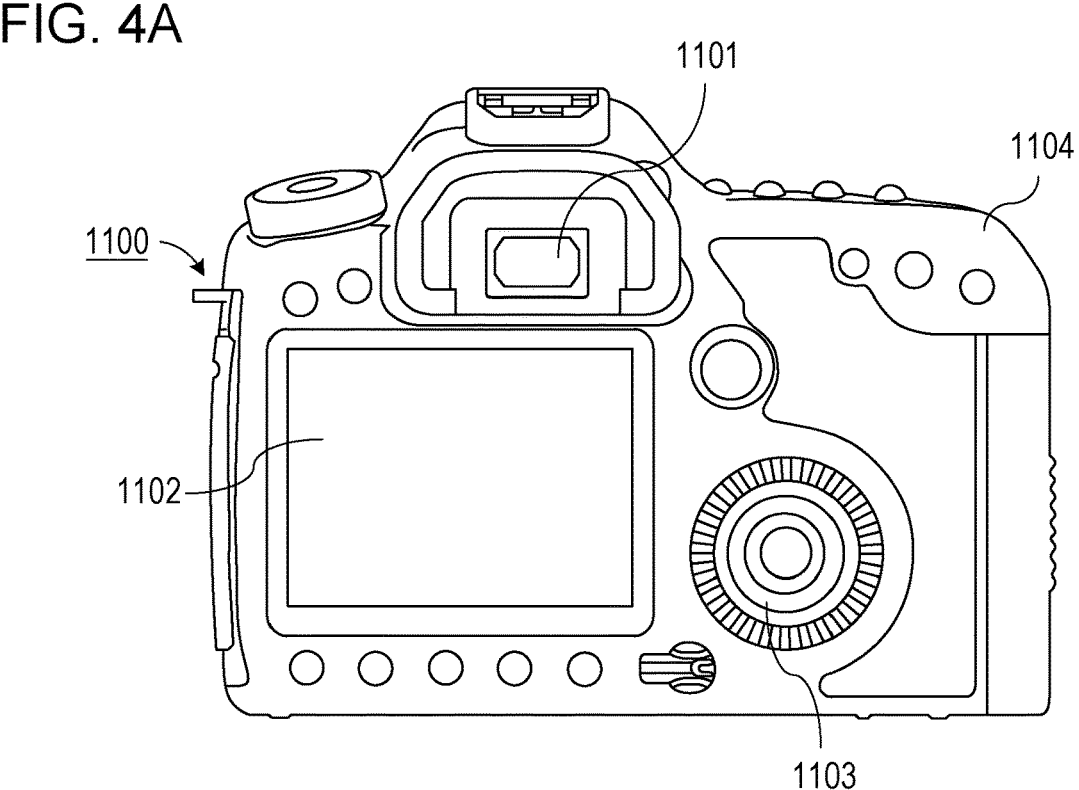
FIG. 4A schematically illustrates an example of an image pickup apparatus according to an embodiment of the present disclosure.

FIG. 4A schematically illustrates an example of an image pickup apparatus according to this embodiment. An image pickup apparatus 1100 may include a viewfinder 1101, a rear display 1102, an operating unit 1103, and a housing 1104. The viewfinder 1101 may include the display apparatus according to this embodiment. In this case, the display apparatus may display not only an image to be captured, but also environmental information, image capturing instructions, and the like. The environmental information may be, for example, the intensity of external light, the direction of external light, the moving speed of a subject, and the possibility that the subject is hidden by an object.

Since the timing appropriate for capturing an image is only a moment, the information is desirably displayed as quickly as possible. Therefore, the display apparatus including the organic light-emitting element according to an embodiment of the present disclosure can be used. This is because the organic light-emitting element has a high response speed. The display apparatus including the organic light-emitting element can be more suitably used than these apparatuses and liquid crystal display apparatuses that are required to have a high display speed.

The image pickup apparatus 1100 includes an optical unit (not illustrated). The optical unit includes a plurality of lenses and focuses an image on the image pickup element accommodated in the housing 1104. By adjusting the relative positions of the plurality of lenses, the focal point can be adjusted. This operation can also be performed automatically.

Figure 4B:
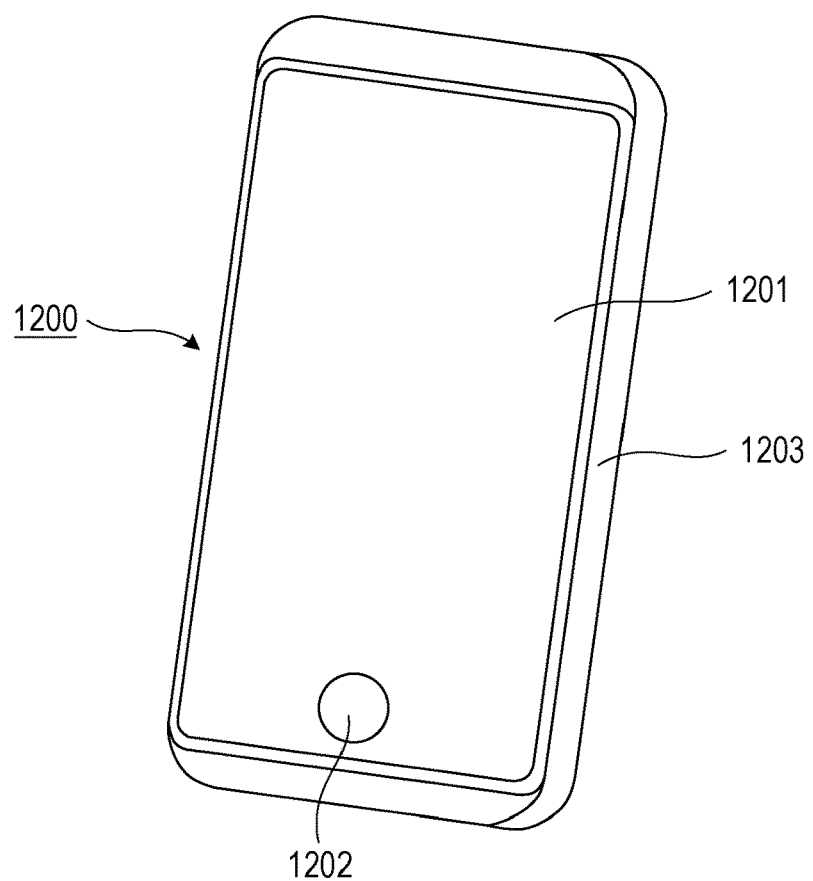
FIG. 4B schematically illustrates an example of a mobile apparatus according to an embodiment of the present disclosure.

FIG. 4B schematically illustrates an example of an electronic apparatus according to this embodiment. An electronic apparatus 1200 includes a display unit 1201, an operating unit 1202, and a housing 1203. The housing 1203 may include a circuit, a printed board including the circuit, a battery, and a communication unit. The operating unit 1202 may be a button or a touch panel response unit. The operating unit may be a biometric authentication unit that releases a lock through recognition of fingerprints. An electronic apparatus including a communication unit may be referred to as a communication apparatus. The electronic apparatus may further include a lens and an image pickup element so as to have a camera function. An image captured by the camera function is displayed on the display unit. Examples of the electronic apparatus include smartphones and notebook computers.

Figure 5A:
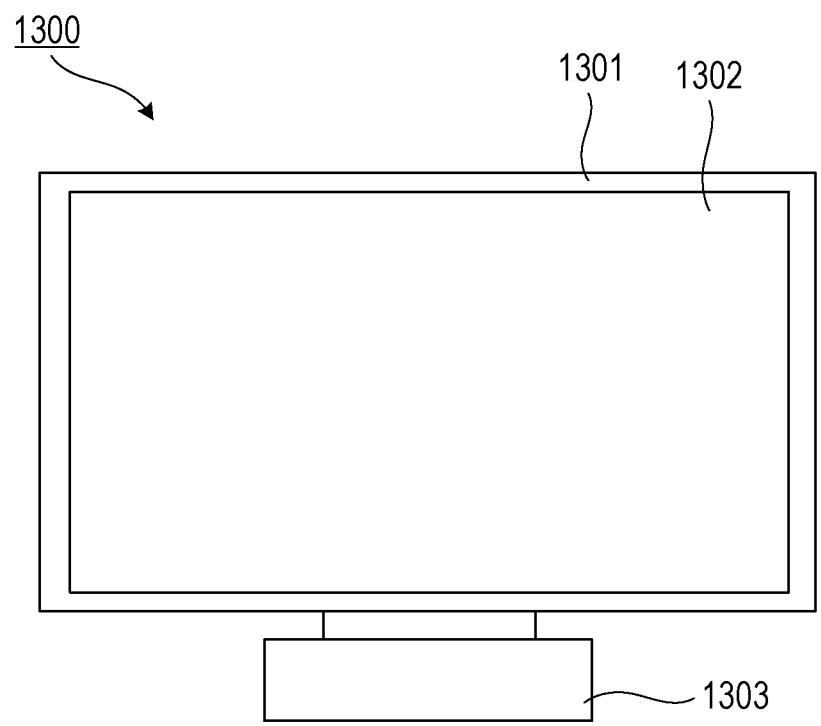
FIG. 5A schematically illustrates an example of a display apparatus according to an embodiment of the present disclosure.
Figure 5B:
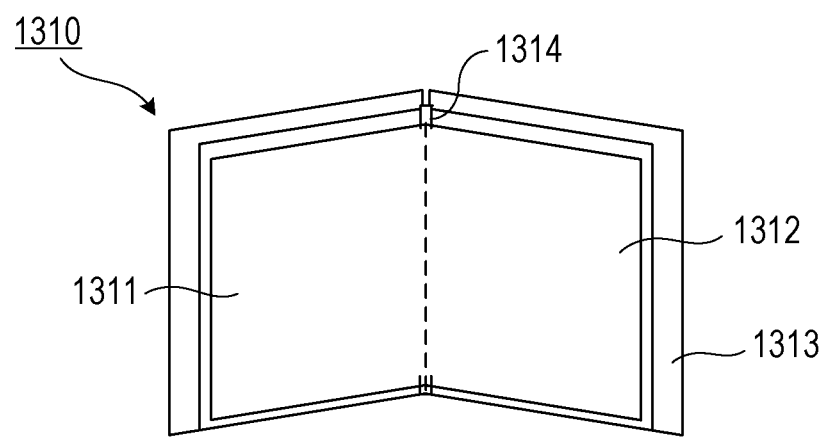
FIG. 5B schematically illustrates an example of a foldable display apparatus.

FIGS. 5A and 5B schematically illustrate examples of display apparatuses according to this embodiment. FIG. 5A illustrates a display apparatus such as a television monitor or a PC monitor. A display apparatus 1300 includes a frame 1301 and a display unit 1302. A light-emitting device according to this embodiment may be used for the display unit 1302.

The display apparatus 1300 includes the frame 1301 and a base 1303 that supports the display unit 1302. The form of the base 1303 is not limited to that in FIG. 5A. The lower side of the frame 1301 may also serve as a base.

The frame 1301 and the display unit 1302 may be curved. The radius of curvature may be 5000 mm or more and 6000 mm or less.

FIG. 5B schematically illustrates another example of the display apparatus according to this embodiment. A display apparatus 1310 in FIG. 5B is a so-called foldable display apparatus. The display apparatus 1310 includes a first display unit 1311, a second display unit 1312, a housing 1313, and a bending point 1314. The first display unit 1311 and the second display unit 1312 may include the light-emitting device according to this embodiment. The first display unit 1311 and the second display unit 1312 may constitute a single seamless display apparatus. The first display unit 1311 and the second display unit 1312 can be divided by the bending point. The first display unit 1311 and the second display unit 1312 may display different images or a single image may be displayed in a combination of the first and second display units.

Figure 6A:
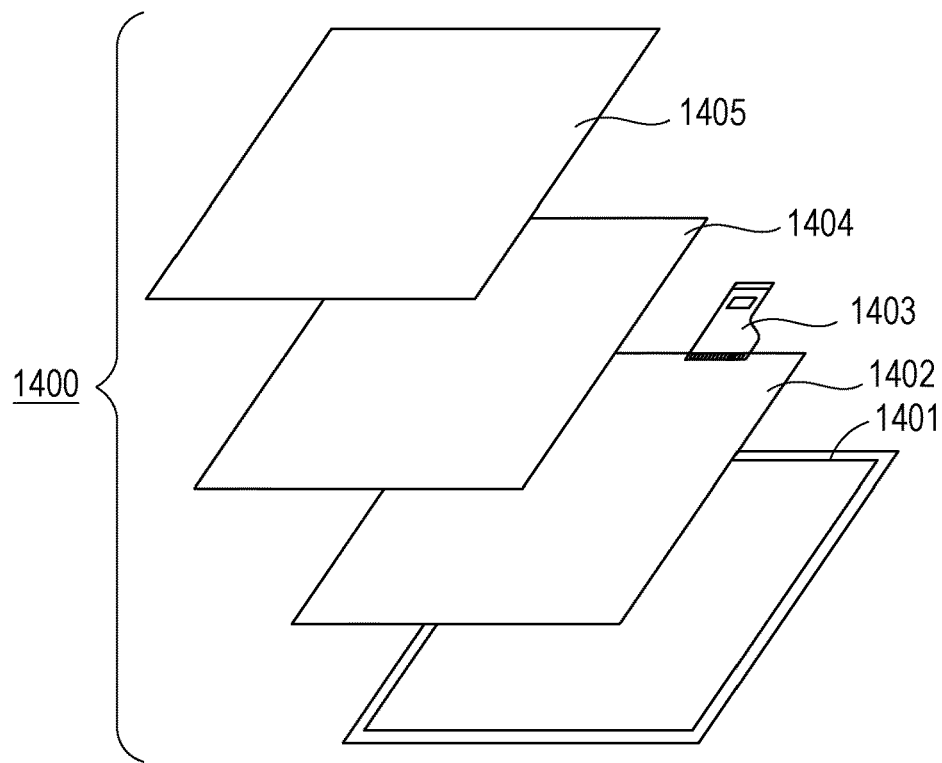
FIG. 6A schematically illustrates an example of a lighting apparatus according to an embodiment of the present disclosure.

FIG. 6A schematically illustrates an example of a lighting apparatus according to this embodiment. A lighting apparatus 1400 may include a housing 1401, a light source 1402, a circuit board 1403, an optical film 1404, and a light diffusion unit 1405. The light source may include the organic light-emitting element according to this embodiment. The optical film may be a filter for improving the color rendering of the light source. The light diffusion unit used for lighting up or the like effectively diffuses light from the light source and allows the light to reach a wide area. The optical film and the light diffusion unit may be disposed on the light-emitting side of the lighting apparatus. A cover may be optionally disposed on the outermost part.

The lighting apparatus is, for example, an apparatus that lights a room. The lighting apparatus may emit light of white, natural white, or any other color from blue to red. The lighting apparatus may include a light modulation circuit configured to modulate the light. The lighting apparatus may include the organic light-emitting element according to an embodiment of the present disclosure and a power supply circuit connected to the organic light-emitting element. The power supply circuit is a circuit that converts an alternating voltage to a direct voltage. The color "white" has a color temperature of 4200 K and the color "natural white" has a color temperature of 5000 K. The lighting apparatus may include a color filter.

The lighting apparatus according to this embodiment may include a heat dissipation unit. The heat dissipation unit dissipates heat in the apparatus to the outside and is formed of, for example, a metal having a high specific heat or a liquid silicon.

Figure 6B:
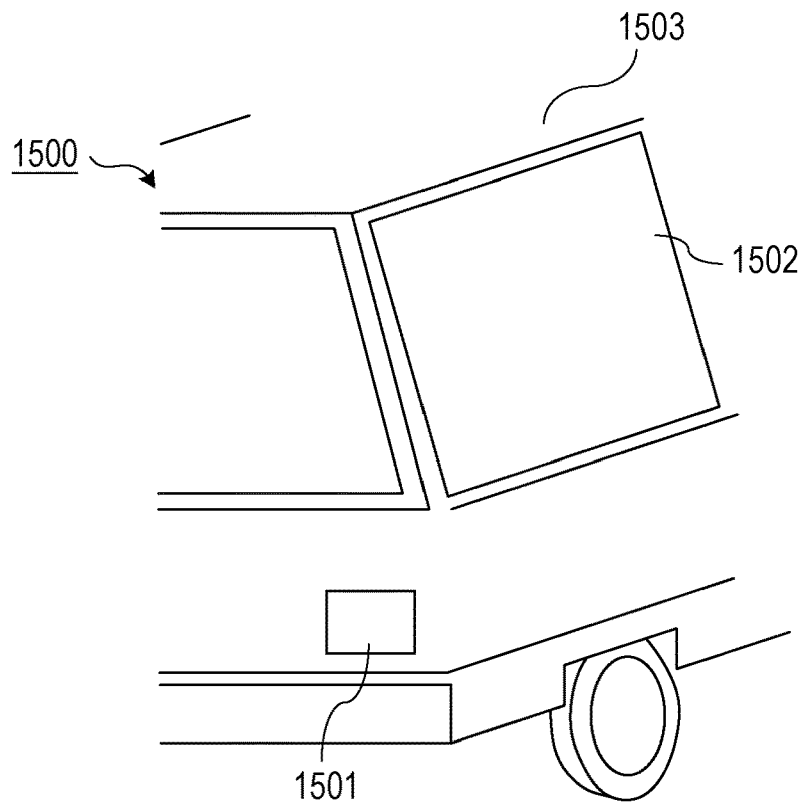
FIG. 6B schematically illustrates an automobile that is an example of a moving object according to an embodiment of the present disclosure.

FIG. 6B schematically illustrates an automobile that is an example of a moving object according to this embodiment. The automobile includes a tail lamp that is an example of a lighting fixture. An automobile 1500 includes a tail lamp 1501, and the tail lamp may be lit through, for example, application of the brake.

The tail lamp 1501 may include the organic light-emitting element according to this embodiment. The tail lamp may include a protective member that protects the organic EL element. The protective member may be made of any material as long as the protective member has a relatively high strength and transparency. The protective member may be made of polycarbonate or the like. The polycarbonate may be mixed with, for example, a furandicarboxylic acid derivative or an acrylonitrile derivative.

The automobile 1500 may include a car body 1503 and windows 1502 attached to the car body 1503. The windows may be transparent displays as long as the windows are not a front or rear window of the automobile. The transparent display may include the organic light-emitting element according to this embodiment. In this case, members, such as an electrode, included in the organic light-emitting element are formed of a transparent material.

The moving object according to this embodiment may be, for example, a ship, an aircraft, or a drone. The moving object may include a body and a lighting fixture disposed on the body. The lighting fixture may emit light for allowing the position of the body to be recognized. The lighting fixture may include the organic light-emitting element according to this embodiment.

As described above, use of an apparatus including the organic light-emitting element according to this embodiment allows stable display with a good image quality for a long time.

EXAMPLES

Hereafter, the present disclosure will be described based on Examples. However, the present disclosure is not limited thereto. In Examples, bis(dibenzylideneacetone)palladium (0) is abbreviated as Pd(dba)$_2$, tricyclohexylphosphine is abbreviated as P(Cy)$_3$, N-chlorosuccinimide is abbreviated as NCS, N,N-dimethylformamide is abbreviated as DMF, dimethylsulfoxide is abbreviated as DMSO, dimethylacetamide is abbreviated as DMAc, and diazabicycloundecene is abbreviated as DBU in some cases.

Example 1 (Synthesis of Exemplary Compound D-4)

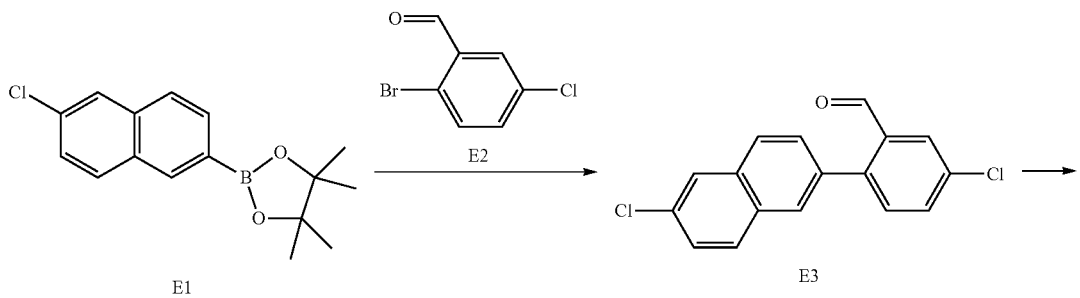

-continued
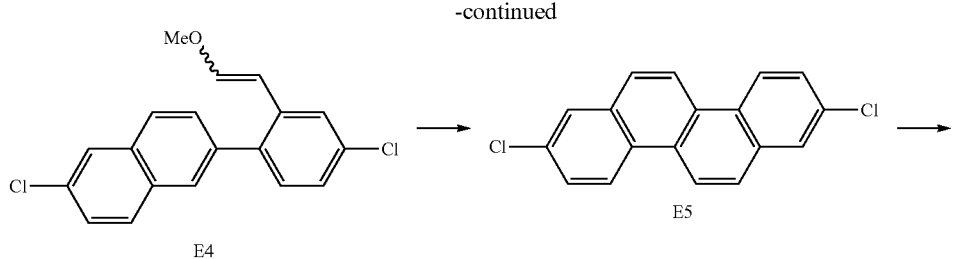
E4 → E5 →
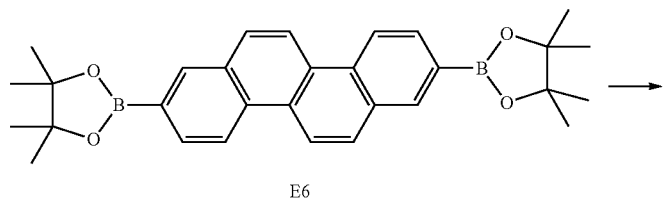
E6 →
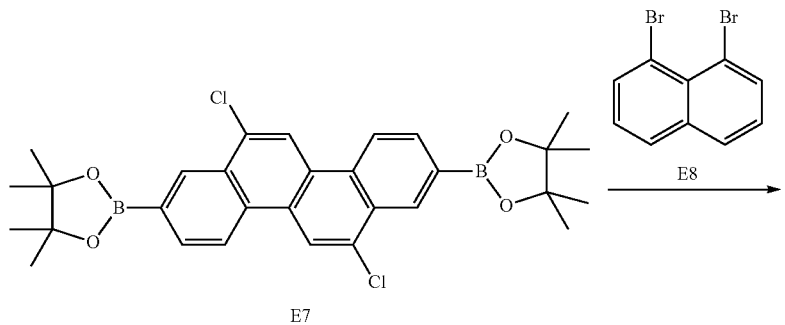
E7
E8
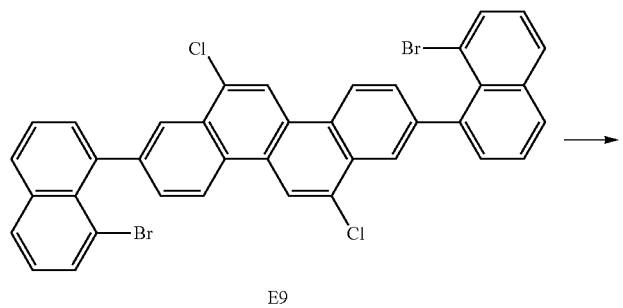
E9 →
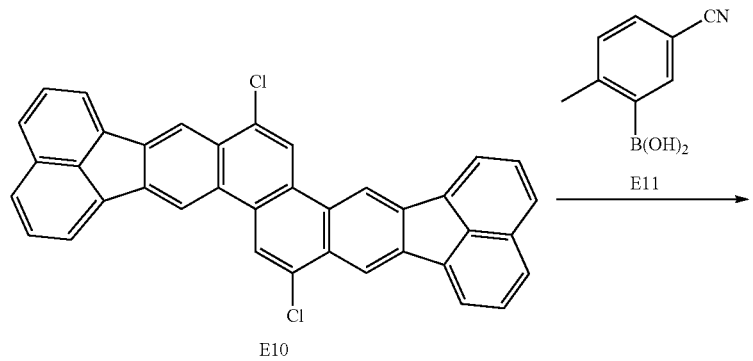
E10
E11

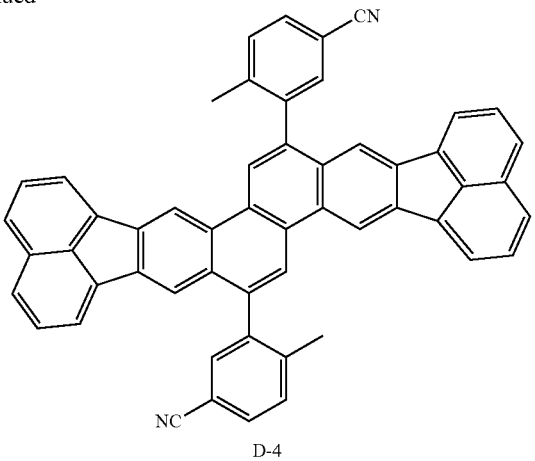

D-4

(1) Synthesis of Compound E3

The following reagents and solvents were charged into a 500 ml recovery flask.
- Compound E1: 7.23 g (25.1 mmol)
- Compound E2: 5.00 g (22.8 mmol)
- Pd(PPh$_3$)$_4$: 790 mg (1.14 mmol)
- Sodium carbonate: 9.66 g (91.2 mmol)
- Toluene: 200 ml
- Ethanol: 100 ml
- Water: 100 ml Subsequently, the reaction solution was heated to 90° C. in a nitrogen stream, and stirring was performed at this temperature (90° C.) for 5 hours. After the completion of the reaction, extraction was performed using toluene and water. The resulting product was concentrated, purified by silica gel column chromatography (heptane:toluene=1:1), and then washed by dispersion with methanol to obtain 5.5 g of a white compound E3 (yield: 80%).

(2) Synthesis of Compound E4

The following reagent and solvent were charged into a 200 ml recovery flask.
- (Methoxymethyl)triphenylphosphonium chloride: 12.8 g (41.5 mmol)
- Tetrahydrofuran: 50 ml Subsequently, the following reagent was gradually added dropwise to the reaction solution in a nitrogen stream at room temperature.
- Potassium t-butoxide [1.0 M tetrahydrofuran solution]

Subsequently, the reaction solution was stirred at this temperature (room temperature) for 1 hour, and then the following mixed solution was gradually added dropwise thereto at room temperature.
- Compound E3: 5.0 g (16.6 mmol)
- Tetrahydrofuran: 50 ml After the completion of the reaction, extraction was performed using toluene and water. The resulting product was concentrated, purified by silica gel column chromatography (heptane:toluene=1:1), and then washed by dispersion with methanol to obtain 4.48 g of a white compound E4 (yield: 82%).

(3) Synthesis of Compound E5

The following reagent and solvent were charged into a 200 ml recovery flask.
- Compound E4: 4.00 g (12.1 mmol)
- Dichloromethane: 100 ml Subsequently, the reaction solution was cooled to 0° C. in a nitrogen stream, and the following reagent was added dropwise to the reaction solution.
- Methanesulfonic acid: 1.75 g (18.2 mmol)

Subsequently, the reaction solution was stirred at room temperature for 3 hours. After the completion of the reaction, 50 ml of methanol was added thereto and stirring was performed at 0° C. for 30 minutes. The resulting product was then separated and washed with water and methanol to obtain 3.09 g of a white compound E5 (yield: 86%).

(4) Synthesis of Compound E6

The following reagents and solvent were charged into a 500 ml recovery flask.
- Compound E5: 3.00 g (10.1 mmol)
- bis(pinacolborane): 10.3 g (40.4 mmol)
- Pd(dba)$_2$: 580 mg (1.01 mmol)
- P(Cy)$_3$: 850 mg (3.03 mmol)
- Potassium acetate: 3.96 mg (40.4 mmol)
- o-Xylene: 300 ml Subsequently, the reaction solution was heated to 150° C. in a nitrogen stream, and stirring was performed at this temperature (150° C.) for 7 hours. After the completion of the reaction, celite filtration was performed. The resulting product was concentrated and washed by dispersion with heptane to obtain 3.93 g of a white compound E6 (yield: 81%).

(5) Synthesis of Compound E7

The following reagents and solvent were charged into a 500 ml recovery flask.
- Compound E6: 3.8 g (7.91 mmol)
- NCS: 5.28 g (39.6 mmol)
- Methanesulfonic acid: 227 mg (2.37 mmol)
- DMF: 380 ml Subsequently, the reaction solution was heated to 65° C. in a nitrogen stream, and stirring was performed at this temperature (65° C.) for 7 hours. After the completion of the reaction, filtration was performed. The resulting product was purified by silica gel column chromatography (toluene) and then washed by dispersion with heptane to obtain 2.17 g of a white compound E7 (yield: 50%).

(6) Synthesis of Compound E9

The following reagents and solvent were charged into a 200 ml recovery flask.
- Compound E7: 2.00 g (3.64 mmol)
- Compound E8: 4.17 g (14.6 mmol)
- Pd(PPh$_3$)$_2$Cl$_2$: 128 mg (0.18 mmol)

Sodium carbonate: 1.54 g (14.6 mmol)
DMSO: 100 ml

Subsequently, the reaction solution was heated to 90° C. in a nitrogen stream, and stirring was performed at this temperature (90° C.) for 5 hours. After the completion of the reaction, 100 ml of methanol was added thereto and stirring was performed at room temperature for 30 minutes. After that, filtration was performed. The resulting product was purified by silica gel column chromatography (heptane:chlorobenzene=3:1) and then washed by dispersion with methanol to obtain 1.24 g of a white compound E9 (yield: 48%).

(7) Synthesis of Compound E10

The following reagents and solvent were charged into a 100 ml recovery flask.

Compound E9: 1.00 g (1.41 mmol)
Pd(dba)$_2$: 81 mg (0.14 mmol)
P(Cy)$_3$: 119 mg (0.42 mmol)
Potassium acetate: 415 mg (4.23 mmol)
DMAc: 50 ml Subsequently, the reaction solution was heated to 170° C. in a nitrogen stream, and stirring was performed at this temperature (170° C.) for 2 hours. After the completion of the reaction, filtration was performed. The resulting product was washed by dispersion with heptane/toluene to obtain 523 mg of a dark green compound E11 (yield: 68%).

(8) Synthesis of Exemplary Compound D-4

The following reagents and solvent were charged into a 200 ml recovery flask.

Compound E10: 100 mg (0.18 mmol)
Compound E11: 96 mg (0.60 mmol)

Pd(OAc)$_2$: 4 mg (0.02 mmol)
s-phos: 18 mg (0.05 mmol)
Potassium carbonate: 149 g (1.08 mmol)
DMSO: 10 ml Subsequently, the reaction solution was heated to 100° C. in a nitrogen stream, and stirring was performed at this temperature (100° C.) for 6 hours. After the completion of the reaction, 100 ml of methanol was added thereto and stirring was performed at room temperature for 30 minutes. After that, filtration was performed. The resulting product was purified by silica gel column chromatography (chlorobenzene) and then washed by dispersion with heptane/toluene to obtain 82 mg of a yellow exemplary compound D-4 (yield: 65%).

The emission spectrum of a toluene solution of the exemplary compound D-4 at $1\times10^{-5}$ mol/L was determined by photoluminescence measurement at an excitation wavelength of 350 nm using an F-4500 manufactured by Hitachi, Ltd. As a result, a spectrum having the maximum intensity at 441 nm was obtained.

The exemplary compound D-4 was subjected to mass spectrometry using MALDI-TOF-MS (Autoflex LRF manufactured by Bruker).

MALDI-TOF-MS

Measured value: m/z=706, Calculated value: $C_{54}H_{30}N_2$=706

Example 2 (Synthesis of Exemplary Compound D-26)

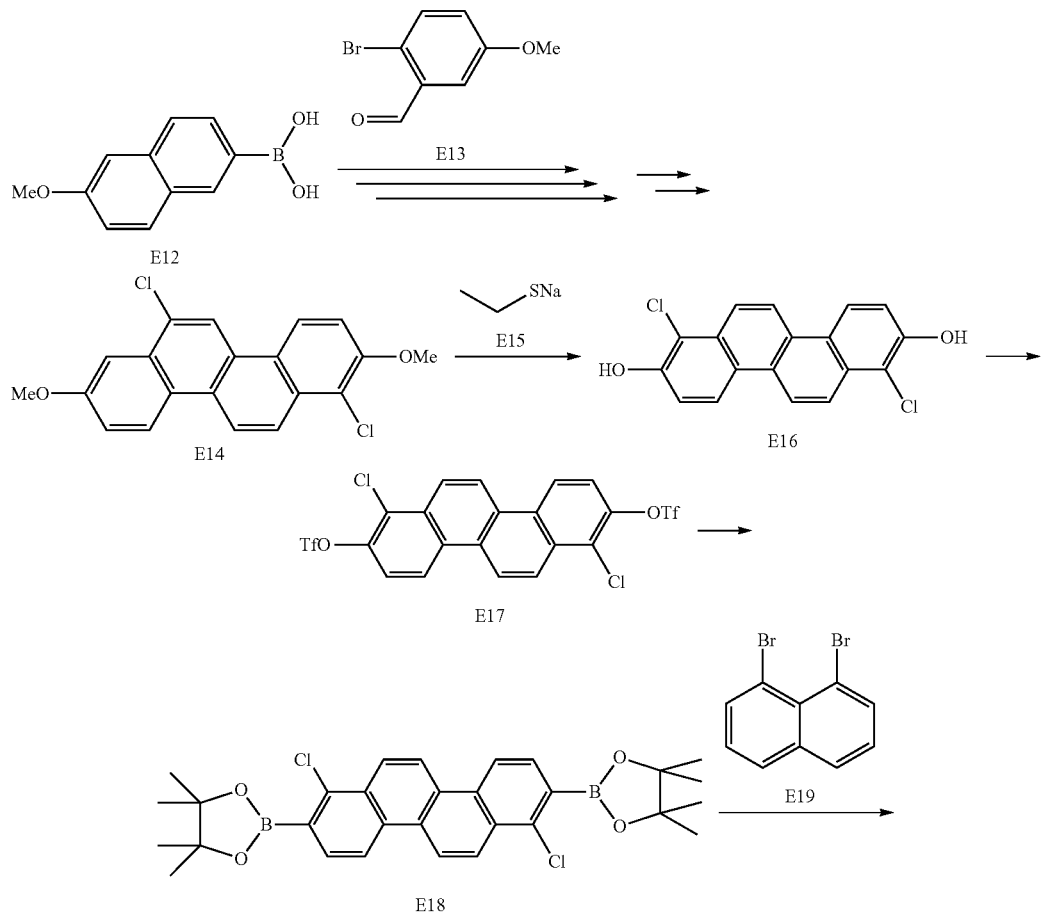

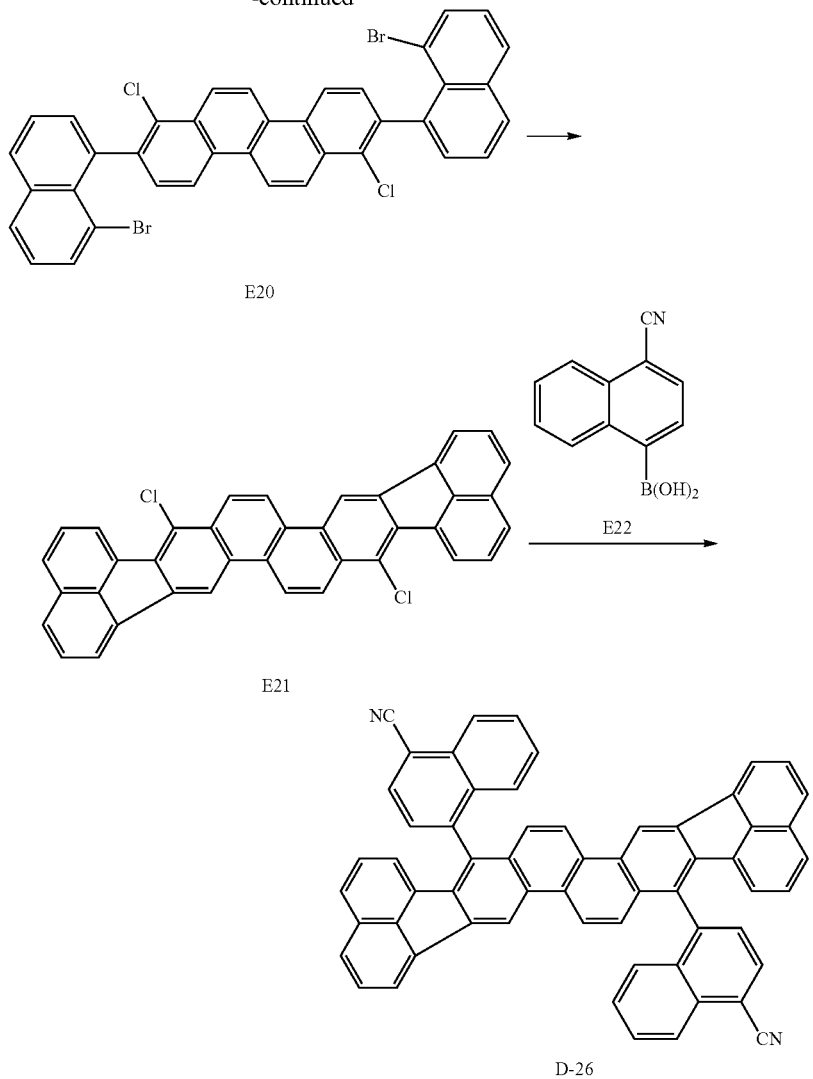

(1) Synthesis of Compound E14

An intermediate E14 was synthesized in the same manner as in Example 1, except that E1 was changed to E12 and E2 was changed to E13. Since the reaction from E12 to E14 is the same as that in Example 1, intermediates are not described and only arrows are described.

(2) Synthesis of Compound E16

The following reagents and solvent were charged into a 500 ml recovery flask.

Compound E14: 3.6 g (10.0 mmol)
Sodium ethanethiolate: 3.36 g (40.0 mmol)
DMF: 280 ml Subsequently, the reaction solution was heated to 60° C. in a nitrogen stream, and stirring was performed at this temperature for 7 hours. After the completion of the reaction, an aqueous ammonium chloride solution was added thereto, and filtration was performed. The resulting product was washed by dispersion with 100 ml of water to obtain 2.46 g of a white compound E16 (yield: 75%).

(3) Synthesis of Compound E17

The following reagents and solvent were charged into a 500 ml recovery flask.

Compound E16: 2.4 g (7.29 mmol)
Trifluoromethanesulfonic anhydride: 4.78 ml (29.1 mmol)
Pyridine: 3.5 ml
Methylene chloride: 240 ml Subsequently, 4.78 ml (29.1 mmol) of trifluoromethanesulfonic anhydride was added dropwise to the reaction solution under ice-cold conditions, and stirring was performed at room temperature for 2 hours. After the completion of the reaction, 200 ml of ice water was added thereto and the organic layer was extracted. The organic layer was concentrated and purified by silica gel column chromatography (mixture of toluene and heptane) to obtain 3.54 g of a white compound E17 (yield: 82%).

(4) Synthesis of Compound E18

The following reagents and solvent were charged into a 500 ml recovery flask.

Compound E17: 3.5 g (6.37 mmol)
bis(pinacolborane): 9.71 g (38.2 mmol)
Pd(dppf)$_2$Cl$_2$: 453 mg (0.637 mmol)
Potassium acetate: 2.50 g (25.5 mmol)
Dioxane: 200 ml Subsequently, the reaction solution was heated to 100° C. in a nitrogen stream, and stirring was performed at this temperature for 7 hours. After the completion of the reaction, celite filtration was performed. The resulting product was concentrated and washed by dispersion with heptane to obtain 3.18 g of a gray compound E18 (yield: 91%).

(5) Synthesis of Compound E20

The following reagents and solvent were charged into a 200 ml recovery flask.

Compound E18: 2.00 g (2.83 mmol)
Compound E19: 2.43 g (8.48 mmol)
Pd(PPh$_3$)$_2$Cl$_2$: 199 mg (0.28 mmol)
Sodium carbonate: 1.80 g (17.0 mmol)
DMSO: 100 ml Subsequently, the reaction solution was heated to 90° C. in a nitrogen stream, and stirring was performed at this temperature for 5 hours. After the completion of the reaction, 100 ml of water was added thereto and stirring was performed at room temperature for 30 minutes. After that, filtration was performed. The resulting product was purified by silica gel column chromatography (mixture of heptane and chlorobenzene) and then washed by dispersion with methanol to obtain 0.76 g of a yellow compound E20 (yield: 38%).

(6) Synthesis of Compound E21

The following reagents and solvents were charged into a 100 ml recovery flask.

Compound E20: 0.75 g (1.06 mmol)
Pd(PPh$_3$)$_2$Cl$_2$: 77 mg (0.11 mmol)
DBU: 5.0 ml
DMAc: 50 ml Subsequently, the reaction solution was heated to 170° C. in a nitrogen stream, and stirring was performed at this temperature (170° C.) for 2 hours. After the completion of the reaction, filtration was performed. The resulting product was washed by dispersion with heptane/toluene to obtain 417 mg of a dark green compound E21 (yield: 72%).

(7) Synthesis of Exemplary Compound D-26

The following reagents and solvents were charged into a 500 ml recovery flask.

Compound E21: 400 mg (0.18 mmol)
Compound E22: 106 mg (0.54 mmol)
Pd(OAc)$_2$: 4 mg (0.02 mmol)
s-phos: 18 mg (0.05 mmol)
Potassium phosphate: 0.458 g (2.16 mmol)
Xylene: 200 ml
Water: 20 ml Subsequently, the reaction solution was heated to 120° C. in a nitrogen stream, and stirring was performed at this temperature for 7 hours. After the completion of the reaction, filtration was performed. The resulting product was purified by silica gel column chromatography (toluene) and then washed by dispersion with heptane to obtain 42 mg of a yellow exemplary compound D-26 (yield: 30%).

The emission spectrum of a toluene solution of the exemplary compound D-26 at 1×10$^{-5}$ mol/L was determined by photoluminescence measurement at an excitation wavelength of 350 nm using an F-4500 manufactured by Hitachi, Ltd. As a result, a spectrum having the maximum intensity at 443 nm was obtained.

Furthermore, the exemplary compound was subjected to mass spectrometry using MALDI-TOF-MS (Autoflex LRF manufactured by Bruker).

MALDI-TOF-MS

Measured value: m/z=778, Calculated value: C$_{60}$H$_{30}$N$_2$=778

Example 3 (Synthesis of Exemplary Compound E-4)

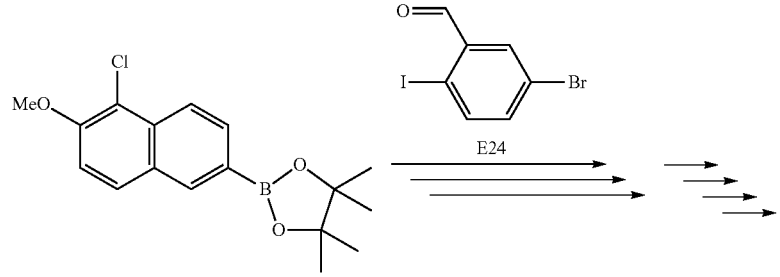

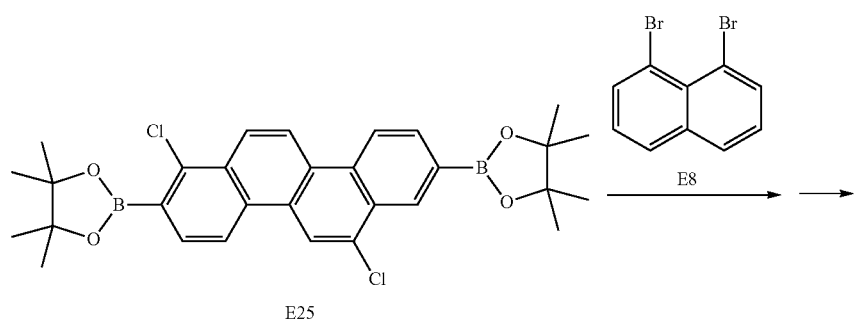

-continued
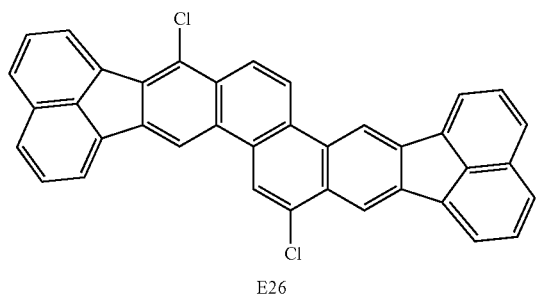
E26
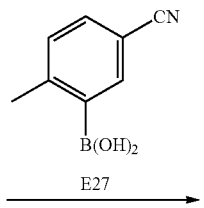
E27
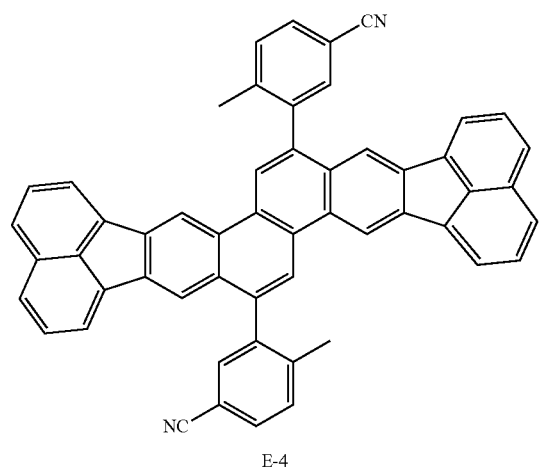
E-4
An exemplary compound E-4 was synthesized with reference to Example 2, except that E12 was changed to E23 and E13 was changed to E24. The measured value of mass spectrometry performed in the same manner as in Example 1 was 706 m/z.
Example 4 (Synthesis of Exemplary Compound D-52)
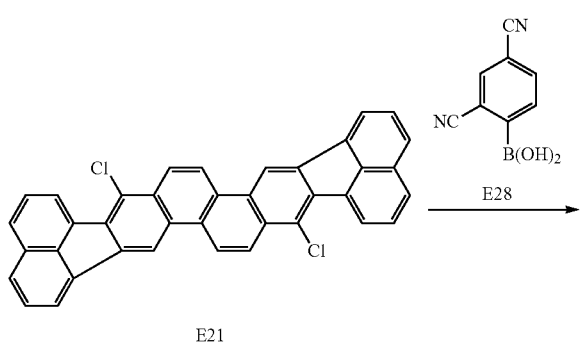
E21
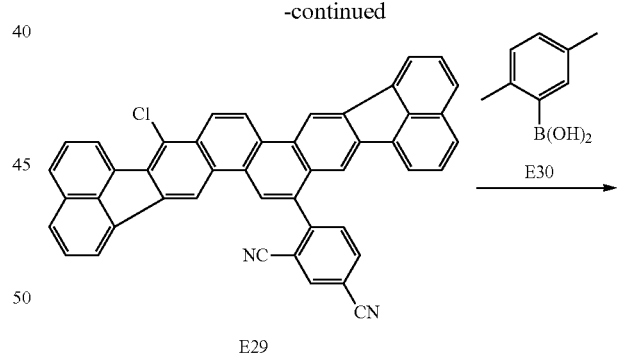
E29
-continued
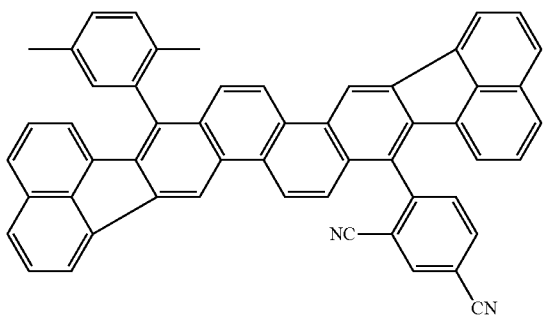
D52
E28

An exemplary compound D-52 was synthesized using the intermediate E21 in Example 2.

(1) Synthesis of Compound E29

The following reagents and solvents were charged into a 500 ml recovery flask.
Compound E21: 400 mg (0.18 mmol)
Compound E28: 62 mg (0.36 mmol)
Pd(OAc)$_2$: 4 mg (0.02 mmol)
s-phos: 18 mg (0.05 mmol)
Potassium phosphate: 0.229 g (1.08 mmol)
Xylene: 200 ml
Water: 20 ml Subsequently, the reaction solution was heated to 120° C. in a nitrogen stream, and stirring was performed at this temperature for 5 hours. After the completion of the reaction, filtration was performed. The resulting product was purified by silica gel column chromatography (toluene) and then washed by dispersion with heptane to obtain 48 mg of a yellow compound E29 (yield: 42%).

(2) Synthesis of Exemplary Compound D-52

The following reagents and solvents were charged into a 50 ml recovery flask.
Compound E29: 46 mg (0.072 mmol)
Compound E30: 43 mg (0.28 mmol)
Pd(OAc)$_2$: 2 mg (0.010 mmol)
s-phos: 11 mg (0.03 mmol)
Potassium phosphate: 0.115 g (0.54 mmol)
Xylene: 20 ml
Water: 2 ml Subsequently, the reaction solution was heated to 120° C. in a nitrogen stream, and stirring was performed at this temperature for 5 hours. After the completion of the reaction, filtration was performed. The resulting product was purified by silica gel column chromatography (toluene) and then washed by dispersion with heptane to obtain 19 mg of a yellow exemplary compound D-52 (yield: 38%).

The emission spectrum of a toluene solution of the exemplary compound D-52 at $1\times10^{-5}$ mol/L was determined by photoluminescence measurement at an excitation wavelength of 350 nm using an F-4500 manufactured by Hitachi, Ltd. As a result, a spectrum having the maximum intensity at 443 nm was obtained.

Furthermore, the exemplary compound was subjected to mass spectrometry using MALDI-TOF-MS (Autoflex LRF manufactured by Bruker).

MALDI-TOF-MS

Measured value: m/z=706, Calculated value: $C_{54}H_{30}N_2$=706

Example 5 (Synthesis of Exemplary Compound D-54)

An exemplary compound D-54 was synthesized in the same manner as in Example 4, except that E25 was changed to E29 and E28 was changed to E30. The measured value of mass spectrometry performed in the same manner as in Example 1 was 748 m/z.

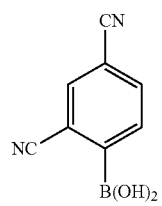

E29

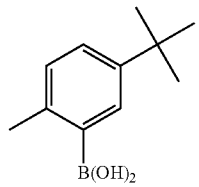

E30

Example 6 (Synthesis of Exemplary Compound D-56)

An exemplary compound D-56 was synthesized in the same manner as in Example 4, except that E25 was changed to E31 and E28 was changed to E32. The measured value of mass spectrometry performed in the same manner as in Example 1 was 692 m/z.

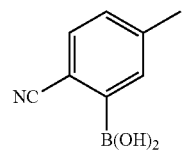

E31

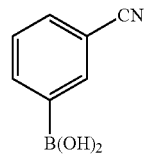

E32

Examples 7 to 27 (Synthesis of Exemplary Compounds)

In these Examples, exemplary compounds were synthesized in the same manner, except that the raw materials in Example 1 or 2 were changed to those listed in raw materials 1 to 4 in Tables 2-1 to 2-3. Specifically, E1 in Example 1 was changed to those listed in the raw material 1, E2 was changed to those listed in the raw material 2, E8 was changed to those listed in the raw material 3, and E11 was changed to those listed in the raw material 4. Furthermore, E12 in Example 2 was changed to those listed in the raw material 1, E13 was changed to those listed in the raw material 2, E19 was changed to those listed in the raw material 3, and E22 was changed to those listed in the raw material 4. The measured value m/z of mass spectrometry performed in the same manner as in Example 1 is also shown.

TABLE 2-1

| Example | Exemplary compound | Raw material 1 | Raw material 2 | Raw material 3 | Raw material 4 | m/z |
|---|---|---|---|---|---|---|
| 7 | D-5 | (6-chloronaphthalen-2-yl pinacol boronate) | 2-bromo-5-chlorobenzaldehyde | 1,8-dibromonaphthalene | 4-cyano-3-methylphenylboronic acid | 706 |
| 8 | D-7 | (6-chloronaphthalen-2-yl pinacol boronate) | 2-bromo-5-chlorobenzaldehyde | 1,8-dibromonaphthalene | 4-cyano-2-isopropylphenylboronic acid | 762 |
| 9 | D-8 | (6-chloronaphthalen-2-yl pinacol boronate) | 2-bromo-5-chlorobenzaldehyde | 1,8-dibromonaphthalene | 4-tert-butyl-2-cyanophenylboronic acid | 790 |
| 10 | D-9 | (6-chloronaphthalen-2-yl pinacol boronate) | 2-bromo-5-chlorobenzaldehyde | 1,8-dibromonaphthalene | (4-cyanonaphthalen-1-yl pinacol boronate) | 778 |

TABLE 2-1-continued

| Example | Exemplary compound | Raw material 1 | Raw material 2 | Raw material 3 | Raw material 4 | m/z |
|---|---|---|---|---|---|---|
| 11 | D-10 | | | | | 830 |
| 12 | D-18 | | | | | 706 |
| 13 | D-19 | | | | | 706 |
| 14 | E-2 | | | | | 678 |

TABLE 2-2

| Example | Exemplary compound | Raw material 1 | Raw material 2 | Raw material 3 | Raw material 4 | m/z |
|---|---|---|---|---|---|---|
| 15 | E-5 | | | | | 706 |
| 16 | E-9 | | | | | 734 |
| 17 | E-18 | | | | | 797 |
| 18 | F-3 | | | | | 970 |

TABLE 2-2-continued

| Example | Exemplary compound | Raw material 1 | Raw material 2 | Raw material 3 | Raw material 4 | m/z |
|---|---|---|---|---|---|---|
| 19 | G-8 | | | | | 964 |
| 20 | D-1 | | | | | 678 |
| 21 | D-6 | | | | | 734 |
| 22 | D-13 | | | | | 910 |

TABLE 2-3
| Example | Exemplary compound | Raw material 1 | Raw material 2 | Raw material 3 | Raw material 4 | m/z |
|---|---|---|---|---|---|---|
| 23 | D-22 | 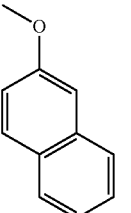 | 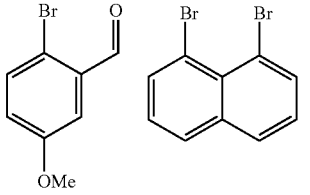 | 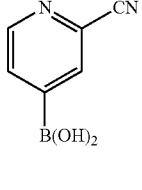 [SMILES: N#Cc1cc(B(O)O)ccn1] |  | 680 |
| 24 | D-25 | 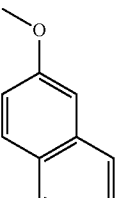 | 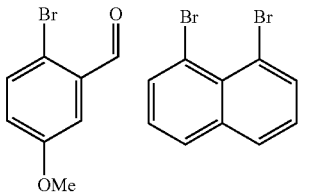 | 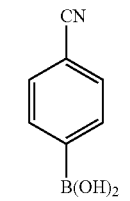 |  | 678 |
| 25 | D-28 | 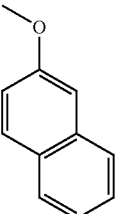 | 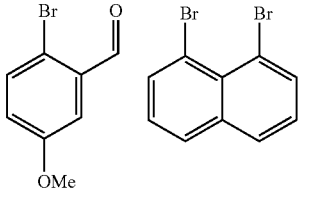 | 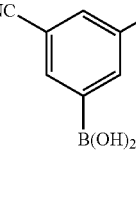 |  | 706 |
| 26 | D-31 | 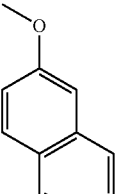 | 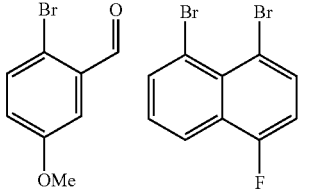 | 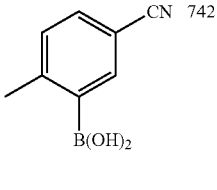 |  | 742 |

TABLE 2-3-continued

| Example | Exemplary compound | Raw material 1 | Raw material 2 | Raw material 3 | Raw material 4 | m/z |
|---|---|---|---|---|---|---|
| 27 | D-33 | 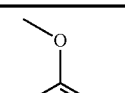 | 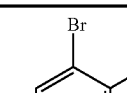 | 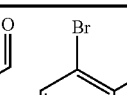 | 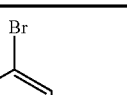 | 728 |

Example 28

In this Example, an organic light-emitting element having the configuration shown in Table 3 was produced. Specifically, a bottom-emission organic light-emitting element was produced in which an anode, a hole injection layer, a hole transport layer, an electron blocking layer, a light-emitting layer, a hole blocking layer, an electron transport layer, an electron injection layer, and a cathode were sequentially formed on an insulating layer.

First, ITO was deposited on a glass substrate, and a desired patterning process was performed to form an ITO electrode (anode). At this time, the thickness of the ITO electrode was set to 100 nm. Such a substrate on which the ITO electrode was formed was used as an ITO substrate in the following process.

Subsequently, organic compound layers and an electrode layer shown in Table 3 were successively formed on the ITO substrate by performing vacuum vapor deposition through resistance heating in a vacuum chamber. At this time, the electrode area of a counter electrode (metal electrode layer, cathode) was set to 3 mm$^2$.

TABLE 3

| | | | Material | Thickness (nm) |
|---|---|---|---|---|
| Cathode | | | Al | 100 |
| Electron injection layer (EIL) | | | LiF | 1 |
| Electron transport layer (ETL) | | | ET2 | 15 |
| Hole blocking layer (HBL) | | | ET12 | 15 |
| Light-emitting layer (EML) | Host | EM4 | Weight ratio EM4:D-5 = 99.5:0.5 | 20 |
| | Guest | D-5 | | |
| Electron blocking layer (EBL) | | | HT12 | 15 |

TABLE 3-continued

| Material | Thickness (nm) |
|---|---|
| Hole transport layer (HTL) | HT3 | 30 |
| Hole injection layer (HIL) | HT16 | 5 |

The characteristics of the obtained element were measured and evaluated. The light-emitting element had a maximum emission wavelength of 445 nm and a maximum external quantum efficiency (E.Q.E) of 4.9%, and emitted blue light having a high color purity with a chromaticity of (X, Y)=(0.14, 0.07). For the measurement instrument, specifically, the current-voltage characteristics were measured with a microammeter 4140B manufactured by Hewlett-Packard Company, and the emission luminance was measured with a BM7 manufactured by TOPCON Corporation. Furthermore, a continuous driving test at a current density of 80 mA/cm$^2$ was performed to measure a time taken when the luminance decrease reached 5%. The time was more than 100 hours. Table 4 shows the measurement results together with those in Examples 29 to 43.

Examples 29 to 43 and Comparative Examples 1 and 2

Organic light-emitting elements were produced by the same method as in Example 28, except that the compounds were appropriately changed to those listed in Table 4. The characteristics of the obtained elements were measured and evaluated in the same manner as in Example 28. Table 4 shows the measurement results.

In Comparative Example 1, an organic light-emitting element was produced and evaluated in the same manner as in Example 29, except that the guest material was changed to J-1. In Comparative Example 2, an organic light-emitting element was produced and evaluated in the same manner as in Example 28, except that the guest material was changed to J-2. Table 4 shows the evaluation results together with the results in Examples.

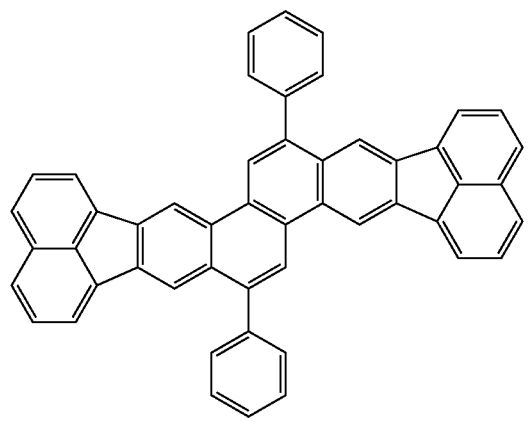

J-1

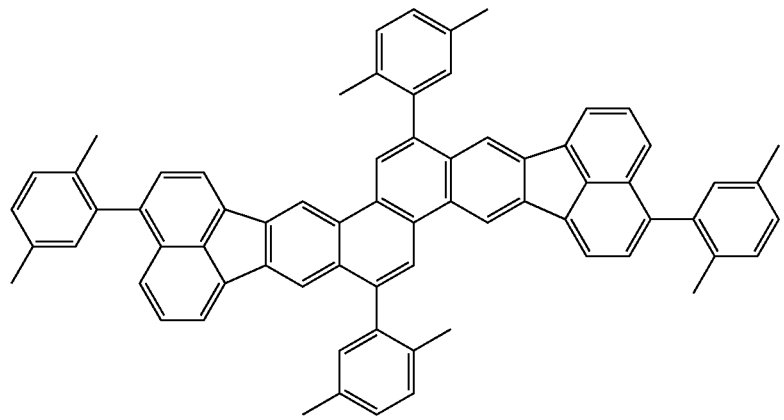

J-2

TABLE 4

|  | HIL | HTL | EBL | EML Host | EML Guest | HBL | ETL | E. Q. E [%] | LT95 [h] | (x, y) |
|---|---|---|---|---|---|---|---|---|---|---|
| Example 28 | HT16 | HT3 | HT12 | EM4 | D-5 | ET12 | ET2 | 4.9 | 105 | (0.14, 0.07) |
| Example 29 | HT16 | HT3 | HT11 | EM1 | D-4 | ET12 | ET2 | 4.8 | 110 | (0.14, 0.08) |
| Example 30 | HT16 | HT2 | HT12 | EM4 | D-9 | ET12 | ET2 | 4.9 | 115 | (0.14, 0.07) |
| Example 31 | HT16 | HT3 | HT11 | EM3 | D-10 | ET10 | ET2 | 4.8 | 105 | (0.14, 0.07) |
| Example 32 | HT16 | HT2 | HT8 | EM3 | D-18 | ET12 | ET3 | 4.8 | 110 | (0.14, 0.07) |
| Example 33 | HT16 | HT2 | HT8 | EM15 | D-19 | ET12 | ET3 | 4.8 | 110 | (0.14, 0.07) |
| Example 34 | HT16 | HT2 | HT8 | EM6 | D-5 | ET12 | ET3 | 4.6 | 120 | (0.14, 0.07) |
| Example 35 | HT16 | HT2 | HT8 | EM1 | D-6 | ET12 | ET3 | 4.7 | 120 | (0.14, 0.07) |
| Example 36 | HT16 | HT2 | HT12 | EM8 | E-2 | ET10 | ET2 | 4.7 | 110 | (0.14, 0.07) |
| Example 37 | HT16 | HT2 | HT12 | EM4 | E-4 | ET12 | ET2 | 4.9 | 105 | (0.14, 0.07) |
| Example 38 | HT16 | HT3 | HT8 | EM1 | E-5 | ET12 | ET2 | 4.8 | 120 | (0.14, 0.08) |
| Example 39 | HT16 | HT3 | HT8 | EM1 | E-18 | ET12 | ET2 | 4.8 | 120 | (0.14, 0.08) |
| Example 40 | HT16 | HT2 | HT12 | EM4 | F-3 | ET12 | ET2 | 4.9 | 105 | (0.14, 0.10) |
| Example 41 | HT16 | HT2 | HT8 | EM1 | G-8 | ET12 | ET2 | 4.8 | 110 | (0.14, 0.10) |
| Example 42 | HT16 | HT2 | HT8 | EM1 | D-22 | ET12 | ET2 | 4.8 | 110 | (0.14, 0.10) |
| Example 43 | HT16 | HT2 | HT8 | EM1 | D-28 | ET12 | ET2 | 4.7 | 110 | (0.14, 0.10) |
| Comparative Example 1 | HT16 | HT3 | HT12 | EM1 | Comparative compound J-1 | ET12 | ET2 | 4.7 | 75 | (0.14, 0.13) |
| Comparative Example 2 | HT16 | HT3 | HT12 | EM4 | Comparative compound J-2 | ET10 | ET2 | 4.7 | 80 | (0.14, 0.13) |

Table 4 shows that Comparative Examples 1 and 2 each have chromaticity coordinates of (0.14, 0.13) and thus have a lower color purity than Examples. Furthermore, the organic light-emitting elements in Comparative Examples having a 5% degradation lifetime of 100 hours or shorter have lower durability than those in Examples each having a 5% degradation lifetime of 105 hours or longer. This is because the comparative compounds do not have the aryl group having at least one cyano group and thus have a low color purity. This is also probably because the comparative compounds do not have a cyano group and thus have low chemical stability because of their low electron acceptability.

On the other hand, the organic light-emitting elements including the organic compounds in Examples have the aryl group having at least one cyano group, and therefore exhibit better blue light-emitting properties with a high color purity than the organic light-emitting elements including the comparative compounds. Furthermore, the organic light-emitting elements including the organic compounds in Examples have higher electron acceptability than the organic light-emitting elements including the comparative compounds. Therefore, such organic light-emitting elements are chemically stable and have a long 5% degradation lifetime.

Example 44

In this Example, an organic light-emitting element having the configuration shown in Table 5 was produced. Specifically, a top-emission organic light-emitting element was produced in which an anode, a hole injection layer, a hole transport layer, an electron blocking layer, a second light-emitting layer, a first light-emitting layer, a hole blocking layer, an electron transport layer, an electron injection layer, and a cathode were sequentially formed on an insulating layer.

A multilayer film of Al and Ti having a thickness of 40 nm was formed on a glass substrate by a sputtering method and patterned by photolithography to form an anode. At this time, the electrode area of a counter electrode (metal electrode layer, cathode) was set to 3 mm$^2$.

Subsequently, the cleaned substrate on which the electrode had been formed and materials were placed in a vacuum evaporation system (manufactured by ULVAC, Inc.), and the system was evacuated to a pressure of $1.3 \times 10^{-4}$ Pa ($1 \times 10^{-6}$ Torr) and then UV/ozone cleaning was performed. Subsequently, layers shown in Table 5 were formed. Lastly, sealing was performed in a nitrogen atmosphere.

TABLE 5

|  |  | Material |  | Thickness (nm) |
|---|---|---|---|---|
| Cathode |  | Mg<br>Ag | Weight ratio<br>Mg:Ag = 50:50 | 10 |
| Electron injection layer (EIL) |  | LiF |  | 1 |
| Electron transport layer (ETL) |  | ET2 |  | 25 |
| Hole blocking layer (HBL) |  | E112 |  | 80 |
| First light-emitting layer (1st EML) | First host<br>First guest (blue dopant) | EM1<br>D-5 | Weight ratio<br>EM1:D-5 = 99.5:0.5 | 15 |
| Second light-emitting layer (2nd EML) | Second host<br>Second guest (red dopant)<br>Third guest (green dopant) | EM1<br>RD1<br><br>GD7 | Weight ratio<br>EM1:RD1:GD7 = 96.7:0.3:3.0 | 10 |
| Electron blocking layer (EBL) |  | HT7 |  | 10 |
| Hole transport layer (HTL) |  | HT2 |  | 20 |
| Hole injection layer (HIL) |  | HT16 |  | 5 |

The characteristics of the obtained element were measured and evaluated. The obtained element exhibited good white light emission. Furthermore, a continuous driving test at an initial luminance of 1000 cd/m$^2$ was performed to measure a luminance decrease after 100 hours. Table 6 shows the results together with those in Examples and Comparative Examples below.

Examples 45 to 52 and Comparative Examples 3 and 4

In these Examples, organic light-emitting elements were produced and evaluated in the same manner as in Example 44, except that the compounds were appropriately changed to those listed in Table 6. Table 6 shows the measurement results.

TABLE 6

|  | 2nd EML | | | 1st EML | | Luminance decrease [%] |
|---|---|---|---|---|---|---|
|  | Second host | Second guest | Third guest | First host | First guest |  |
| Example 44 | EM1 | RD1 | GD7 | EM1 | D-5 | 12 |
| Example 45 | EM1 | RD1 | GD7 | EM3 | D-4 | 13 |

TABLE 6-continued

| | 2nd EML | | | 1st EML | | Luminance decrease [%] |
|---|---|---|---|---|---|---|
| | Second host | Second guest | Third guest | First host | First guest | |
| Example 46 | EM1 | RD1 | GD7 | EM1 | D-18 | 12 |
| Example 47 | EM3 | RD1 | GD7 | EM3 | D-19 | 13 |
| Example 48 | EM3 | RD1 | GD7 | EM3 | D-26 | 14 |
| Example 49 | EM1 | RD1 | GD6 | EM1 | E-5 | 11 |
| Example 50 | EM4 | RD1 | GD6 | EM4 | E-9 | 12 |
| Example 51 | EM2 | RD1 | GD6 | EM2 | E-2 | 13 |
| Comparative Example 3 | EM4 | RD1 | GD6 | EM4 | Comparative compound J-1 | 23 |
| Comparative Example 4 | EM1 | RD1 | GD7 | EM1 | Comparative compound J-2 | 25 |

Table 6 shows that the organic light-emitting elements including the comparative compounds J-1 and J-2 had luminance decreases of 23% and 25%, respectively. This is probably because the comparative compounds do not have the aryl group having at least one cyano group and thus have low chemical stability because of their low electron acceptability.

On the other hand, the organic light-emitting elements including the organic compounds in Examples have the aryl group having at least one cyano group, and therefore exhibit better blue light-emitting properties than the organic light-emitting elements including the comparative compounds. Furthermore, the organic light-emitting elements including the organic compounds in Examples have higher electron acceptability and higher chemical stability than the organic light-emitting elements including the comparative compounds. Therefore, such organic light-emitting elements exhibit high durability.

The organic compound according to an embodiment of the present disclosure is a compound that is suitable for blue light emission and has high chemical stability. Therefore, when the organic compound according to an embodiment of the present disclosure is used as a material for organic light-emitting elements, an organic light-emitting element that has good light-emitting properties required for BT2020 and high durability can be provided.

The present disclosure can provide a blue light-emitting material with a high color purity.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-183347, filed Oct. 3, 2019 and No. 2020-090594, filed May 25, 2020, which are hereby incorporated by reference herein in their entirety.

What is claimed is:

1. An organic compound represented by formula (1),

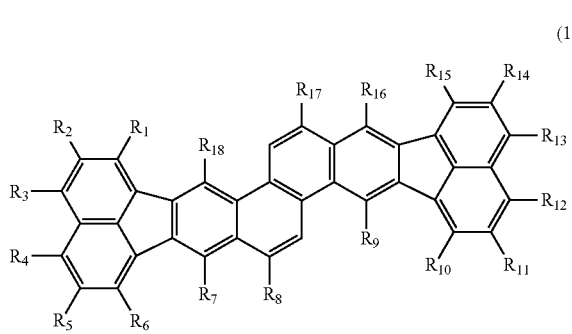

(1)

wherein $R_1$ to $R_{18}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, a substituted or unsubstituted heterocyclic group, a substituted or unsubstituted aryloxy group, a silyl group, and a cyano group, and at least one of $R_1$ to $R_{18}$ represents the aryl group having at least one cyano group or the heterocyclic group having at least one cyano group.

2. The organic compound according to claim 1, wherein in the formula (1), a number of the aryl group having at least one cyano group or the heterocyclic group having at least one cyano group is 1 to 4.

3. The organic compound according to claim 1, wherein in the formula (1), a number of the aryl group having at least one cyano group or the heterocyclic group having at least one cyano group is 1 or 2.

4. The organic compound according to claim 1, wherein in the formula (1), at least one of $R_7$, $R_8$, $R_9$, $R_{16}$, $R_{17}$, and $R_{18}$ represents the aryl group having at least one cyano group or the heterocyclic group having at least one cyano group.

5. The organic compound according to claim 1, wherein in the formula (1), any two of $R_7$, $R_8$, $R_9$, $R_{16}$, $R_{17}$, and $R_{18}$ represent the aryl group having at least one cyano group or the heterocyclic group having at least one cyano group.

6. The organic compound according to claim 1, wherein at least one of $R_7$, $R_8$, $R_9$, $R_{16}$, $R_{17}$, and $R_{18}$ in the formula (1) represents the aryl group having at least one cyano group or the heterocyclic group having at least one cyano group, and wherein the aryl group having at least one cyano group or the heterocyclic group having at least one cyano group is not introduced to positions other than $R_7$, $R_8$, $R_9$, $R_{16}$, $R_{17}$, and $R_{18}$ in the formula (1).

7. The organic compound according to claim 1, wherein in the formula (1), none of $R_3$, $R_4$, $R_{12}$, and $R_{13}$ represents the aryl group having at least one cyano group or the heterocyclic group having at least one cyano group.

8. The organic compound according to claim 7, wherein in the formula (1), $R_3$, $R_4$, $R_{12}$, and $R_{13}$ represent a hydrogen atom.

9. The organic compound according to claim 1, wherein an aryl group that constitutes the aryl group having at least one cyano group is selected from the group consisting of a phenyl group, a naphthyl group, and a biphenyl group.

10. The organic compound according to claim 1, wherein a heterocyclic group that constitutes the heterocyclic group having at least one cyano group is selected from the group consisting of a pyridyl group, a pyrimidyl group, a pyrazyl group, a triazyl group, a benzofuranyl group, a benzothiophenyl group, a dibenzofuranyl group, and a dibenzothiophenyl group.

11. An organic light-emitting element comprising:
a first electrode;
a second electrode; and
an organic compound layer disposed between the first electrode and the second electrode,
wherein the organic compound layer includes the organic compound according to claim 1.

12. The organic light-emitting element according to claim 11,
wherein at least one layer in the organic compound layer is a light-emitting layer, and
the light-emitting layer includes the organic compound.

13. The organic light-emitting element according to claim 11, wherein the organic light-emitting element emits blue light.

14. The organic light-emitting element according to claim 12,
wherein the organic compound layer further includes a second light-emitting layer disposed together with the light-emitting layer so as to form a multilayer structure, and
the second light-emitting layer emits light having a color different from a color of light emitted from the light-emitting layer.

15. The organic light-emitting element according to claim 14, wherein the organic light-emitting element emits white light.

16. A display apparatus comprising a plurality of pixels,
wherein at least one of the plurality of pixels includes the organic light-emitting element according to claim 11 and a transistor connected to the organic light-emitting element.

17. An image pickup apparatus comprising:
an optical unit including a plurality of lenses;
an image pickup element that receives light which has passed through the optical unit; and
a display unit that displays an image captured by the image pickup element,
wherein the display unit includes the organic light-emitting element according to claim 11.

18. An electronic apparatus comprising:
a display unit including the organic light-emitting element according to claim 11;
a housing in which the display unit is disposed; and
a communication unit that is disposed in the housing and communicates with an external unit.

19. A lighting apparatus comprising:
a light source including the organic light-emitting element according to claim 11; and
a light diffusion unit or an optical film that transmits light emitted from the light source.

20. A moving object comprising:
a lighting fixture including the organic light-emitting element according to claim 11; and
a body on which the lighting fixture is disposed.

21. The organic compound according to claim 1, wherein at least one of $R_4$, $R_7$, $R_8$, $R_{13}$, $R_{16}$, and $R_{17}$ in the formula (1) represents the aryl group having at least one cyano group or the heterocyclic group having at least one cyano group, and
wherein the aryl group having at least one cyano group or the heterocyclic group having at least one cyano group is not introduced to positions other than $R_4$, $R_7$, $R_8$, $R_{13}$, $R_{16}$, and $R_{17}$ in the formula (1).

22. The organic compound according to claim 1, wherein at least one of $R_7$, $R_8$, $R_{16}$, and $R_{17}$ in the formula (1) represents the aryl group having at least one cyano group or the heterocyclic group having at least one cyano group, and
wherein the aryl group having at least one cyano group or the heterocyclic group having at least one cyano group is not introduced to positions other than $R_7$, $R_8$, $R_{16}$, and $R_{17}$ in the formula (1).

23. The organic compound according to claim 1, wherein at least one of $R_1$ to $R_{18}$ represents the aryl group having one cyano group or the heterocyclic group having one cyano group.

24. The organic compound according to claim 1, wherein at least one of $R_7$, $R_8$, $R_9$, $R_{16}$, $R_{17}$, and $R_{18}$ represents the aryl group having one cyano group or the heterocyclic group having one cyano group.

* * * * *